US008642657B2

(12) United States Patent
Lee et al.

(10) Patent No.: US 8,642,657 B2
(45) Date of Patent: Feb. 4, 2014

(54) 4-(METHYL SULFONYL AMINO) PHENYL ANALOGUES AS VANILLOID ANTAGONIST SHOWING EXCELLENT ANALGESIC ACTIVITY AND THE PHARMACEUTICAL COMPOSITIONS COMPRISING THE SAME

(75) Inventors: Jee Woo Lee, Ansan-si (KR); Young Ho Kim, Ansan-si (KR); Hee Kim, Ansan-si (KR); Hyun Kyung Choi, Ansan-si (KR); Hee Jin Ha, Ansan-si (KR)

(73) Assignee: Gruenenthal GmbH, Aachen (DE)

( * ) Notice: Subject to any disclaimer, the term of this patent is extended or adjusted under 35 U.S.C. 154(b) by 1840 days.

(21) Appl. No.: 10/562,698

(22) PCT Filed: Jul. 2, 2004

(86) PCT No.: PCT/KR2004/001641
§ 371 (c)(1),
(2), (4) Date: May 10, 2006

(87) PCT Pub. No.: WO2005/003084
PCT Pub. Date: Jan. 13, 2005

(65) Prior Publication Data
US 2006/0258884 A1 Nov. 16, 2006

(30) Foreign Application Priority Data
Jul. 2, 2003 (KR) ........................ 10-2003-0044552

(51) Int. Cl.
*A61K 31/17* (2006.01)
*A61K 31/18* (2006.01)
(52) U.S. Cl.
USPC ................ 514/605; 514/595; 564/47; 564/56
(58) Field of Classification Search
USPC .......................... 564/99, 47, 56; 514/605, 595
See application file for complete search history.

(56) References Cited

FOREIGN PATENT DOCUMENTS

WO WO02/16318 A1 2/2002
WO WO02/16319 2/2002

OTHER PUBLICATIONS

Chong Hyun Ryu, "Chain-branched 1,3-dibenzylthioureas as vanilloid receptor 1 antagonists", Bioorganic & Medicinal Chemistry Letters, 2004, pp. 1751-1755, vol. 14, No. 7 XP-002402881.
European Search Report dated Oct. 13, 2006 (Two (2) pages).
Christopher S.J. Walpole et al., "Structural Requirements for Capsaicin Agonists and Antagonists", 1993, pp. 63-81.
Yun Wang et al., "High Affinity Antagonists of the Vanilloid Receptor", Mar. 12, 2002, vol. 62, No. 4, pp. 947-956.
Guy R. Seabrook et al., "Functional Properties of the High-Affinity TRPV1 (VR1) Vanilloid Receptor Antagonist (4-Hydroxy-5-iodo-3-methoxyphenylacetate ester) Iodo-Resiniferatoxin", The Journal of Pharmcology and Experimental Therapeutics 2002, vol. 303, No. 3, pp. 1052-1060.
M.J. Gunthorpe et al., "Identification and characterisation of SB-366791, a potent and selective vanilloid receptor (Vr1/TRPV1) antagonist", Neuropharmacology, 2004, vol. 46, pp. 133-149.
Martin J. Gunthorpe et al., "The diversity in the vanilloid (TRPV) receptor family of ion channels", Trends in Pharmacological Sciences, Apr. 2002., vol. 23, No. 4, pp. 183-191.
Yun Wang et al., "High-Affinity Partial Agonists of the Vanilloid Receptor", Molecular Pharmacology, Dec. 24, 2002., vol. 64, No. 2, pp. 325-333.
Qun Sun et al., "4-(2-Pyridyl)piperazine-1-carboxamides: Potent Vanilloid Receptor 1 Antagonists", Bioorganic & Medicinal Chemistry Letters, Mar. 14, 2003, vol. 13, pp. 3611-3616.
Peter M. Zygmunt et al., "Vanilloid receptors on sensory nerves mediate the vasodilator action of anandamide", Macmillan Magazines, Nature, Jul. 29, 1999, vol. 400, pp. 452-457.
Young-Ger Suh et al., "Novel Non-vanilloid VR1 Antagonist of High Analgesic Effects and Its Structural Requirement for VR1 Antagonistic Effects", Bioorganic & Medicinal Chemistry Letters, 2003, vol. 13, pp. 4389-4393.
Philip Hayes et al., "Cloning and functional expression of a human orthologue of rat vanilloid receptor-1", Pain, 2000, vol. 88, pp. 205-215.
Sun Wook Hwang et al., "Direct activation of capsaicin receptors by products of lipoxygenases: Endogenous capsaicin-Like substances", PNAS, May 23, 2000, vol. 97, No. 11, pp. 6155-6160.
Arpad Szallasi et al., "Vailloid (Capsaicin) Receptors and Mechanisms", Pharmacological Reviews, vol. 51, No. 2; pp. 159-211.
Sven-Eric Jordt et al., "Molecular Basis for Species-Specific Sensitivity to "Hot" Chili Peppers", Department of Cellular and Molecular Pharmacology, Univ. of California, Feb. 8, 2002, vol. 108, pp. 421-430.
Attila Tóth et al., "Design of a High-Affinity Competitive Antagonist of the Vanilloid Receptor Selective for the Calcium Entry-Linked Receptor Population", Molecular Pharmacology, vol. 65, No. 2, pp. 282-291.
Mark E. McDonnell et al., "7-Hydroxynaphthalen-1-yl-urea and —amide Antagonists of Human Vanilloid Receptor 1", Bioorganic & Medicinal Chemistry Letters, 2004, vol. 14, pp. 531-534.
Giovanni Appendino et al., Halogenation of a capsaicin analogue leads to novel vanilloid TRPV1 receptor antagonists, British Journal of Pharmacology. 2003, vol. 139, pp. 1417-1424.
Giovanni Appendino et al., "Euphorbium: Modern Research on its Active Principle, Resiniferatoxin, Revives an Ancient Medicine", Life Sciences, 1997, vol. 60, No. 10, pp. 681-696.
Philip Wahl et al., "Iodo-Resiniferatoxin, a New Potent Vanilloid Receptor Antagonist", Molecular Pharmacology, vol. 59, No. 1, pp. 9-15.
Craig Montell et al., "The TRP Channels, a Remarkably Functional Family", Mini-review, Cell, Mar. 8, 2002, vol. 108, pp. 595-598.

(Continued)

*Primary Examiner* — Peter O Sullivan
(74) *Attorney, Agent, or Firm* — Crowell & Moring LLP

(57) ABSTRACT

4-(methylsulfonylamino)phenyl analogues as potent vanilloid receptor antagonists and pharmaceutical compositions comprising the same. The compounds are useful as analgesics to prevent, alleviate or treat pain diseases or inflammatory disease including pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease, inflammatory disease and urgent urinary incontinence.

13 Claims, No Drawings

(56) References Cited

OTHER PUBLICATIONS

M.J. Caterina et al., "Impaired Nociception and Pain Sensation in Mice Lacking the Capsaicin Receptor", Apr. 14, 2000. Science, Research Articles, vol. 288, pp. 306-313.

Christopher S.J. Walpole et al., "The Discovery of Capsazepine, the First Competitive Antagonist of the Sensory Neuron Excitants Capsaicin and Resiniferatoxin", Journal of Medicinal Chemistry, 1994, vol. 37, No. 13, pp. 1942-1954.

James D. Pomonis et al., "N-(4-Tertiarybutylphenyl)-4-(3-Cholorphyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain", The Journal of Pharmacology and Experimental Therapeutics, vol. 306, No. 1.; pp. 387-393.

Narender R.Gavva et al., "Molecular Determinants of Vanilloid Sensitivity in TRPV1", The Journal of Biological Chemistry, May 7, 2004, vol. 279, No. 19, pp. 20283-20295.

Makoto Tominaga et al., "The Cloned Capsaicin Receptor Integrates Multiple Pain-Producing Stimuli", Neuron, Sep. 1998, vol. 21, pp. 531-543.

Michael J. Caterina et al., "The capsaicin receptor: a heat-activated ion channel in the pain pathway", Nature, Oct. 1997, vol. 389, pp. 816-824.

Jeewoo Lee et al. "N-(3-Acyloxy-2-benzylpropyl)-N-[4-(methysulfonylamino)benzyl]thiourea Analogues: Novel Potent and High Affinity Antagonists and Partial Antagonists of the Vanilloid Receptor", Journal of Medicinal Chemistry, 2003, vol. 46, No. 14, pp. 3116-3126.

Jeewoo Lee et al., "N-(3-Acyloxy-2-benzylpropyl)-$N^1$-(4-hydroxy-3-methoxybenzyl) thiourea Derivatives as Potent Vanilloid Receptor Agonists and Analgesics", Bioorgianic & Medicinal Chemistry, 2001, vol. 9, pp. 19-32.

Kenneth J. Valenzano et al. "N-(4-Tertiarybutylphenyl)-4-(3-chloropyridin-2-yl)tetrahydropyrazine-1(2H)-carbox-amide (BCTC), a Novel, Orally Effective Vanilloid Receptor 1 Antagonist with Analgesic Properties: I. In Vitro Characterization and Pharmacokinetic Properties", The Journal of Pharmacology and Experimental Therapeutics, vol. 306, No. 1, pp. 377-386.

Yun Wawng, et al., "High affinity antagonists of the vanilloid receptor", Molecular Pharmacology, 2002, 62(4), 947-956.

Jeewoo Lee et al., N-(3-Acyloxy-2-benzylpropyl)-N'-[4-methylsulfonylamino)benzyl]thiourea Analogues: Novel Poten and High Affinity Antagonists and Partial Antagonists of the Vanilloid Receptor, Journal of medicinal chemistry, Jul. 3, 2003, 46(14) 3116-3126.

Yun Wang et al., "High affinity partial agonist of the vanilloid receptor", Molecular Pharmarcology, Aug. 2002, 64(2), 325-333.

International Search Report.

4-(METHYL SULFONYL AMINO) PHENYL ANALOGUES AS VANILLOID ANTAGONIST SHOWING EXCELLENT ANALGESIC ACTIVITY AND THE PHARMACEUTICAL COMPOSITIONS COMPRISING THE SAME

TECHNICAL FIELD

The present invention relates to novel 4-(methylsulfonylamino)phenyl analogues as vanilloid antagonist showing excellent analgesic activity and the pharmaceutical compositions comprising the same.

BACKGROUND ART

The vanilloid receptor (VR1) is a member of the transient receptor potential (TRP) superfamily. Members of this family are non-voltage activated cation channel proteins that play critical roles in processes ranging from sensory physiology to vasorelaxation and male fertility. They share structural similarities such as six transmembrane segments and an oligmeric structure (Montell, C. et al., Cell, 108, p 595, 2002). The vanilloid or capsaicin receptor (VR1 or TRPV1) has been cloned from dorsal root ganglia (DRG) of the rat, the human, the chicken, the guinea pig, and the rabbit (Szallasi, A. et al., Pharmacol. Rev., 51, p 159, 1999; Caterina, M. J. et al., Nature, 389, p 816, 1997; Hayes, P. et al., Pain, 88, p 205, 2000; Jordt et al., Cell, 108, p 421, 2002; Savidge, J. et al., Neuropharmacology, 43, p 450, 2002; Gavva, N. R. et al., J. Biol. Chem., in press, 2004). Vanilloid receptor homologues have also been cloned but are not believed to be sensitive to vanilloids (Gunthorpe, M. J. et al, Trends in Pharmacol. Sci., 23, p 183, 2002). VR1, which is expressed predominantly on thin, unmyelinated sensory nerve fibers (C-fibers) and small A fibers in the dorsal root, trigeminal, and nodose ganglia, is a molecular integrator of nociceptive stimuli. VR1 is activated by protons, heat, natural exogenous ligands such as capsaicin (CAP) or resiniferatoxin (RTX), and endogenous substances such as anandamide and the lipoxygenase product 12-HPETE (Tominaga M. et al., Neuron, 21, p 531; 1998; Caterina, M. J. et al., Nature, 389, p 816, 1997; Walpole C. S. J. et al., Capsaicin in the Study of Pain, Academic Press, San Diego, Calif., p 63, 1993; Appendino, G. et al., Life Sci., 60, p 681, 1997; Zygmunt, P. M. et al., Nature, 400, p 452, 1991; Hwang S. W. et al., Proc. Natl. Acad. Sci. U.S.A., 97, p 6155, 2000). Since VR1 functions as a non-selective cation channel with high $Ca^{2+}$ permeability, its activation by these agents leads to an increase in intracellular $Ca^{2+}$ that results in excitation of primary sensory neurons and ultimately the central perception of pain. Chronic stimulation of VR1 leads to desensitization/defunctionalization of the neurons, probably reflecting multiple mechanisms.

The involvement of VR1 in both pathological and physiological conditions suggests that the blocking of this receptor, by desensitization or by antagonism, would have considerable therapeutic utility. Among its therapeutic targets, pain is of particular interest. The validation of VR1 as a molecular target for the treatment of chronic pain was confirmed using transgenic mice lacking functional VR1 receptors. These mice exhibited impairment in the perception of thermal and inflammatory pain (Caterina, M. J. et al., Science, 288, p 306, 2000).

The therapeutical advantage of VR1 antagonism over desensitization subsequent to agonism is that it avoids the initial excitatory effect preceding the desensitization. The initial acute pain associated with capsaicin treatment has proven to be the limiting toxicity. After the discovery of capsazepine as the first VR1 antagonist (Walpole, C. S. J et al., J. Med. Chem., 37, p 1942, 1994), a number of antagonists have been reported both with structures related and unrelated to agonists (Walpole, C. S. J. et al, J. Med. Chem., 37, p 1942, 1994). Among them, 5-Iodo-RTX, SC0030, halogenated capsaicin analogues, BCTC, SB-366791, 7-hydroxynaphthalen-1-yl urea, and IBTU were characterized in detail as potent VR1 competitive antagonists (Wahl, P. et al., Mol. Pharmacol., 59, p 9, 2001; Seabrook, G. R. et al., J. Pharmacol. Exp. Ther. 303, p 1052, 2002; Wang, Y. et al., Mol. Pharmacol., 62, p 947, 2002; Suh, Y-G. et al., Bioorg. Med. Chem. Lett., 13, p 4389, 2003; Appendino, G. et al., Br. J. Pharmacol., 139, p 1417, 2003; Valenzano, K. J. et al., J. Pharmacol. Exp. Ther., 306, p 377, 2003; Pomonis, J. D. et al., J. Pharmacol. Exp. Ther., 306, p 387, 2003; Sun, Q. et al., Bioorg. Med. Chem. Lett., 13, p 3611, 2003; Gunthorpe, M. J. et al., Neuropharm., 46, p 133, 2004; McDonnell, M. E. et al., Bioorg. Med. Chem. Lett., 14, p 531, 2004; Toth, A. et al., Mol. Pharm., 65, p 282, 2004).

We have previously reported that isosteric replacement of the phenolic hydroxyl group in potent vanilloid receptor agonists (Lee, J. et al., Chem., 9, p 19, 2001) with the alkylsulfonamido group provided a series of compounds which are effective antagonists to the action of capsaicin on rat VR1 heterologously expressed in Chinese hamster ovary (CHO) cells. As a prototype, N-[2-(3,4-dimethylbenzyl)-3-pivaloyloxypropyl]-N'-[4-(methylsulfonylamino)benzyl]thiourea (1) showed a high binding affinity with a $K_i$ value of 29.3 nM for the inhibition of [$^3$H]RTX binding and potent antagonism with an $IC_{50}$ value of 67 nM for the inhibition of $^{45}Ca^{2+}$ uptake in response to capsaicin, displaying partial agonism (Wang, Y et al., Pharm., 64, p 325, 2003). Compound 2, 3-fluoro analogue, showed very potent antagonism with IC50=7.8 nM and analgesic activity in writhing test (Lee, J et al., Med. Chem., 46, p 3116, 2003).

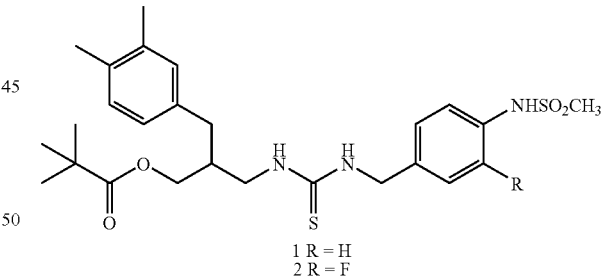

1 R = H
2 R = F

The present inventors have been extensively endeavored to discover novel analgesic agents based on the above studies and finally completed the present invention by synthesizing novel 4-(methylsulfonylamino)phenyl analogues as vanilloid antagonist showing excellent analgesic activity and the pharmaceutical compositions comprising the same.

DISCLOSURE OF THE INVENTION

Thus, the present invention provides novel compounds represented by the following formula (I), the pharmaceutically acceptable salt or the isomer thereof:

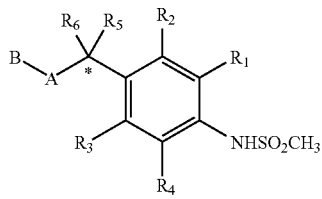
(I)

wherein,

A is CONH, NHCO, NHC(=S)NH, NHC(=O)NH;

$R_1$ to $R_4$ is independently at least one selected from a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, five or six-member heterocyclic ring;

$R_5$ and $R_6$ is independently at least one selected from a hydrogen, hydroxyl group, amino group, straight or branched alkyl group having 1 to 6 carbon atoms, cycloalkyl group having 1 to 6 carbon atoms and phenyl or benzyl group optionally substituted with at least one selected from halogen atom, amine group and alkyl group having 1 to 6 carbon, providing that both of $R_5$ and $R_6$ are not hydrogen atom simultaneously;

B is a group selected from

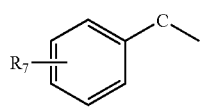
(I-1)

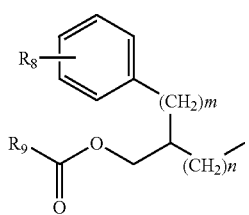
(I-2)

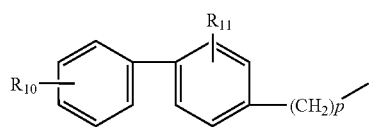
(I-3)

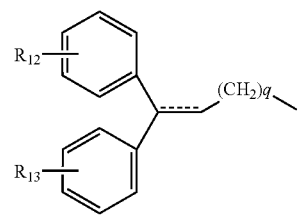
(I-4)

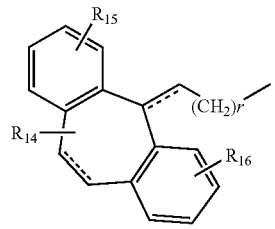
(I-5)

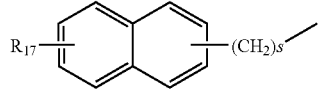
(I-6)

in which $R_7$ to $R_{17}$ is independently at least one selected from a hydrogen, halogen atom and straight or branched alkyl group having 1 to 6 carbon atoms optionally substituted with more than one halogen atom, C is a group selected from alkyl, alkenyl and alkynyl group having 1 to 5 carbon atoms which may includes one or more heteroatoms, m, n, p, q, r and s is an integer of 0 to 3;

an asteric mark * and (┄) mark indicate a chiral carbon atom, and double bond or single bond chain respectively.

Examples of "alkyl group" used herein include, but are not limited to, methyl, ethyl, propyl and the like, and Examples of "heterocyclic ring" used herein include, but are not limited to, pyrrole, pyrazole, pyrazine, purine, pyridine, piperazine, piperidine, thiazole, morpholine, dioxane and the like.

Preferable groups in general formula (I) of the present invention are the group in which $R_5$ or $R_6$ is methyl, ethyl, propyl, isopropyl, phenyl or benzyl and $R_7$ or $R_8$ is isopropyl, t-butyl or sec-butyl group, but are limited thereto.

The compounds of general formula (I) of the present invention comprise all the compounds represented by following formula (I) to (V) in accordance with the definition of A group.

Accordingly, the present invention provides novel compounds represented by the following formula (II), the pharmaceutically acceptable salt or the isomer thereof:

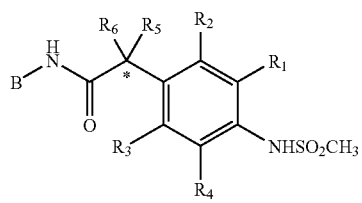
(II)

wherein, $R_1$ to $R_4$ is independently at least one selected from a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, five or six-member heterocyclic ring;

$R_5$ and $R_6$ is independently at least one selected from a hydrogen, hydroxyl group, amino group, straight or branched alkyl group having 1 to 6 carbon atoms, cycloalkyl group having 1 to 6 carbon atoms and phenyl or benzyl group optionally substituted with at least one selected from halogen atom, amine group and alkyl group having 1 to 6 carbon, providing that both of $R_5$ and $R_6$ are not hydrogen atom simultaneously;

B is a group selected from the group (I-1) to (I-6) defined in general formula (I);

the asteric mark * indicates a chiral carbon atom.

In preferred embodiment in general formula (II), the most preferred compound is one selected from the group consisting of;

N-(4-tert-butylbenzyl)-2-[3-fluoro-4-(methylsulfonylamino)phenyl]propionamide (1-51, KMJ-372), N-(4-tert-butylbenzyl)-2-[3-chloro-4-(methylsulfonylamino)phenyl]propionamide (1-52, KMJ-470), N-(4-tert-butylbenzyl)-2-[3-bromo-4-(methylsulfonylamino)phenyl]propionamide (1-53, SH-173), N-(4-tert-butylbenzyl)-2-[3-iodo-4-(methylsulfonylamino)phenyl]propionamide (1-54, SH-168), N-(4-tert-butylbenzyl)-2-[3,5-difluoro-4-(methylsulfonylamino)phenyl]propionamide (1-55, SH-285), N-(4-tert-butylbenzyl)-2-[3-cyano-4-(methylsulfonylamino)phenyl]propionamide (1-56, SH-219), N-(4-tert-butylbenzyl)-2-[3-(tert-butoxycarbonyl-4-(methylsulfonylamino)phenyl]propionamide (1-57, KMJ-806), N-(4-tert-butylbenzyl)-2-[3-carboxyl-4-(methylsulfonylamino)phenyl]propionamide (1-58, KMJ-788), N-(4-tert-butylbenzyl)-2-[3-methoxycarbonyl-4-(methylsulfonylamino)phenyl]propionamide (1-59, KMJ-838), N-(4-tert-butylbenzyl)-2-[3-(benzylamino)carbonyl-4-(methylsulfonylamino)phenyl]propionamide (1-60, KMJ-836), N-(4-tert-butylbenzyl)-2-[3-piperidino-4-(methylsulfonylamino)phenyl]propionamide (1-61, YS-65), N-(4-tert-butylbenzyl)-2-[3-morpholino-4-(methylsulfonylamino)phenyl]propionamide (1-62, YS-49), N-(4-tert-butylbenzyl)-2-[3-(N-Boc)piperazino-4-(methylsulfonylamino)phenyl]propionamide (1-63, YS-76), N-(4-tert-butylbenzyl)-2-[3-piperazino-4-(methylsulfonylamino)phenyl]propionamide (1-64, YS-79), N-(4-tert-butylbenzyl)-2-[3-methoxy-4-(methylsulfonylamino)phenyl]propionamide (1-65, CHK-717), N-(4-tert-butylbenzyl)-2-[2-fluoro-4-(methylsulfonylamino)phenyl]propionamide (1-66, KMJ-708), N-(4-tert-butylbenzyl)-2-[2-chloro-4-(methylsulfonylamino)phenyl]propionamide (1-67, KMJ-698), N-(4-tert-butylbenzyl)-2-[4-(methylsulfonylamino)phenyl]propionamide (2-7, KMJ-750), N-(4-chloro)-2-[4-(methylsulfonylamino)phenyl]propionamide (2-8, YS-85), N-(3,4-dichloro)-2-[4-(methylsulfonylamino)phenyl]propionamide (2-9, YS-97), N-(4-tert-butylbenzyl)-(2S)-2-[3-fluoro-4-(methylsulfonylamino)phenyl]propionamide (3-5, SU-834), N-(4-tert-butylbenzyl)-(2R)-2-[3-fluoro-4-(methylsulfonylamino)phenyl]propionamide (3-6, SU-824), N-(4-chlorobenzyl)-2-[3-fluoro-4-(methylsulfonylamino)phenyl]propionamide (4-1, SH-291), N-(4-chlorobenzyl)-2-[3-chloro-4-(methylsulfonylamino)phenyl]propionamide (4-2, SH-290), N-(4-chlorobenzyl)-2-[3-bromo-4-(methylsulfonylamino)phenyl]propionamide (4-3, SH-335), N-(3,4-dichlorobenzyl)-2-[3-fluoro-4-(methylsulfonylamino)phenyl]propionamide (4-4, SH-94), N-(3,4-dichlorobenzyl)-2-[3-chloro-4-(methylsulfonylamino)phenyl]propionamide (4-5, SH-286), N-(3,4-dichlorobenzyl)-2-[3-bromo-4-(methylsulfonylamino)phenyl]propionamide (4-6, SH-337), N-(4-methylbenzyl)-2-[3-fluoro-4-(methylsulfonylamino)phenyl]propionamide (4-7, SH-351), N-(4-isopropylbenzyl)-2-[3-fluoro-4-(methylsulfonylamino)phenyl]propionamide (4-8, KMJ-928), N-(4-methoxybenzyl)-2-[3-fluoro-4-(methylsulfonylamino)phenyl]propionamide (4-9, SH-353), N-(4-trifluoromethylbenzyl)-2-[3-fluoro-4-(methylsulfonylamino)phenyl]propionamide (4-10, SH-93), N-(4-phenylbenzyl)-2-[3-fluoro-4-(methylsulfonylamino)phenyl]propionamide (4-11, KMJ-498), N-(1-naphthylmethyl)-[3-fluoro-4-(methylsulfonylamino)phenyl]propionamide (4-12, SH-92), N-(1,2,3,4-tetrahydro-1-naphthalenyl)-2-[3-fluoro-4-(methylsulfonylamino)phenyl]propionamide (4-13, SH-112), N-[2-(4-tert-butylphenyl)ethy]-2-[3-fluoro-4-(methylsulfonylamino)phenyl]propionamide (4-14, KMJ-374), N-[3-(3,4-dimethylphenyl)propyl]-2-[3-fluoro-4-(methylsulfonylamino)phenyl]propionamide (4-15, SU-770), N-[3-(3,4-dimethylphenyl)propyl]-(2R)-2-[3-fluoro-4-(methylsulfonylamino)phenyl]propionamide (4-16, SU-774), N-[3-(3,4-dimethylphenyl)propyl]-(2S)-2-[3-fluoro-4-(methylsulfonylamino)phenyl]propionamide (4-17, SU-776), N-[3-(3,4-dimethylphenyl)-2-prophenyl]-2-[3-fluoro-4-(methylsulfonylamino)phenyl]propionamide (4-18, KMJ-686), N-[3-(4-chlorophenyl)propyl]-2-[3-fluoro-4-(methylsulfonylamino)phenyl]propionamide (4-19, KMJ-518), N-[3-(4-chlorophenyl)-2-prophenyl]-2-[3-fluoro-4-(methylsulfonylamino)phenyl]propionamide (4-20, KMJ-732), N-benzyloxy-2-[3-fluoro-4-(methylsulfonylamino)phenyl]propionamide (4-21, SH-109), N-(benzhydryl)-2-[3-fluoro-4-(methylsulfonylamino)phenyl]propionamide (4-22, SH-130), N-(2,2-diphenylethy)-2-[3-fluoro-4-(methylsulfonylamino)phenyl]propionamide (4-23, SH-116), N-(3,3-diphenylpropyl)-2-[3-fluoro-4-(methylsulfonylamino)phenyl]propionamide (4-24, KMJ-378), N-(3,3-diphenyl-2-prophenyl)-2-[3-fluoro-4-(methylsulfonylamino)phenyl]propionamide (4-25, KMJ-724), N-[3,3-di(4-methylphenyl)-2-prophenyl]-2-[3-fluoro-4-(methylsulfonylamino)phenyl]propionamide (4-26, KMJ-908), N-[3,3-di(4-fluorophenyl)-2-prophenyl]-2-[3-fluoro-4-(methylsulfonylamino)phenyl]propionamide (4-27, SH-135), N-[2-(10,11-dihydro-5H-dibenzo[a,d]cyclohepten-5-yliden)ethy]-2-[3-fluoro-4-(methylsulfonylamino)phenyl]propionamide (4-28, SH-199), N-[2-(3,4-dimethylbenzyl)-3-pivaloxypropyl]-2-[4-(methylsulfonylamino)phenyl]propionamide (5-1, CHK-512), N-[2-(4-tert-butylbenzyl)-3-pivaloxypropyl]-2-[4-(methylsulfonylamino)phenyl]propionamide (5-2, CHK-514), 2-[3-fluoro-4-(methylsulfonylamino)phenyl]-N-[2-(3,4-dimethylbenzyl)-3-pivaloxypropyl]propionamide (5-3, SU-542), 2-[3-fluoro-4-(methylsulfonylamino)phenyl]-N-[2-4-tert-butylbenzyl)-3-pivaloxypropyl]propionamide (5-4, SU-564), N-[2-(3,4-dimethylbenzyl)-3-pivaloxypropyl]-2-[3-methoxy-4-(methylsulfonylamino)phenyl]propionamide (5-5, CHK-479), N-[2-(4-tert-butylbenzyl)-3-pivaloxypropyl]-2-[3-methoxy-4-(methylsulfonylamino)phenyl]propionamide (5-6, CHK-499), N-[2-(3,4-dimethylbenzyl)-3-pivaloxypropyl]-2-[3-chloro-4-(methylsulfonylamino)phenyl]propionamide (5-7, KNJ-472), N-[2-(4-tert-butylbenzyl)-3-pivaloxypropyl]-2-[3-chloro-4-(methylsulfonylamino)phenyl]propionamide (5-8, KMJ-690), N-[(1R)-1-benzyl-2-(pivaloxy)ethy]-(2S)-2-[3-fluoro-4-(methylsulfonylamino)phenyl]propionamide (6-1, SU-730), N-[(1S)-1-benzyl-2-(pivaloxy)ethy]-(2S)-2-[3-fluoro-4-(methylsulfonylamino)phenyl]propionamide (6-2, SU-634), N-[(1S)-1-benzyl-2-(pivaloxy)ethy]-(2R)-2-[3-fluoro-4-(methylsulfonylamino)phenyl]propionamide (6-3, SU-636), N-[(1R)-1-benzyl-2-(pivaloxy)ethy]-(2R)-2-[3-fluoro-4-(methylsulfonylamino)phenyl]propionamide (6-4, SU-728), N-[(2R)-2-benzyl-3-(pivaloxy)propyl]-(2S)-2-[3-fluoro-4-(methylsulfonylamino)phenyl]propionamide (6-5, SU-826), N-[(2S)-2-benzyl-3-(pivaloxy)propyl]-(2S)-2-[3-fluoro-4-(methylsulfonylamino)phenyl]propionamide (6-6, SU-830), N-[(2S)-2-benzyl-3-(pivaloxy)propyl]-(2R)-2-[3-fluoro-4-(methylsulfonylamino)phenyl]propionamide (6-7, SU-838), N-[(2R)-2-benzyl-3-(pivaloxy)propyl]-(2R)-2-[3-fluoro-4-

(methylsulfonylamino)phenyl]propionamide (6-8, SU-818), N-[(2R)-2-(4-tert-butyl)benzyl-3-(pivaloxy)propyl]-(2S)-2-[3-fluoro-4-(methylsulfonylamino)phenyl]propionamide (6-9, MK-271), N-[(2S)-2-(4-tertbutyl)benzyl-3-(pivaloxy)propyl]-(2S)-2-[3-fluoro-4-(methylsulfonylamino)phenyl]propionamide (6-10, MK-272), N-[(2S)-2-(4-tertbutyl)benzyl-3-(pivaloxy)propyl]-(2R)-2-[3-fluoro-4-(methylsulfonylamino)phenyl]propionamide (6-11, MK-450), N-[(2R)-2-(4-tertbutyl)benzyl-3-(pivaloxy)propyl]-(2R)-2-[3-fluoro-4-(methylsulfonylamino)phenyl]propionamide (6-12, MK-452), N-[(2R)-2-(4-tertbutyl)benzyl-3-(pivaloxy)propyl]-(2S)-2-[3-chloro-4-(methylsulfonylamino)phenyl]propionamide (6-13, MK-453), N-[(2S)-2-(4-tertbutyl)benzyl-3-(pivaloxy)propyl]-(2S)-2-[3-chloro-4-(methylsulfonylamino)phenyl]propionamide (6-14, MK-451), 2-[3-fluoro-4-(methylsulfonylamino)phenyl]-2-methylpropion acid (7-4, CHK-624), 2-[4-(methylsulfonylamino)phenyl]-2-methylpropion acid (8-11), 2-[3-methoxy-4-(methylsulfonylamino)phenyl]-2-methylpropion acid (8-12), N-[2-(3,4-dimethylbenzyl)-3-pivaloxypropyl]-2-[4-(methylsulfonylamino)phenyl]-2-methylpropionamide (9-1, CHK-520), N-[2-(3,4-dimethylbenzyl)-3-pivaloxypropyl]-2-[3-fluoro-4-(methylsulfonylamino)phenyl]-2-methylpropionamide (9-2, CHK-543), N-[2-(3,4-dimethylbenzyl)-3-pivaloxypropyl]-2-[3-methoxy-4-(methylsulfonylamino)phenyl]-2-methylpropionamide (9-3, CHK-493), N-[3-(3,4-dimethylphenyl)propyl]-2-[4-(methylsulfonylamino)phenyl]-2-methylpropionamide (9-4, CHK-591), N-[3-(3,4-dimethylphenyl)propyl]-2-[3-fluoro-4-(methylsulfonylamino)phenyl]-2-methylpropionamide (9-5, CHK-656), N-[3-(3,4-dimethylphenyl)propyl]-2-[3-methoxy-4-(methylsulfonylamino)phenyl]-2-methylpropionamide (9-6, CHK-600), N-(4-tert-butylbenzyl)-2-[4-(methylsulfonylamino)phenyl]-2-methylpropionamide (9-7, CHK-715), N-(4-tert-butylbenzyl)-2-[3-fluoro-4-(methylsulfonylamino)phenyl]-2-methylpropionamide (9-8, CHK-655), N-(4-tert-butylbenzyl)-2-[3-methoxy-4-(methylsulfonylamino)phenyl]-2-methylpropionamide (9-9), 1-[3-fluoro-4-(methylsulfonylamino)phenyl]cycloprophan carboxic acid (10-5), 1-[4-(methylsulfonylamino)phenyl]cyclopropan carboxic acid (11-7, CHK-530), 1-[3-methoxy-4-(methylsulfonylamino)phenyl]cyclopropan carboxic acid (11-8), N-[2-(3,4-dimethylbenzyl)-3-pivaloxypropyl]-1-[4-(methylsulfonylamino)phenyl]cyclopropan carboxiamide (12-1, CHK-533), N-[2-(3,4-dimethylbenzyl)-3-pivaloxypropyl]-1-[3-fluoro-4-(methylsulfonylamino)phenyl]cyclopropan carboxiamide (12-2, CHK-538), N-[2-(3,4-dimethylbenzyl)-3-pivaloxypropyl]-1-[3-methoxy-4-(methylsulfonylamino)phenyl]cyclopropan carboxiamide (12-3, CHK-541), N-[3-(3,4-dimethylphenyl)propyl]-1-[4-(methylsulfonylamino)phenyl]cyclopropan carboxiamide (12-4, CHK-590), N-[3-(3,4-dimethylphenyl)propyl]-1-[3-fluoro-4-(methylsulfonylamino)phenyl]cyclopropan carboxiamide (12-5), N-[3-(3,4-dimethylphenyl)propyl]-1-[3-methoxy-4-(methylsulfonylamino)phenyl]cyclopropan carboxiamide (12-6, CHK-632), N-(4-tert-butylbenzyl)-1-[4-(methylsulfonylamino)phenyl]cyclopropan carboxiamide (12-7, CHK-719), N-(4-tert-butylbenzyl)-1-[3-fluoro-4-(methylsulfonylamino)phenyl]cyclopropan carboxiamide (12-8, CHK-659), N-(4-tert-butylbenzyl)-1-[3-methoxy-4-(methylsulfonylamino)phenyl]cyclopropan carboxiamide (12-9, CHK-718).

And, the present invention provides novel compounds represented by the following formula (III).

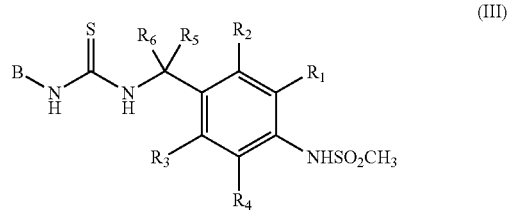

wherein, $R_1$ to $R_4$ is independently at least one selected from a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, five or six-member heterocyclic ring providing that all of $R_1$ to $R_4$ are not hydrogen atoms simultaneously;

$R_5$ and $R_6$ is independently at least one selected from a hydrogen, hydroxyl group, amino group, straight or branched alkyl group having 1 to 6 carbon atoms, cycloalkyl group having 1 to 6 carbon atoms and phenyl or benzyl group optionally substituted with at least one selected from halogen atom, amine group and alkyl group having 1 to 6 carbon, providing that both of $R_5$ and $R_5$ are not hydrogen atom simultaneously;

B is a group selected from the group (I-1) to (I-6) defined in general formula (I);

the asteric mark * indicates a chiral carbon atom.

In preferred embodiment in general formula (III), the most preferred compound is one selected from the group consisting of;

N-(4-tert-butylbenzyl)-N'-{1-[3-fluoro-4-(methylsulfonylamino)phenyl]ethyl}thiourea (15-1, LJO-328), N-(4-tert-butylbenzyl)-N'-{1-[3-chloro-4-(methylsulfonylamino)phenyl]ethyl}thiourea (15-2, CHK-992), N-(4-tert-butylbenzyl)-N'-{1-[3-methoxy-4-(methylsulfonylamino)phenyl]ethyl}thiourea (15-3, CHK-575), N-(4-tert-butylbenzyl)-N'-{1-[3-(methoxycarbonyl)-4-(methylsulfonylamino)phenyl]ethyl}thiourea (15-4, YHS-187), N-(4-tert-butylbenzyl)-N'-{1-[3-carboxy-4-(methylsulfonylamino)phenyl]ethyl}thiourea (15-5, YHS-209), N-(4-tert-butylbenzyl)-N'-{(1R)-1-[4-(methylsulfonylamino)phenyl]ethyl}thiourea (16-5, SU-388), N-(4-tert-butylbenzyl)-N'-{(1S)-1-[4-(methylsulfonylamino)phenyl]ethyl}thiourea (16-6, SU-400), N-(4-tert-butylbenzyl)-N'-{(1R)-1-[3-fluoro-4-(methylsulfonylamino)phenyl]ethyl}thiourea (17-3, CJU-032), N-(4-tert-butylbenzyl)-N'-{(1S)-1-[3-fluoro-4-(methylsulfonylamino)phenyl]ethyl}thiourea (17-6, CJU-039), N-[(2R)-2-benzyl-3-(pivaloyloxy)prophyl]-N'-{(1R)-1-[4-(methylsulfonylamino)phenyl]ethyl}thiourea (18-1, MK-229), N-[(2S)-2-benzyl-3-(pivaloyloxy)prophyl]-N'-{(1R)-1-[4-(methylsulfonylamino)phenyl]ethyl}thiourea (18-2, MK-202), N-[(2R)-2-benzyl-3-(pivaloyloxy)prophyl]-N'-{(1S)-1-[4-(methylsulfonylamino)phenyl]ethyl}thiourea (18-3, MK-230), N-[(2S)-2-benzyl-3-(pivaloyloxy)prophyl]-N'-{(1S)-1-[4-(methylsulfonylamino)phenyl]ethyl}thiourea (18-4, MK-228), N-[2-(3,4-dimethylbenzyl)-3-(pivaloyloxy)prophyl]-N'-{1-[4-(methylsulfonylamino)phenyl]ethyl}thiourea (18-5, LJO-388), N-[2-(3,4-dimethylbenzyl)-3-(pivaloyloxy)prophyl]-N'-{(1R)-1-[4-(methylsulfonylamino)phenyl]ethyl}thiourea (18-6, SU-472), N-[(2R)-2-(3,4-dimethylbenzyl)-3-(pivaloyloxy)prophyl]-N'-{(R)-1-[4-(methylsulfonylamino)phenyl]ethyl}thiourea (18-7, SU-512), N-[(2S)-2-(3,4-dimethylbenzyl)-3-(pivaloyloxy)prophyl]-N'-{(1R)-1-[4-(methylsulfonylamino)phenyl]ethyl}thiourea (18-8), N-[2-(4-tert-butylbenzyl)-3-(pivaloyloxy)prophyl]-N'-{1-[4-(methylsulfonylamino)phenyl]ethyl}thiourea (18-9, LJO-401), N-[2-(4-tert-butylbenzyl)-3-(pivaloyloxy)prophyl]-N'-{1(R)-[4-(methylsulfonylamino)phenyl]ethyl}thiourea (18-10, MK-296), N-[2(R)-(4-tert-butylbenzyl)-3-(pivaloyloxy)prophyl]-N'-{1(R)-[4-(methylsulfonylamino)phenyl]ethyl}thiourea (18-11, MK-334), N-[2(S)-(4-tert-butylbenzyl)-3-(pivaloyloxy)prophyl]-N'-{1(R)-[4-(methylsulfonylamino)phenyl]ethyl}thiourea (18-12, MK-298), N-[2-(3,4-(dimethylbenzyl)-3-(pivaloyloxy)prophyl]-N'-{1-[3-fluoro-4-(methylsulfonylamino)phenyl]ethyl}thiourea (18-13, LJO-344), N-[2-(4-tert-butylbenzyl)-3-(pivaloyloxy)prophyl]-N'-{1-[3-fluoro-4-(methylsulfonylamino)phenyl]ethyl}thiourea (18-14, LJO-366), N-[(2R)-3-phenyl-1-pivaloyloxy-2-prophyl]-N'-[(R)-α-methyl-4-(methylsulfonylamino)benzyl]thiourea (19-13, SU-692), N-[(2S)-3-phenyl-1-pivaloyloxy-2-prophyl]-N'-[(R)-α-methyl-4-(methylsulfonylamino)benzyl]thiourea (19-14, SU-704), N-[(2R)-3-phenyl-1-pivaloyloxy-2-prophyl]-N'-[(S)-α-methyl-4-(methylsulfonylamino)benzyl]thiourea (19-15, SU-720), N-[(2S)-3-phenyl-1-pivaloyloxy-2-prophyl]-N'-[(S)-α-methyl-4-(methylsulfonylamino)benzyl]thiourea (19-16, SU-710), N-(4-tert-butylbenzyl)-N'-{1-[4-(methylsulfonylamino)-3-fluorophenyl]prophyl}thiourea (20-12, LJO-399), N-(4-tert-butylbenzyl)-N'-{1-[4-(methylsulfonylamino)-3-fluorophenyl]-2-methylprophyl}thiourea (20-13, LJO-402), N-(4-tert-butylbenzyl)-N'-{[4-(methylsulfonylamino)-3-fluorophenyl](phenyl)methyl}thiourea (20-14, LJO-403), N-(4-tert-butylbenzyl)-N'-{1-[4-(methylsulfonylamino)-3-fluorophenyl]-2-phenylethyl}thiourea (20-15, LJO-395), N-(4-tert-butylbenzyl)-N'-{1-methyl-1-[4-(methylsulfonylamino)phenyl]ethyl}thiourea (21-7, CHK-593), N-(4-tert-butylbenzyl)-N'-{1-methyl-1-[3-fluoro-4-(methylsulfonylamino)phenyl]ethyl}thiourea (21-8, CHK-660), N-(4-tert-butylbenzyl)-N'-{1-methyl-1-[3-methoxy-4-(methylsulfonylamino)phenyl]ethyl}thiourea (21-9, CHK-629), N-(4-tert-butylbenzyl)-N'-{1-[4-(methylsulfonylamino)phenyl]cycloprophyl}thiourea (22-7, CHK-579), N-(4-tert-butylbenzyl)-N'-{1-[3-fluoro-4-(methylsulfonylamino)phenyl]cycloprophyl}thiourea (22-8), N-(4-tert-butylbenzyl)-N'-{1-[3-methoxy-4-(methylsulfonylamino)phenyl]cycloprophyl}thiourea (22-9, CHK-631).

And, the present invention provides novel compounds represented by the following formula (IV).

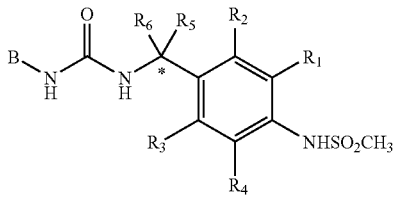

(IV)

wherein, $R_1$ to $R_4$ is independently at least one selected from a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, five or six-member heterocyclic ring;

$R_5$ and $R_6$ is independently at least one selected from a hydrogen, hydroxyl group, amino group, straight or branched alkyl group having 1 to 6 carbon atoms, cycloalkyl group having 1 to 6 carbon atoms and phenyl or benzyl group optionally substituted with at least one selected from halogen atom, amine group and alkyl group having 1 to 6 carbon, providing that both of $R_5$ and $R_6$ are not hydrogen atom simultaneously;

B is a group selected from the group (I-1) to (I-6) defined in general formula (I);

the asteric mark * indicates a chiral carbon atom.

In preferred embodiment in general formula (IV), the most preferred compound is one selected from the group consisting of;

N-(4-tert-butylbenzyl)-N'-{1-[4-(methylsulfonylamino)phenyl]ethyl}urea (23-1, MK-82), N-(4-tert-butylbenzyl)-N'-{1-[3-fluoro-4-(methylsulfonylamino)phenyl]ethyl}urea (23-2, MK-205)

And, the present invention provides novel compounds represented by the following formula (V).

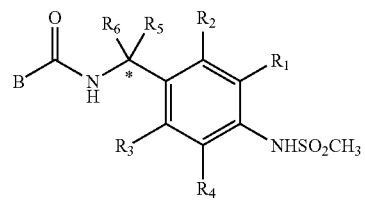

(V)

wherein, $R_1$ to $R_4$ is independently at least one selected from a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, five or six-member heterocyclic ring;

$R_5$ and $R_6$ is independently at least one selected from a hydrogen, hydroxyl group, amino group, straight or branched alkyl group having 1 to 6 carbon atoms, cycloalkyl group having 1 to 6 carbon atoms and phenyl or benzyl group optionally substituted with at least one selected from halogen atom, amine group and alkyl group having 1 to 6 carbon, providing that both of $R_5$ and $R_6$ are not hydrogen atom simultaneously;

B is a group selected from the group (I-1) to (I-6) defined in general formula (I);

the asteric mark * indicates a chiral carbon atom.

In preferred embodiment in general formula (V), the most preferred compound is one selected from the group consisting of, N-{1-[3-fluoro-4-(methylsulfonylamino)phenyl]ethyl}-3-(4-tert-butylphenyl)acetamide (24-1, KMJ-586), N-{1-[3-fluoro-4-(methylsulfonylamino)phenyl]ethyl}-3-(4-tert-butylphenyl)prophanamide (24-2, KMJ-552), N-{1-[3-fluoro-4-(methylsulfonylamino)phenyl]ethyl}-3-(4-tert-butylphenyl)-2-prophenamide (24-3, KMJ-570), N-{1-[3-fluoro-4-(methylsulfonylamino)phenyl]ethyl}-3-(3,4-dimethylphenyl)prophanamide (24-4, CHK-602), N-{1-[3-fluoro-4-(methylsulfonylamino)phenyl]ethyl}-3-(3,4-dimethylphenyl)-2-prophenamide (24-5, CHK-651), N-{1-[3-fluoro-4-(methylsulfonylamino)phenyl]ethyl}-3-(4-chlorophenyl)prophenamide (24-6, KMJ-534), N-{1-[3-fluoro-4-(methylsulfonylamino)phenyl]ethyl}-3-(4-chlorophenyl)-2-prophenamide (24-7, KMJ-558),
N-{1-[3-fluoro-4-(methylsulfonylamino)phenyl]ethyl}-3-(3,4-dimethylphenyl)buthanamide (24-8, CHK-647).

The term "salt" used herein comprises all the pharmaceutically salts well known in the art.

The inventive compounds represented by general formula (I) to (V) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluenesulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the compound represented by general formula (I) to (V) comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonatmesylate) salt and p-toluenesulfonate (tosylate) salt etc, which can be prepared by the conventional method well known in the art.

The term "isomer" used herein comprises all the isomers, for example, stereoisomer, optically active isomer, racemic mixture, enantiomer and the like well known in the art.

There may exist in the form of optically different diastereomers since the compounds of the present invention have one or more unsymmetrical centers (*), accordingly, the compounds of the present invention comprise all the optically active isomers, R or S stereoisomers and the mixtures thereof. Present invention also comprises all the uses of the racemic mixture, one or more optically active isomer and the mixtures thereof as well as all the preparation methods for preparing the isomers, for example, unsymmetric synthesis, and isolation methods for isolating the isomers, for example, partitioned re-crystalization method, chromatographic method well known in the art or the method disclosed herein.

And, the present invention provides a process for preparing novel compounds represented by general formula (I) to (V) described herein comprising the methods explained by following preferred embodiments or examples.

The compounds of the invention of formula (I) to (V) may be chemically synthesized by the methods which will be explained by following reaction schemes hereinafter, which are merely exemplary and in no way limit the invention. The reaction schemes show the steps for preparing the representative compounds of the present invention, and the other compounds also may be produced by following the steps with appropriate modifications of reagents and starting materials, which are envisaged by those skilled in the art.

General Synthetic Procedures

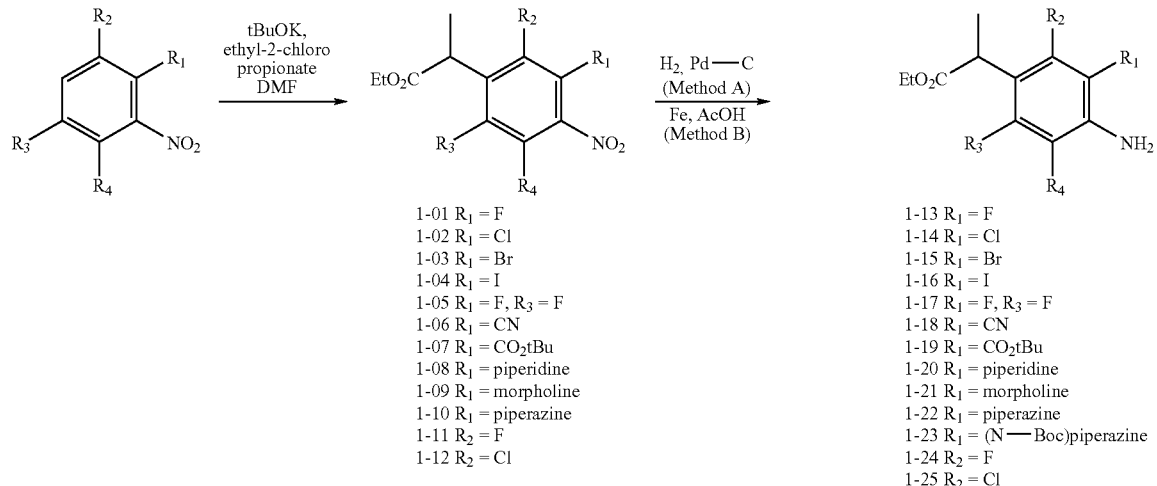

-continued

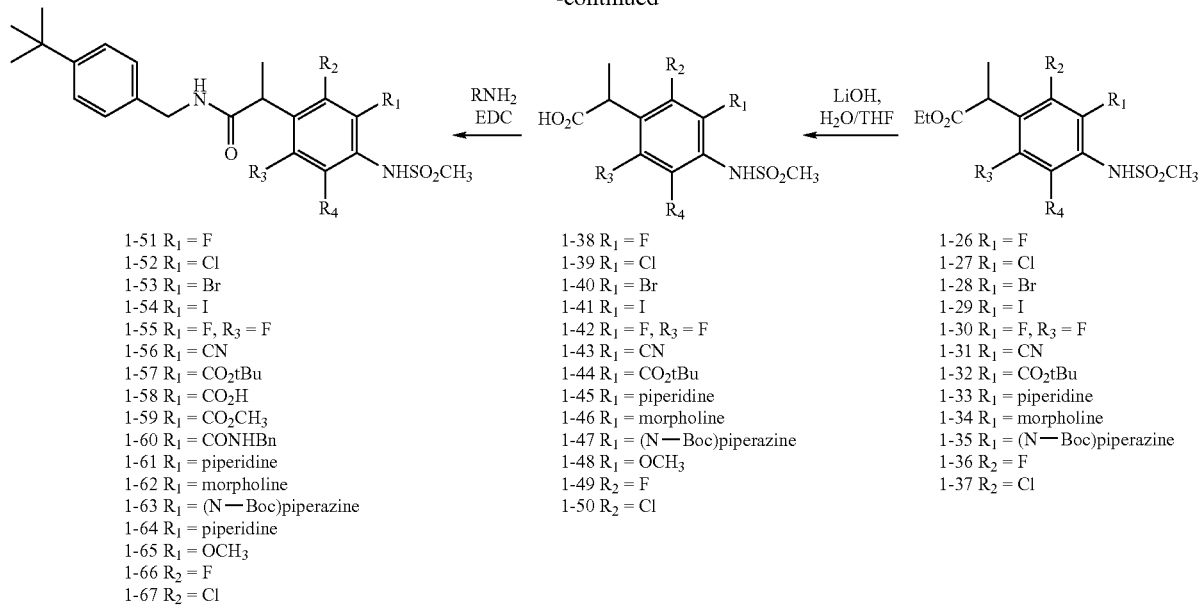

1-51 R₁ = F
1-52 R₁ = Cl
1-53 R₁ = Br
1-54 R₁ = I
1-55 R₁ = F, R₃ = F
1-56 R₁ = CN
1-57 R₁ = CO₂tBu
1-58 R₁ = CO₂H
1-59 R₁ = CO₂CH₃
1-60 R₁ = CONHBn
1-61 R₁ = piperidine
1-62 R₁ = morpholine
1-63 R₁ = (N—Boc)piperazine
1-64 R₁ = piperidine
1-65 R₁ = OCH₃
1-66 R₂ = F
1-67 R₂ = Cl 1-38 R₁ = F
1-39 R₁ = Cl
1-40 R₁ = Br
1-41 R₁ = I
1-42 R₁ = F, R₃ = F
1-43 R₁ = CN
1-44 R₁ = CO₂tBu
1-45 R₁ = piperidine
1-46 R₁ = morpholine
1-47 R₁ = (N—Boc)piperazine
1-48 R₁ = OCH₃
1-49 R₂ = F
1-50 R₂ = Cl 1-26 R₁ = F
1-27 R₁ = Cl
1-28 R₁ = Br
1-29 R₁ = I
1-30 R₁ = F, R₃ = F
1-31 R₁ = CN
1-32 R₁ = CO₂tBu
1-33 R₁ = piperidine
1-34 R₁ = morpholine
1-35 R₁ = (N—Boc)piperazine
1-36 R₂ = F
1-37 R₂ = Cl As depicted in above Scheme 1, the reaction consists of five steps as follows: at 1$^{st}$ step, the mixture of nitrobenzene having various $R_1$ to $R_4$ substituents and ethyl-2-halogenpropionate such as ethyl-2-chloropropionate is reacted with metal salt alkoxide solution such as potassium-t-butoxide dissolved in DMF dropwisely at the temperature ranging from 0° C. to room temperature, in the period ranging from 3 to 30 min, preferably 10 mins. The reaction is stopped by acid e.g., 1N-HCl, diluted with water and repeatedly extracted with diethyether to obtain organic solvent layer. The organic solvent layer is washed with water and saline water, dried, concentrated in vacuo and the residue is further purified with flash column chromatographic method to obtain ethyl 2-(3-halo-4-nitrophenyl)propionate intermediate compound (1-1 to 1-12) through the alkylation of 4-position in phenyl ring; at 2$^{nd}$ step, the propionate intermediate compound (1-1 to 1-12) is reduced with reducing agent for example, 10% Pd/C (hydrogenation reaction, method A) or Fe ion in the presence with acetic acid (method B). The resulting product is filtered and the filtrates is dried in vacuo and purified with purified with flash column chromatographic method to obtain ethyl 2-(4-amino-3-halo phenyl)propionate intermediate compound (1-13 to 1-25) through reducing nitro group to amino group; at 3$^{rd}$ step, the propionate compound (1-13 to 1-25) is reacted with sulfonyl halide, preferably, methanesulfonylchloride dissolved in pyridine solvent with stirring and the resulting product is washed with water and purified with flash column chromatographic method to obtain ethyl 2-(3-halo-4 (methylsulfonyamino)phenyl) propionate intermediate compound (1-26 to 1-37) through sulfonylation process; at 4$^{th}$ step, the propionate compound (1-26 to 1-37) dissolved in solvent mixture mixed with water and THF is reacted with metal hydroxide such as lithium hydroxide dropwisely with stirring and acidified with acidic solution such as 1N-HCl solution to obtain organic layer. The organic layer is extracted and dried to produce carboxylic acid compound (1-38 to 1-50) through hydrolysis process; at 5$^{th}$ step, the 2-[3-halo-4-(methylsulfonylamino)phenyl]propionate is added dropwisely to EDC solution containing amine compound such as 4-t-butylbenzylamine at the temperature ranging from 0° C. to room temperature, stirred, filtrated, concentrated and the resulting residue is further purified with purified with flash column chromatographic method to obtain purposed final product, N-(4-t-butylbenzyl)-2-[2 or 3-substituted-4-(methylsulfonylamino)phenyl]propionamide compound (1-51 to 1-67), a derivative represented by general formula (II) having B group (I-2), through coupling acid with amine group.

Scheme 2

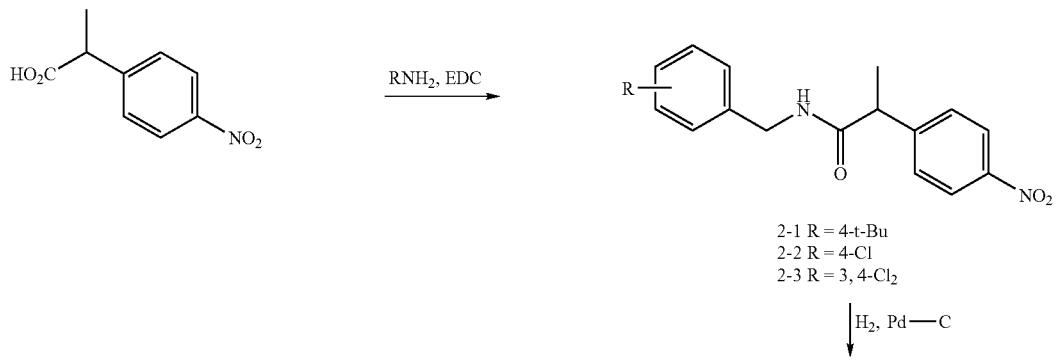

2-1 R = 4-t-Bu
2-2 R = 4-Cl
2-3 R = 3, 4-Cl₂

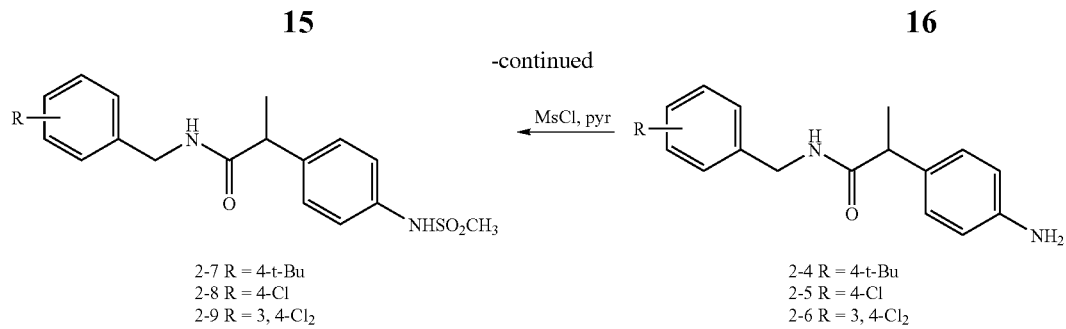

As depicted in above Scheme 2, the compound represented by general formula (II) having A group (NHCO), $R_5$ (methyl) and $R_6$ (H) can be prepared by following procedure: conventionally available 2(4-nitrophenyl)propionic acid is coupling with amine ($RNH_2$) to produce amide (2-1 to 2-3) and the amide is reduced to produce amine compound (2-4 to 2-6). Finally, the amine is subjected to methylsulfonylation to obtain final product (2-7 to 2-9).

The compound represented by general formula (II) can comprises various optical isomers e.g., enantiomer, stereoisomer, diastereomer etc, according to the B moiety containing chiral carbon and the various isomers can be synthesized and isolated by the procedure explained by following Scheme 3 and 4.

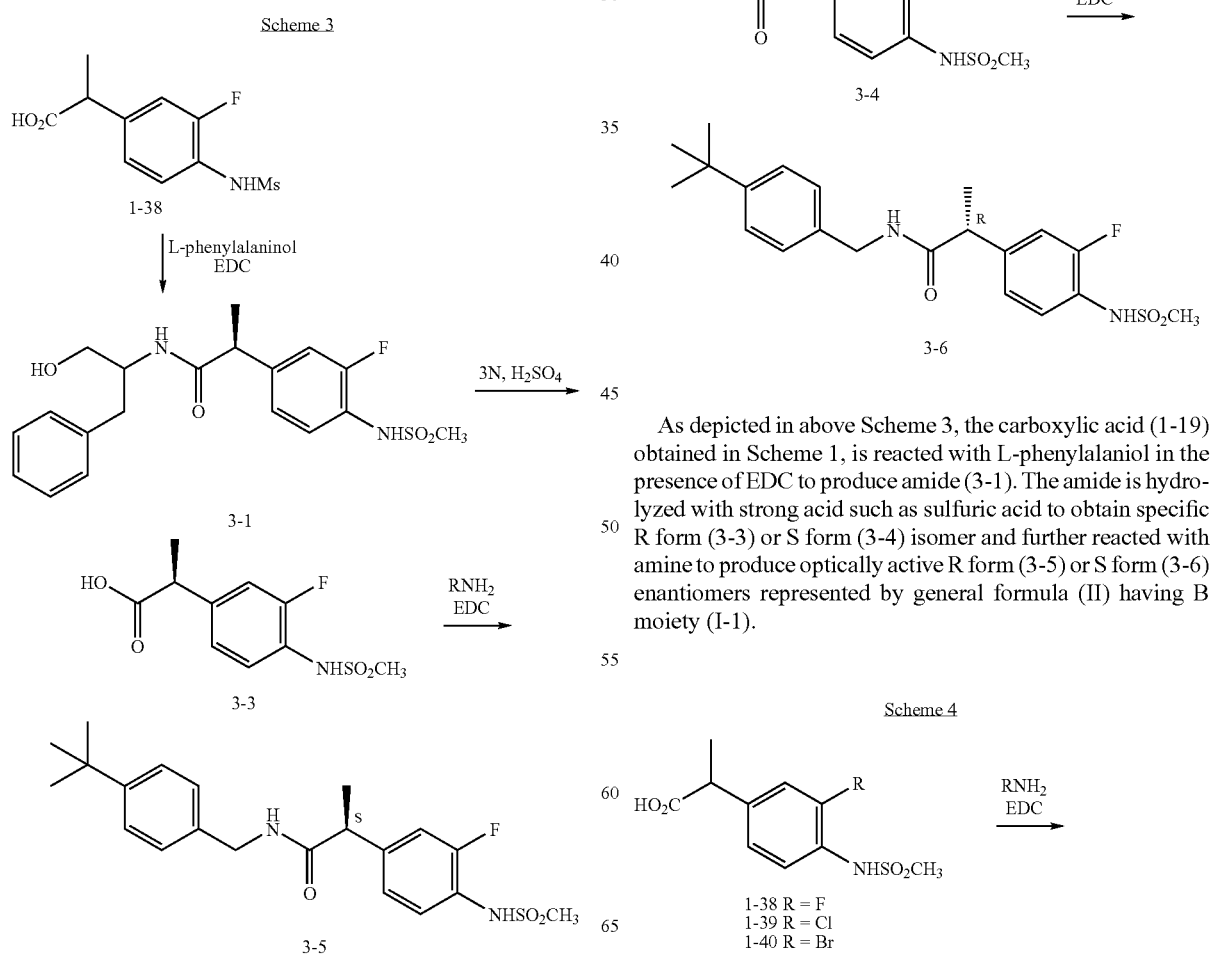

As depicted in above Scheme 3, the carboxylic acid (1-19) obtained in Scheme 1, is reacted with L-phenylalaninol in the presence of EDC to produce amide (3-1). The amide is hydrolyzed with strong acid such as sulfuric acid to obtain specific R form (3-3) or S form (3-4) isomer and further reacted with amine to produce optically active R form (3-5) or S form (3-6) enantiomers represented by general formula (II) having B moiety (I-1).

-continued

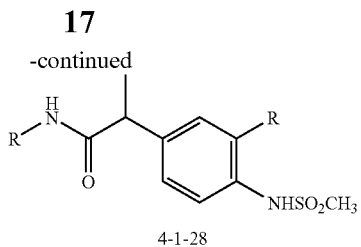

4-1-28

As depicted in above Scheme 4, the carboxylic acid (1-38 to 1-40) obtained in Scheme 1, is reacted with anine having appropriate B substituents in the presence of EDC to produce purposed amide compound represented by general formula (II) having B moiety (I-2).

Scheme 5

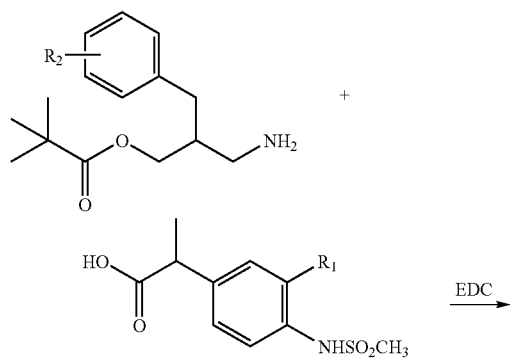  EDC →

-continued

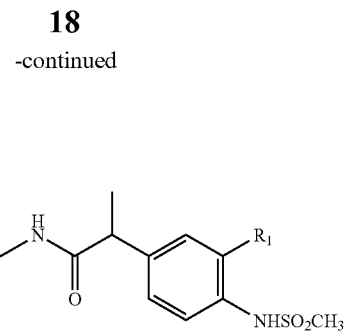

5-1 $R_1$ = H    $R_2$ = 3,4-Me$_2$
5-2 $R_1$ = H    R2 = 4-t-Bu
5-3 $R_1$ = F    $R_2$ = 3,4-Me$_2$
5-4 $R_1$ = F    $R_2$ = 4-t-Bu
5-5 $R_1$ = OCH$_3$  $R_2$ = 3,4-Me$_2$
5-6 $R_1$ = OCH$_3$  $R_2$ = 4-t-Bu
5-7 $R_1$ = Cl   $R_2$ = 3,4-Me$_2$
5-8 $R_1$ = Cl   R2 = 4-t-Bu

As depicted in above Scheme 5, the carboxylic acid obtained in Scheme 1, is reacted with amine having appropriate B substituents in the presence of EDC to produce purposed amide compound represented by general formula (II) having B moiety (I-2).

Scheme 6

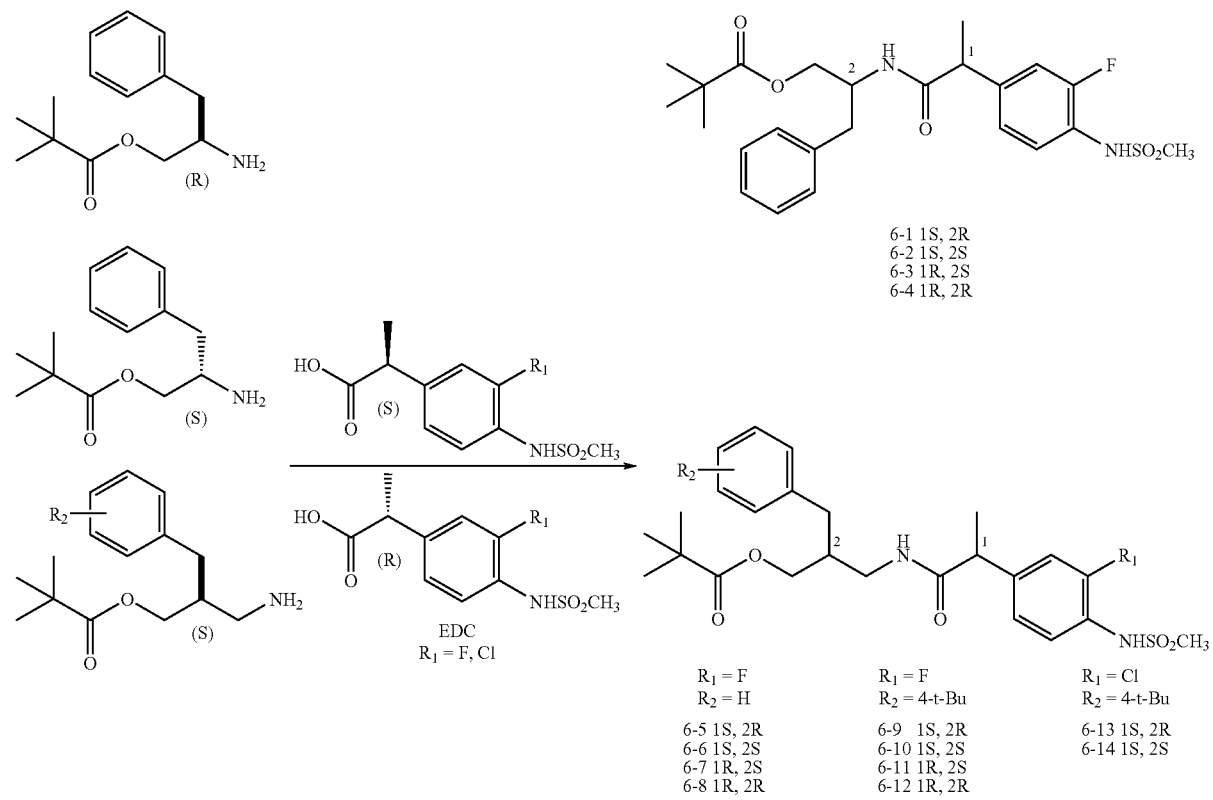

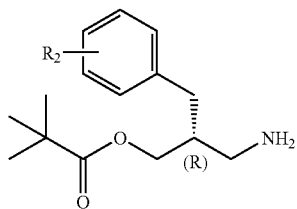

As depicted in above Scheme 6, the carboxylic acid obtained in Scheme 1, is reacted with amine having appropriate B substituents in the presence of EDC to produce purposed optically active amide compound represented by general formula (II) having B moiety (I-2) containing chiral carbon.

The B—$NH_2$ moiety (I-2) having (R) form or (S) form enantiomers due to chiral carbon positioned at 2 is reacted with (R) form or (S) form of carboxylic acid obtained in Scheme 1 to produce various optically active stereoisomers, i.e., (1S, 2R), (1S, 2S), (1R, 2R) and (1R, 2S).

The compound having lower alkyl group at $R_5$ and $R_6$ can be prepared by following procedures shown in Scheme 7 and Scheme 8:

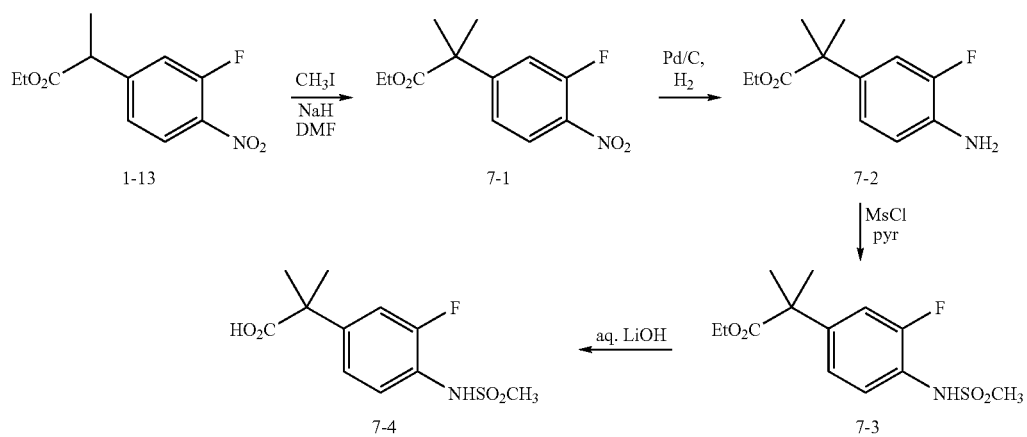

For example, as depicted in above Scheme 7, the compound having halogen atom at any of $R_1$ and $R_4$ can prepared as follows:

The ester (1-13) is reacted with appropriate alkylating agent i.e., methyl iodide, in the presence of DMF and hydrogenated metal such as NaH to obtain dimethyl compound (7-1), and similar reactions to the steps ranging from 2nd step to $4^{th}$ step in Scheme 1 is further performed to produce the compound represented by general formula (II) having dimethyl group (7-4).

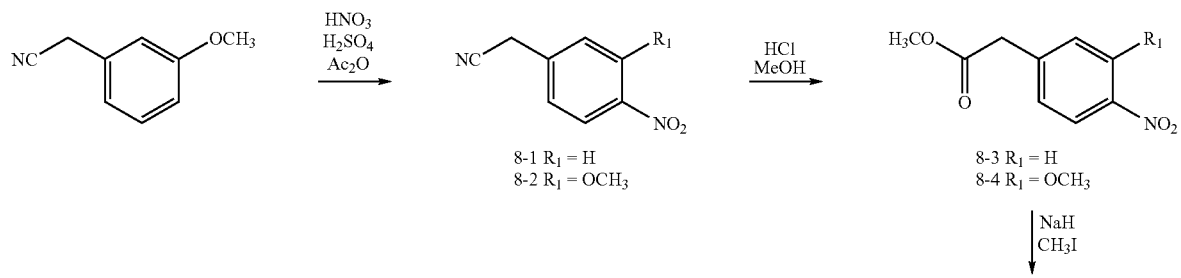

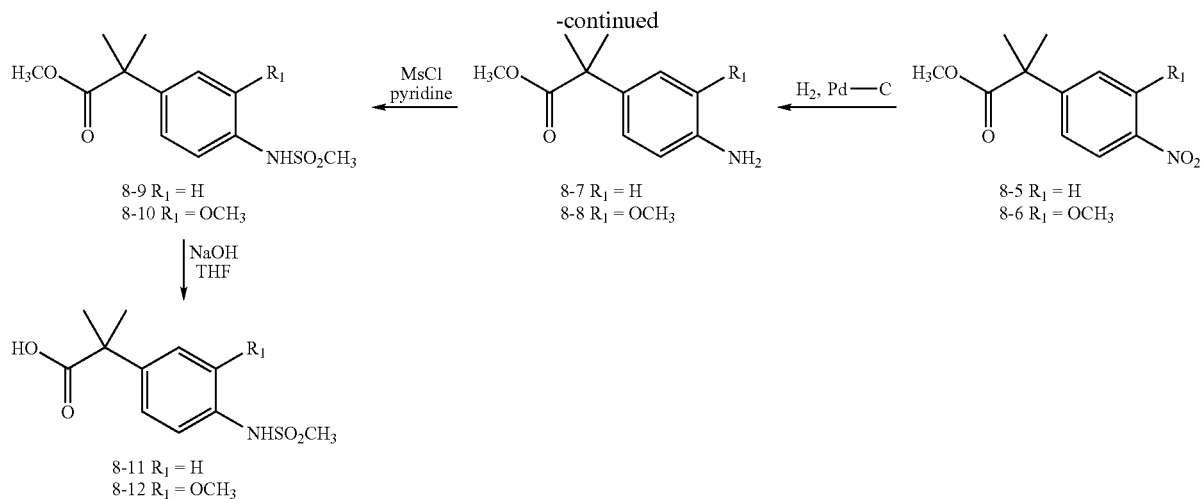

For example, the compound having lower alkoxy group or hydrogen atom at any of $R_1$ and $R_4$ and methyl groups at both of $R_5$ and $R_6$ can prepared by the procedure depicted in above Scheme 8.

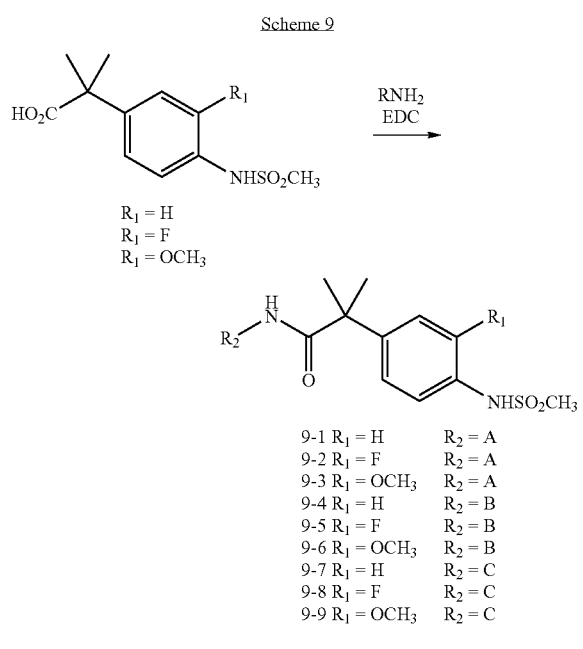

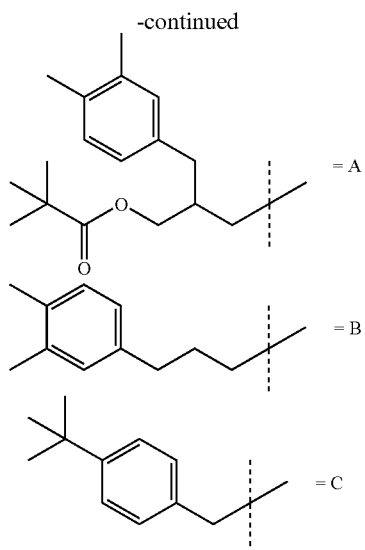

For example, the compound having NHCO group at A moiety and methyl groups at both of $R_5$ and $R_6$ can prepared by the procedure depicted in above Scheme 9.

As depicted in above Scheme 9, the carboxylic acid (8-11, 7-4, 8-12) is reacted with amine having appropriate B substituents in the presence of EDC to produce purposed compound represented by general formula (II) having NHCO group at B moiety.

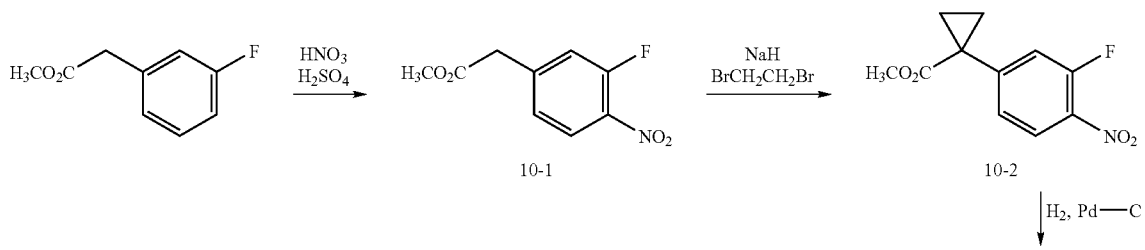

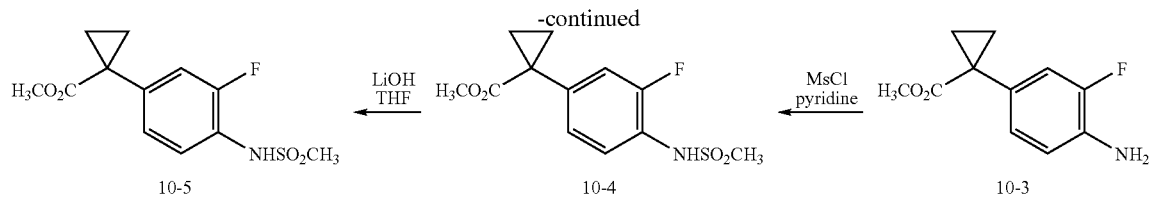

The compound represented by general formula (II) having cycloalkane at R$_5$ and R$_6$, and halogen atoms at any of R$_1$ and R$_4$ can prepared by the procedure depicted in Scheme 10.

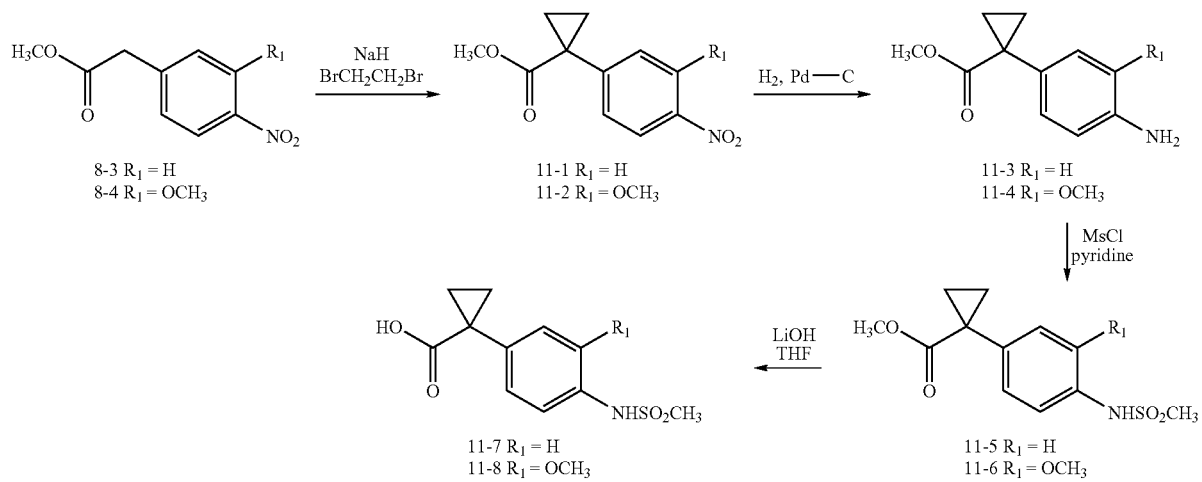

The compound represented by general formula (II) having cycloalkane at R$_5$ and R$_6$, and methoxyl group at any of R$_1$ and R$_4$ can prepared by the procedure depicted in Scheme 11.

For example, the ester (8-3. 8-4) is reacted with dihaloalkane reagent such as 1,2-dibromoethane in the presence of metal hydride such as NaH to produce cycloalkyl intermediates (11-1, 11-2) and serial steps comprising reduction, mesylation and alkylation reactions is performed to obtain final carboxylic acid product (11-7, 11-8).

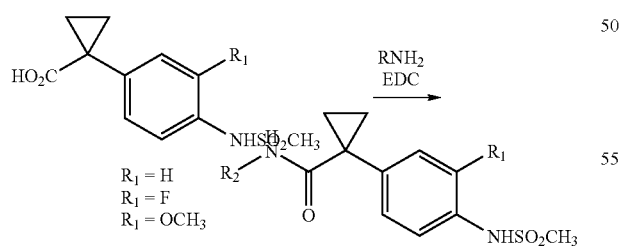

As depicted as Scheme 12, the carboxylic acid product (11-7, 11-8) is reacted with amine having appropriate B moiet in the presence of EDC to obtain final compound represented by general formula (II) having cycloalkyl group at R$_5$ and R$_6$.

The compound represented by general formula (III) and general formula (IV) having methyl group and hydrogen at R$_5$ and R$_6$, can prepared by the procedure depicted in Schemes 13 to 15.

Scheme 13

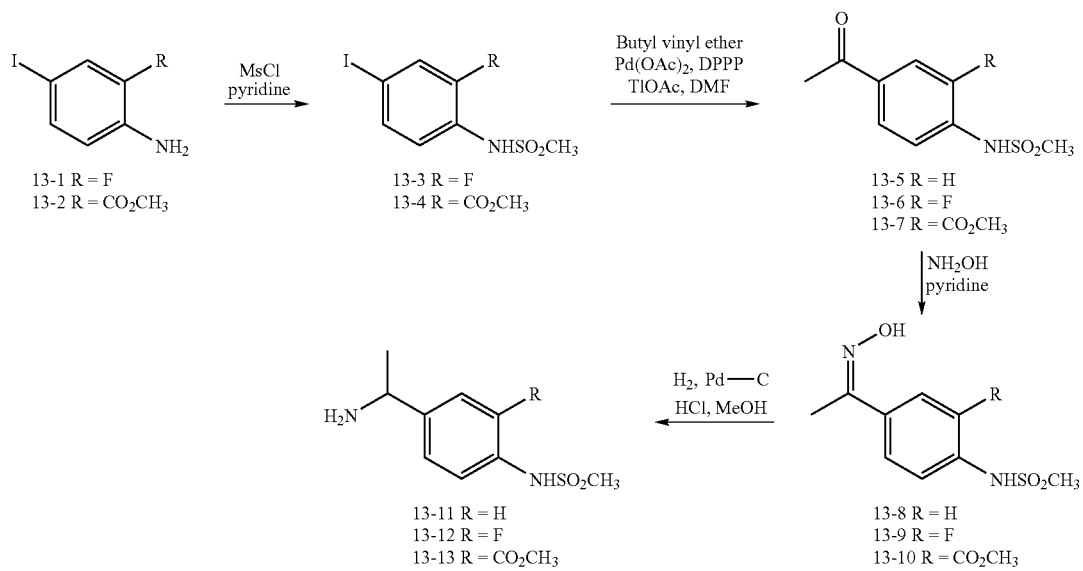

As depicted in above Scheme 13, the reaction consists of four steps as follows: at 1$^{st}$ step, the 4-iodo amine compound (13-1 to 13-2) dissolved in pyridine is reacted with a sulfonylating agent, e.g., methane sulfonyl chloride with stirring. The resulting organic solvent layer is extracted, dried, concentrated in vacuo and the residue is further purified with flash column chromatographic method to obtain sulfonyl amine compound (13-3 to 13-4) through the reducing amine to sulfonyl group; at 2$^{nd}$ step, the sulfonyl amine compound (13-3 to 13-4) dissolved in DMF is reacted with metal acetate, preferably, Pd (II) acetate or Tl (I) acetate, in the presence of DPPP (1,3-bisdiphenylphospinopropane) and butylvinylether at the temperature ranging from 60 to 110° C. in the period ranging from 5 to 24 hours and the reaction mixture is cooled at the temperature ranging from 0° C. to room temperature. Acidic solution such as 10%-HCl is added thereto and stirred. The reaction mixture is diluted with ethylacetate, washed with ammonium chloride solution, concentrated with vacuo and purified with flash column chromatographic method to obtain ketone compound (13-5 to 13-7); at 3$^{rd}$ step, the ketone compound and acid halide salt are dissolved in pyridine and heated at the temperature ranging from 40 to 90° C., preferably, 70° C., in the period ranging from 30 mins to 5 hours. The reaction mixture is cooled, diluted and the resulting organic layer is purified with flash column chromatographic method to obtain oxime derivatives (13-8 to 13-10) through substituting ketone with oxime group; at 4$^{th}$ step, the oxime derivatives is hydrogenated with reducing agent, for example, 10% Pd/c dissolved in lower alcohol e.g., methanol. The resultant is filtrated and the filtrate is purified with flash column chromatographic method to obtain amine intermediate compound (13-11 to 13-13) through reducing nitro group to amine group as can be seen in Scheme 13.

Scheme 14

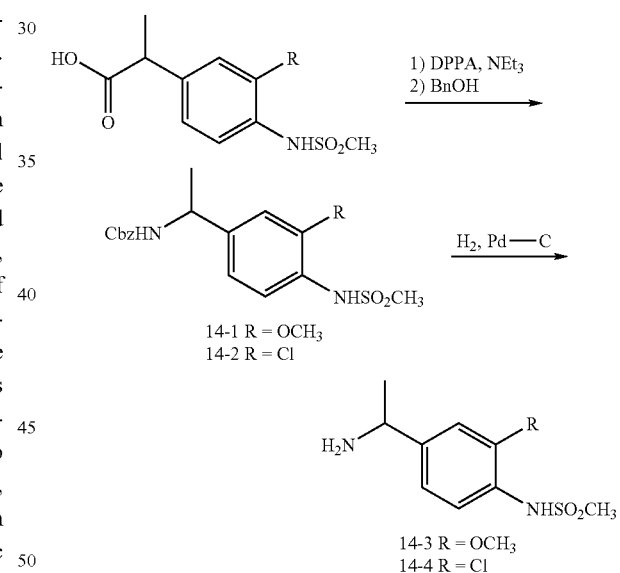

The compound having chloro group or methoxyl group at any of $R_1$ to $R_4$, can prepared by the procedure depicted in Scheme 14.

Scheme 15

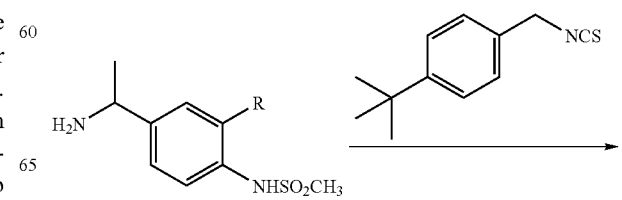

-continued

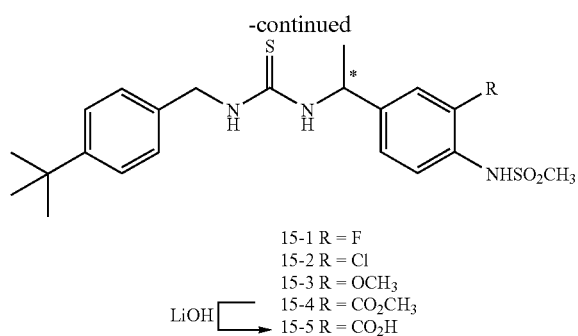

15-1 R = F
15-2 R = Cl
15-3 R = OCH₃
15-4 R = CO₂CH₃
15-5 R = CO₂H

The thiourea compound represented by general formula (II) and urea compound general formula (IV) can prepared by the procedure depicted in Scheme-15.

As depicted as Scheme 15, the amine compound obtained in Scheme 14 and isothiocyanate compound (B—NCS) or cyanate compound (B—NCO) having appropriate B moiety is dissolved in DMF and stirred at the temperature ranging from 0° C. to room temperature, in the period ranging from 30 mins to 4 hours, preferably, 2 hours. The reaction mixture is diluted with water and the organic solvent layer is extracted, dried, concentrated in vacuo and purified with flash column chromatographic method to obtain purposed thiourea compound or urea compounds (15-1 to 15-5, 18-1 to 18-6, 19-5 to 19-12, 23-1 to 23-2) through coupling reaction.

Scheme 16

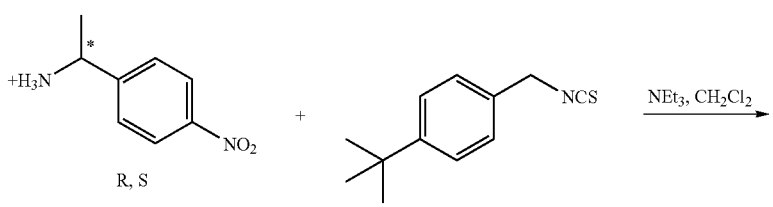

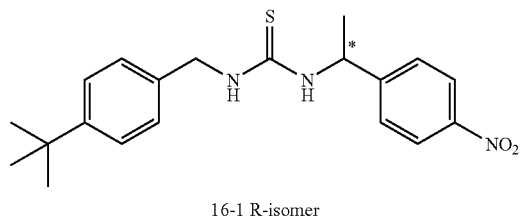

16-1 R-isomer
16-2 S-isomer

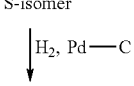

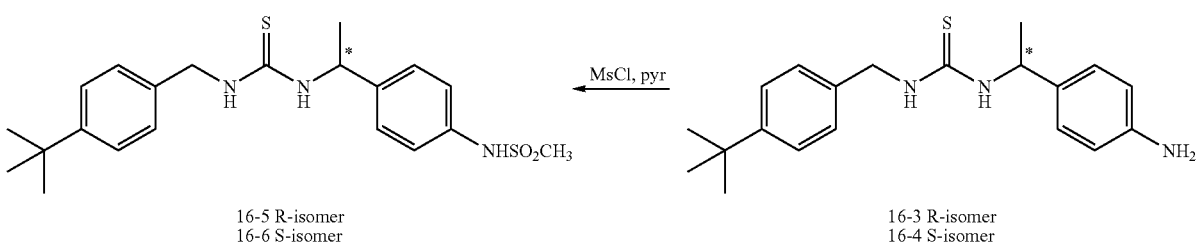

16-5 R-isomer
16-6 S-isomer 16-3 R-isomer
16-4 S-isomer

The stereoisomers of the compound represented by general formula (III) and general formula (IV) having hydrogen atoms at all the $R_1$ to $R_4$, can prepared by the procedure depicted in Scheme 16
Scheme 17
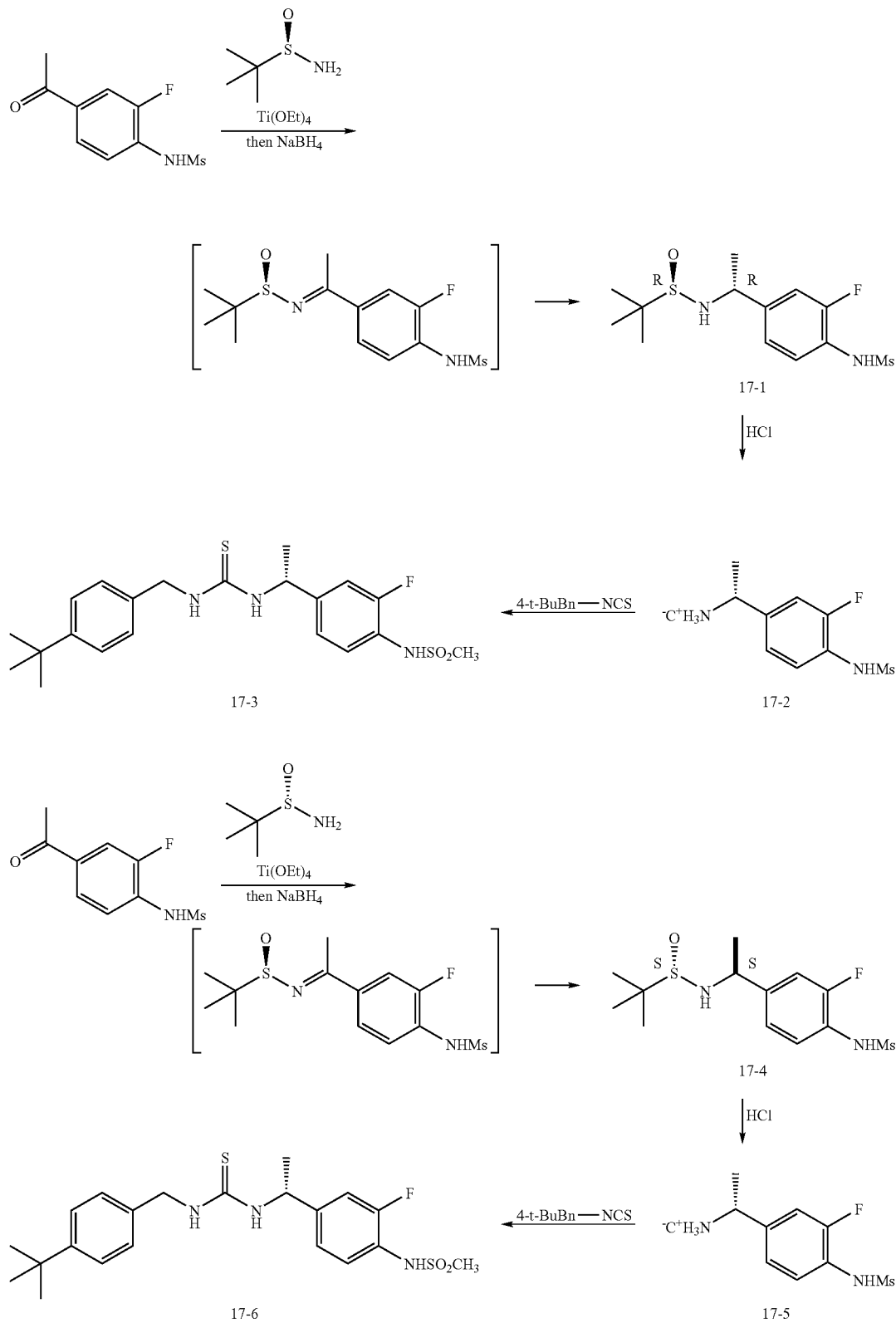

The stereoisomers of the compound represented by general formula (III) and general formula (IV) having halogen atom at any of $R_1$ to $R_4$, can prepared by the procedure depicted in Schemes 17 and 18.

As depicted in above Scheme 17, 3'-fluoro-4(methylsulfonylamino)acetophenone is coupled with optically active R form or S form sulfone amine respectively and reduced with reducing agent such as $NaBH_4$ to synthesize R form or S form sulfone amine isomers (17-1 and 17-4) respectively. The amine isomers is further hydrolyzed in acidic condition to obtain optically active amine (17-2, 17-5).

The procedure similar to the methods in Scheme 13 is performed to obtain optically active (R) or (S) thiourea represented by general formula (III) or urea represented by general formula (IV) (17-3 and 17-6).

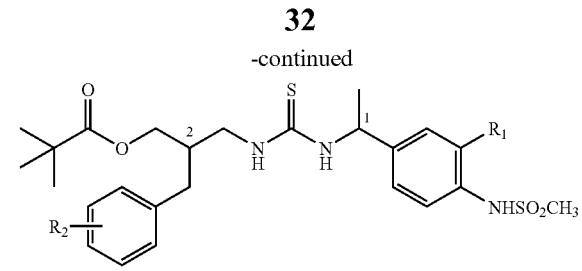

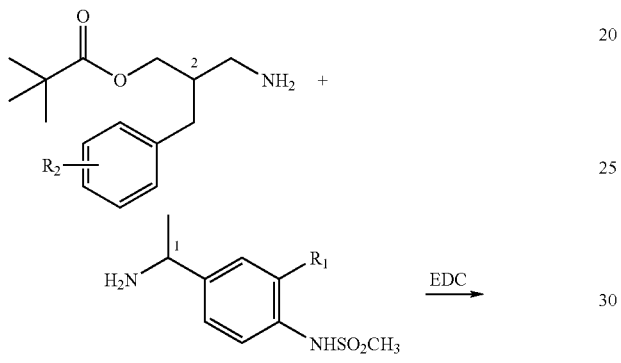

| | | | |
|---|---|---|---|
| 18-1 | 1R, 2R | $R_1 = H$ | $R_2 = H$ |
| 18-2 | 1R, 2S | $R_1 = H$ | $R_2 = H$ |
| 18-3 | 1S, 2R | $R_1 = H$ | $R_2 = H$ |
| 18-4 | 1S, 2S | $R_1 = H$ | $R_2 = H$ |
| 18-5 | mixture | $R_1 = H$ | $R_2 = 3,4\text{-Me}_2$ |
| 18-6 | 1R | $R_1 = H$ | $R_2 = 3,4\text{-Me}_2$ |
| 18-7 | 1R, 2R | $R_1 = H$ | $R_2 = 3,4\text{-Me}_2$ |
| 18-8 | 1R, 2S | $R_1 = H$ | $R_2 = 3,4\text{-Me}_2$ |
| 18-9 | mixture | $R_1 = H$ | $R_2 = 3,4\text{-Me}_2$ |
| 18-10 | 1R | $R_1 = H$ | $R_2 = 4\text{-t-Bu}$ |
| 18-11 | 1R, 2R | $R_1 = H$ | $R_2 = 4\text{-t-Bu}$ |
| 18-12 | 1R, 2S | $R_1 = H$ | $R_2 = 4\text{-t-Bu}$ |
| 18-13 | mixture | $R_1 = H$ | $R_2 = 4\text{-t-Bu}$ |
| 18-14 | mixture | $R_1 = H$ | $R_2 = 4\text{-t-Bu}$ |
| | | $R_1 = F$ | $R_2 = 3,4\text{-Me}_2$ |
| | | $R_1 = F$ | $R_2 = 4\text{-t-Bu}$ |

As depicted as Scheme 18, the amine is reacted with benzyl amine in the presence of EDC to obtain final thiourea compound represented by general formula (II) having (I-2) group at B moiety.

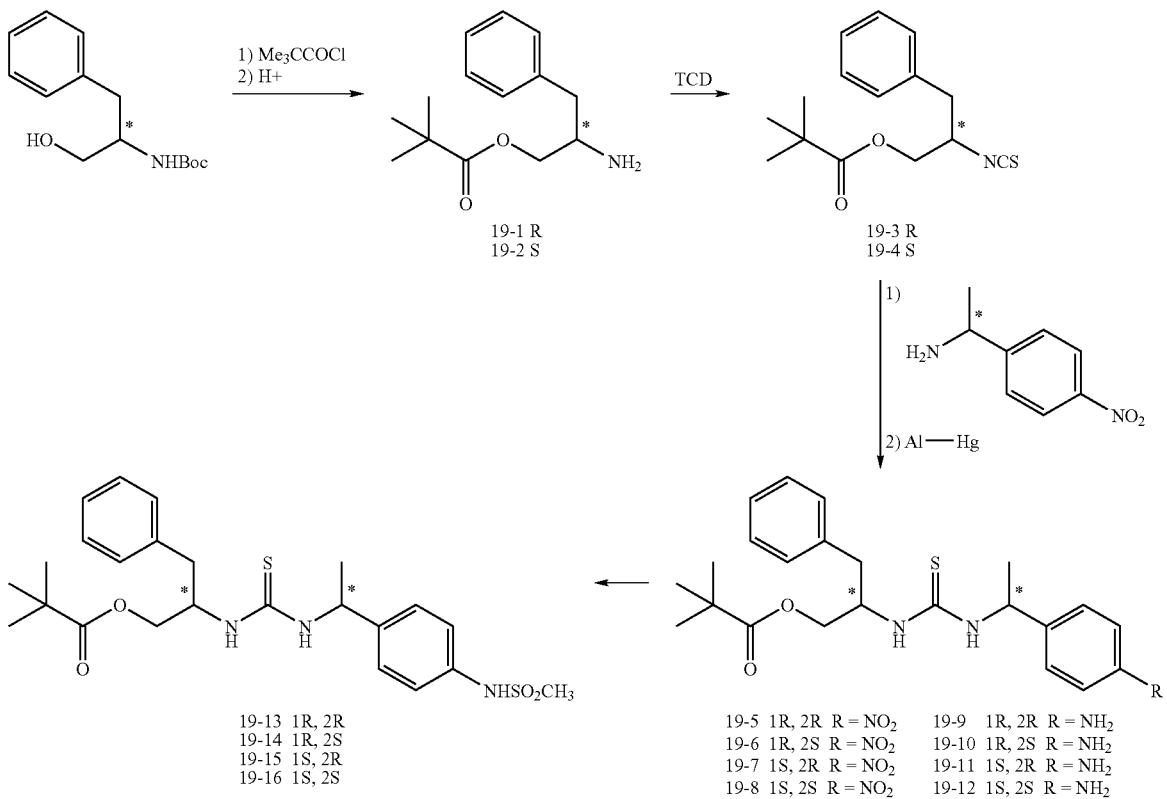

As depicted in above Scheme 19, the alcohol is reacted with pivaloyl halide, e.g., pivaloyl chloride (Me₃CCOCl) in acidic condition to obtain amine (19-1 and 19-2). The mine is further reacted with 1,1-thiocarbonyl diimidazole (TCD) in the presence of DMF solvent to produce isothiocyanate (19-3, 19-4). The isocyanate is reacted with (R) or (S) alpha-methyl-4-nitrobenzyl amine HCl in the presence of base e.g., TEA, reduced with reducing agent, for example, Al—Hg and mesylated to obtain (1S, 2R), (1S, 2S), (1R, 2R) and (1R, 2S) thiourea represented by general formula (III) or urea represented by general formula (IV) (19-13 to 19-16).

The amine intermediate compound (13-11 to 13-13) can be prepared by the procedure depicted in following Scheme 20.

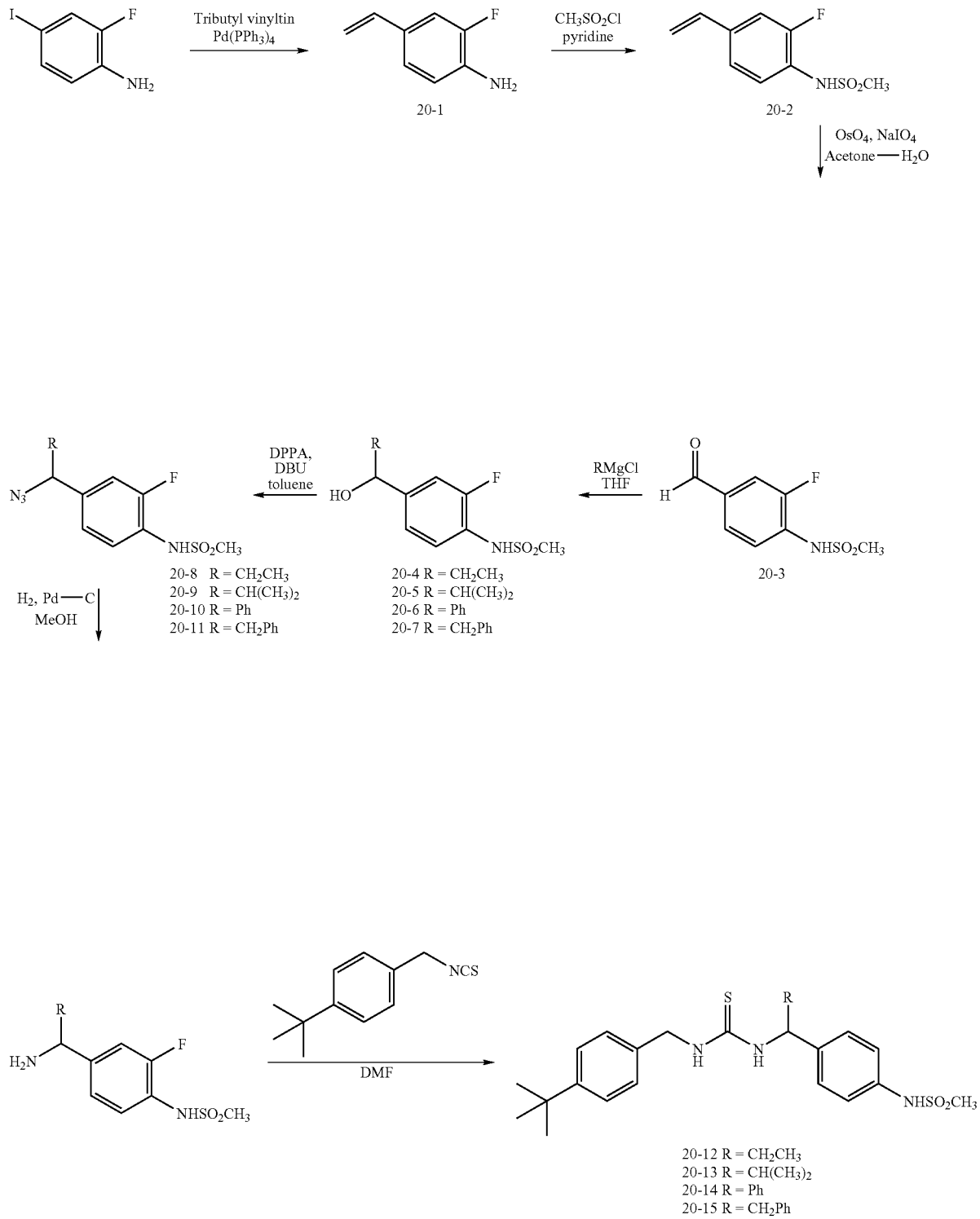

As depicted in above Scheme 20, 2-fluoro-4-iodoaniline is reacted with tertakis(triphenylphosphine)palladium and tributylvinyltin in the presence with catalitically amount of 2,6-di-tert-butyl-4-methylphenol to obtain 2-fluoro-4-vinylaniline (21-1). The resulting compound is reacted with sulfonylating agent such as methane sulfonyl chloride in the presence of pyridine solvent to produce N-(2-fluoro-4-vinylphenyl)methanesulfoneamide (20-2) and oxidized with oxidizing agent e.g., osmium tetroxide and sodium periodate in the presence of acetone-water mixture solvent to aldehyde intermediate (20-3). The aldehyde compound is reacted with Grignard reagent to obtain alcohol intermediate (2-4 to 20-7) and further reacted with DPPA (diphenylphosphorylazide) and DBU (1,8-diazabicyclo[5,4,0]undec-7-ene) in the presence with toluene solvent to produce azide compound (20-8 to 20-11). The azide intermediate is finally reduced with reducing agent such as Pd/C to produce purposed amine derivative (13-11 t 13-13) selectively.

The thiourea compound represented by general formula (III) or urea compound represented by general formula (IV) having methyl groups at both $R_5$ and $R_6$ can be prepared by the procedure shown in following Scheme 21.

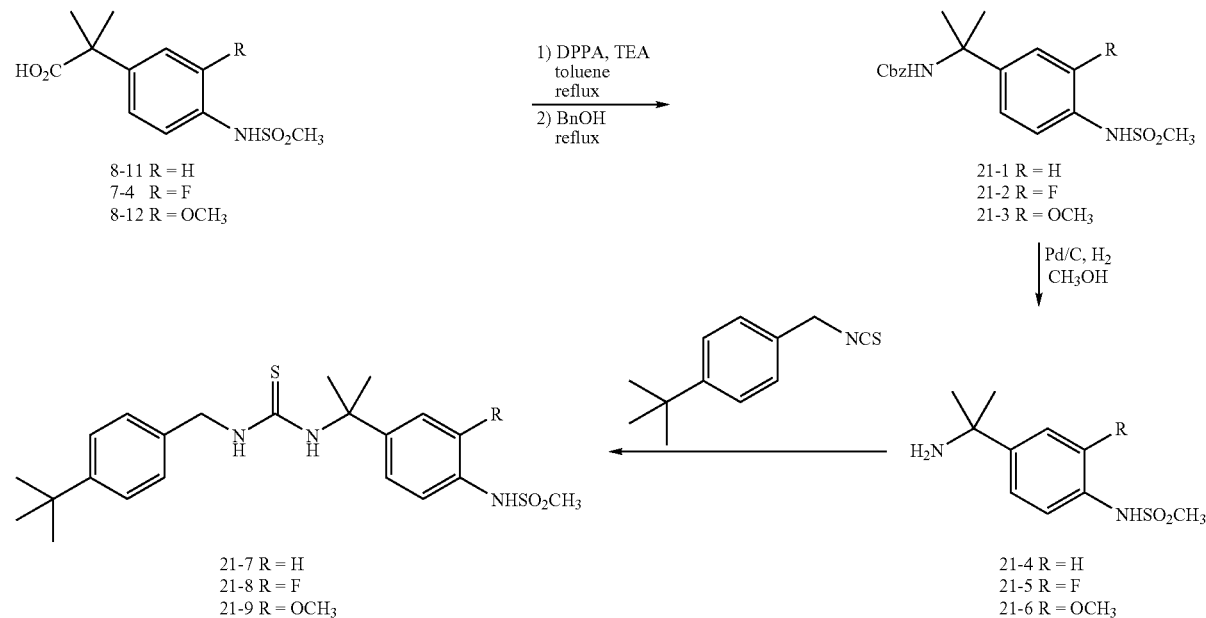

As depicted as Scheme 21, the carboxylic acid compound (8-11, 7-4, 8-12) is reacted with DDDPA (diphenylphosphorylazide) and molecular sieve in the presence with base such as TEA and organic solvent and benzyl alcohol is added to the reaction mixture to obtain carbamate (21-1 to 21-3) through Curtius reaction. The carbamates compound is subjected to reduction process with reducing agent such as Pd/C in $H_2$ gas to obtain amine intermediate (21-4 to 21-6) and coupling reaction shown in Scheme 15 is further subjected to obtain purposed amine is reacted with benzyl amine in the presence of EDC to obtain final thiourea compound represented by general formula (III) or urea compound represented by general formula (IV).

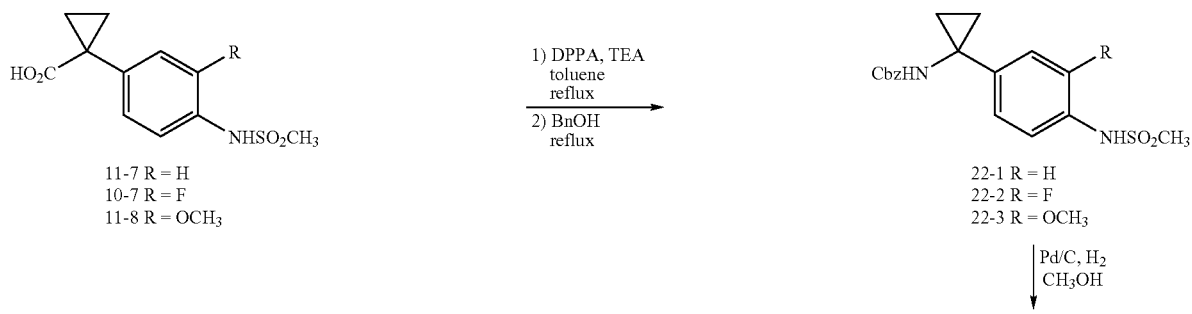

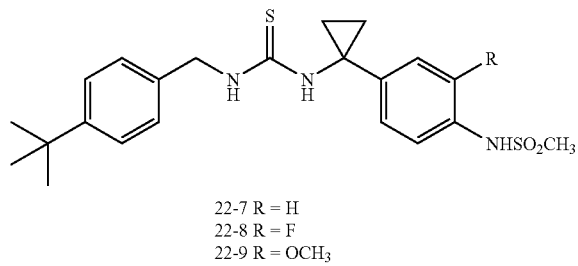

22-7 R = H
22-8 R = F
22-9 R = OCH₃

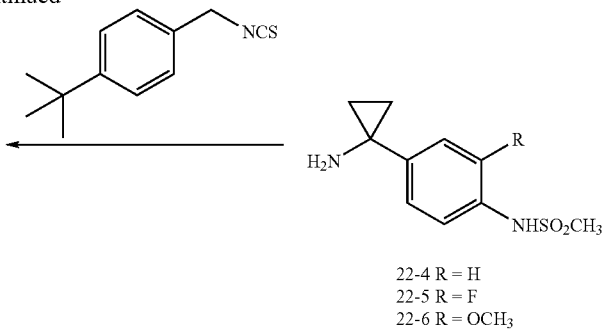

22-4 R = H
22-5 R = F
22-6 R = OCH₃

The thiourea compound represented by general formula (III) or urea compound represented by general formula (IV) having cyclopropyl group at R₅ and R₆ can be prepared by the procedure shown in Scheme 22.

As depicted as Scheme 22, the carboxylic acid compound (8-11, 7-4, 8-12) is reacted with DDDPA (diphenylphosphorylazide) and molecular sieve in the presence with base such as TEA and organic solvent and benzyl alcohol is added to the reaction mixture to obtain carbamate (21-1 to 21-3) through Curtius reaction. The carbamates compound is subjected to reduction process with reducing agent such as Pd/C in H₂ gas to obtain amine intermediate (21-4 to 21-6) and coupling reaction shown in Scheme 15 is further subjected to obtain purposed amine is reacted with benzyl amine in the presence of EDC to obtain final thiourea compound represented by general formula (III) or urea compound represented by general formula (IV).

Scheme 23

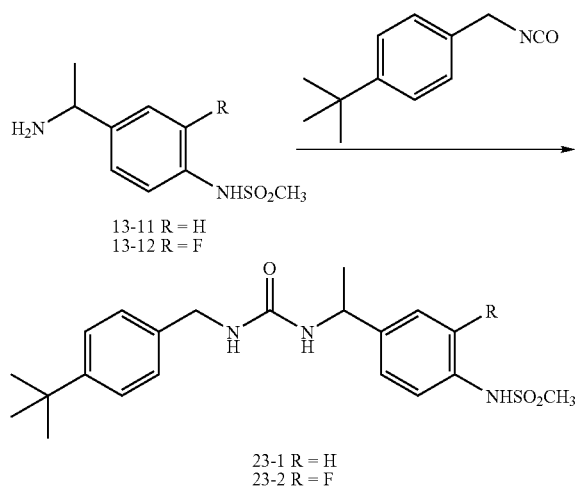

23-1 R = H
23-2 R = F

The urea compound represented by general formula (IV) having methyl or hydrogen at R₅ and R₆ can be prepared by the procedure shown in Scheme 23.

The present invention also provides a pharmaceutical composition comprising a compound of formula (I) to (V) or a pharmaceutically acceptable salt thereof as an active ingredient for an antagonist of vanilloid receptor.

The compound of formula (I) to (V) according to the present invention has potent analgesic and anti-inflammatory activity, and the pharmaceutical composition of the present invention thus may be employed to alleviate or relieve acute, chronic or inflammatory pains or to suppress inflammation and to treat urgent urinary incontinence.

The present invention also provides a pharmaceutical composition comprising the compound selected from the group consisting of compounds of formula (I) to (V) or the pharmaceutical acceptable salts thereof for preventing and treating pain diseases or inflammatory diseases.

Pain diseases or inflammatory diseases comprise at least one selected from the group consisting of pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease and the like.

The present invention also provides a pharmaceutical composition comprising the compound selected from the group consisting of compounds of formula (I) to (V) or the pharmaceutical acceptable salts thereof for preventing and treating urgent urinary incontinence.

The pharmaceutical composition of the present invention comprises the inventive compounds between 0.0001 to 10% by weight, preferably 0.0001 to 1% by weight based on the total weight of the composition.

The present invention also provides an use of compound selected from the group consisting of compounds of formula (I) to (V) or the pharmaceutical acceptable salts thereof as antagonists of vanilloid receptors.

In accordance with another aspect of the present invention, there is also provided an use of the compound (I) to (V) for manufacture of medicines employed for alleviating or treating pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease, inflammatory disease or urgent urinary incontinence.

The compound of formula (I) to (V) according to the present invention can be provided as a pharmaceutical composition comprising pharmaceutically acceptable carriers, adjuvants or diluents. For example, the compounds of the present invention can be dissolved in oils, propylene glycol or other solvents, which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

In accordance with another aspect of the present invention, there is also provided an method of alleviating or treating pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease, inflammatory disease or urgent urinary incontinence, wherein the method comprises administering a therapeutically effective amount of the compound of formula of (I) to (V) or the pharmaceutically acceptable salt thereof.

Hereinafter, the following formulation methods and excipients are merely exemplary and in no way limit the invention.

The compounds of the present invention in pharmaceutical dosage forms may be used in the form of their pharmaceutically acceptable salts, and also may be used alone or in appropriate association, as well as in combination with other pharmaceutically active compounds.

The compounds of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the inventive compounds varies depending on the condition and the weight of the subject, severity, drug form, route and period of administration, and may be chosen by those skilled in the art. However, in order to obtain desirable effects, it is generally recommended to administer at the amount ranging 0.0001-100 mg/kg, preferably 0.001-100 mg/kg by weight/day of the inventive compounds of the present invention. The dose may be administered in single or divided into several times per day. In terms of composition, the compounds should be present between 0.0001 to 10% by weight, preferably 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intrathecal, epidural or intracerebroventricular injection.

It is another object of the present invention to provide a use of the above-mentioned compound of the present invention for the preparation of therapeutic agent for the preventing and treating pain disease or inflammatory disease by showing vanilloid receptor-antagonistic activity in human or mammal.

Additionally, it is an object of the present invention to provide a method of treating or preventing pain disease and inflammatory disease by showing vanilloid receptor-antagonistic activity in a mammal comprising administering to said mammal an effective amount of the above-mentioned compound of the present invention together with a pharmaceutically acceptable carrier thereof.

It will be apparent to those skilled in the art that various modifications and variations can be made in the compositions, use and preparations of the present invention without departing from the spirit or scope of the invention.

BEST MODE FOR CARRYING OUT THE INVENTION

The present invention is more specifically explained by the following examples. However, it should be understood that the present invention is not limited to these examples in any manner.

EXAMPLES

Example 1

Preparation of N-(4-tert-butylbenzyl)-2-[3-fluoro-4-(metylsulfonylamino)phenyl]propionamide (1-51, KJ-372)

Step 1-1. Preparation of ethyl 2-(3-fluoro-4-nitrophenylpropionate (1-1, SU-654)

To a stirred solution of potassium t-butoxide (20 mmol) in DMF (20 mL) was added a mixture of 2-fluoro-nitrobenzene (10 mmol) and ethyl-2-chloropropionate (10 mmol) at 0° C. dropwise. After being stirred for 10 min at 0° C., the mixture was quenched by 1 N HCl solution, diluted with water and extracted with diethyl ether several times. The combined organic layers were washed with water and brine, dried over $MgSO_4$, and concentrated in vacuo. The residue was purified by flash column chromatography on silica gel using EtOAc: hexanes (1:10) as eluant to afford ethyl 2-(3-fluoro-4-nitrophenyl)propionate (1-1, SU-654).

68% yield, yellow oil $^1$H NMR (CDCl$_3$) δ 8.02 (dd, 1H, J=7.8, 8.0 Hz), 7.2-7.3 (m, 2H), 4.14 (m, 2H), 3.78 (q, 1H, J=7.1 Hz), 1.52 (d, 3H, J=7.1 Hz), 1.22 (t, 3H, J=7.08 Hz)

Step 1-2. Preparation of ethyl 2-(4-amino-3-fluorophenyl)propionate (1-13, SU-656)

A suspension of 2-(3-fluoro-4-nitrophenyl)propionate (1-1, 5 mmol) and 10% Pd—C (500 mg) in EtOH (30 mL) was hydrogenated under a balloon of hydrogen for 1 h and filtered through Celite. The filtrate was concentrated in vacuo and the residue was purified by flash column chromatography on silica gel using EtOAc:hexanes (1:4) as eluant to afford 2-(4-amino-3-fluorophenyl)propionate compound (1-13, SU-656).

94% yield, a colorless oil $^1$H NMR (CDCl$_3$) δ 6.96 (dd, 1H, J=1.7 Hz), 6.87 (dd, 1H, J=1.7, 8.3 Hz), 6.71 (dd, 1H, J=8.3, 11.9 Hz), 4.11 (m, 2H), 3.58 (q, 1H, J=7.1 Hz), 3.45 (bs, 2H), 1.43 (d, 3H, J=7.1 Hz), 1.20 (t, 3H, J=7.05 Hz)

Step 1-3. Preparation of ethyl 2-[3-fluoro-4-(methylsulfonylamino)phenyl]propionate compound (1-26, SU-658)

A solution of 2-(4-amino-3-fluorophenyl)propionate (1-13, 4 mM) and pyridine (10 ml) was dissoluted with methansulfonylchloride (6 mM) and was stirred at 0° C. for 10 minutes. The combined organic layers were washed with $H_2O$ and residue was purified by flash column chromatography on silica gel with EtOAc/hexanes (1:2) as eluant to afford ethyl 2-[3-fluoro-4-(metylsulfonylamino)phenyl]propionate compound (1-26, SU-658).

91% yield, white solid mp=81° C.

¹H NMR (CDCl₃) δ 7.50 (t, 1H, J=8.3 Hz), 7.0-7.1 (m, 2H), 6.55 (bs, 1H), 4.12 (m, 2H), 3.68 (q, 1H, J=7.1 Hz), 3.02 (s, 3H), 1.48 (d, 3H, J=7.1 Hz), 1.22 (t, 3H, J=7.1 Hz)

Step 1-4. Preparation of 2-[3-fluoro-4-(metylsulfonylamino)phenyl]propion acid compound (1-38, SU-660)

A solution of ethyl 2-[3-fluoro-4-(metylsulfonylamino)phenyl]propionate (1-26, 2 mmol) in H₂O and THF (1:2, 30 mL) was treated with lithium hydroxide (6 mmol) and stirred for 4 h at room temperature. The mixture was diluted with H₂O and CH₂Cl₂, acidified by 1 N HCl solution and extracted with CH₂Cl₂ several times. The combined organic layers were washed with water and brine, dried over MgSO₄ and concentrated in vacuo. The residue was crystallized by diethyl ether and n-hexane to afford 2-[3-fluoro-4-(metylsulfonylamino)phenyl]propion acid compound (1-38, SU-660)

97% yield, white solid, mp=120° C.

¹H NMR (CDCl₃) δ 7.52 (t, 1H, J=8.04 Hz), 7.1-7.15 (m, 2H), 6.60 (bs, 1H), 3.73 (q, 1H, J=7.1 Hz), 3.03 (s, 3H), 1.51 (d, 3H, J=7.1 Hz)

Step 1-5. Preparation of N-(4-tert-Butylbenzyl)-2-[3-fluoro-4-(methylsulfonylamino)phenyl]propionamide (1-51, KMJ-372)

A mixture consisting of 2-[3-Fluoro-4-(methylsulfonylamino)phenyl]propionic acid (1-38, 10 mmol), 4-t-butylbenzylamine (12 mmol) and EDC (12 mmol) in CH₂Cl₂ (20 mL) was stirred for 12 h at room temperature. The reaction mixture was filtered off and the filtrate was concentrated. the residue was purified by flash column chromatography on silica gel using EtOAc:hexanes as eluant to obtain N-(4-tert-butylbenzyl)-2-[3-fluoro-4-(metylsulfonylamino)phenyl]propionamide (1-51, KMJ-372) having following physicochemical properties:

78% yield, white solid, mp=52-54° C.

¹H NMR (CDCl₃) δ 7.48 (t, 1H, J=8.3 Hz), 7.32 (bd, 2H), 7.1-7.2 (m, 4H), 6.73 (bs, 1H), 5.83 (bt, 1H), 4.36 (ddd of AB, 2H), 3.52 (q, 1H, J=7.1 Hz), 3.00 (s, 3H), 1.50 (d, 3H, J=7.1 Hz), 1.29 (s, 9H)

MS (FAB) m/z 407 (MH⁺)

Example 2

Preparation of N-(4-tert-Butylbenzyl)-2-[3-chloro-4-(methylsulfonylamino)phenyl]propionamide (1-52 KMJ-470)

Through similar procedure to that in Example 1 excepting using 2-chloro-nitrobenzene as a starting material, N-(4-tert-Butylbenzyl)-2-[3-chloro-4-(methylsulfonylamino)phenyl] propionamide having following physicochemical properties was synthesized:

68% yield, white solid, mp=126-129° C.

¹H NMR (CDCl₃) δ 7.60 (d, 1H, J=8.2 Hz), 7.43 (d, 1H, J=2 Hz), 7.34 (bd, 2H), 7.24 (dd, 1H, J=8.2, 2 Hz), 7.14 (bd, 2H), 6.75 (bs, 1H), 5.68 (bt, 1H), 4.38 (ddd of AB, 2H), 3.50 (q, 1H, J=7.1 Hz), 3.01 (s, 3H), 1.52 (d, 3H, J=7.1 Hz), 1.30 (s, 9H)

MS (AB) m/z 423 (MH⁺)

Example 3

Preparation of N-(4-tert-Butylbenzyl)-2-[3-bromo-4-(methylsulfonylamino)phenyl]propionamide (1-53 SH-173)

Through similar procedure to that in Example 1 excepting using 2-bromo-nitrobenzene as a starting material, N-(4-tert-Butylbenzyl)-2-[3-bromo-4-(methylsulfonylamino)phenyl] propionamide having following physicochemical properties was synthesized:

76% yield, white solid, mp=66-67° C.

¹H NMR (CDCl₃) δ 7.55-7.6 (m, 2H), 7.33 (d, 2H, J=8.1 Hz), 7.27 (dd, 1H, J=1.8, 8.6 Hz), 7.12 (d, 2H, J=8.1 Hz), 6.80 (bs, 1H), 5.91 (bt, 1H), 4.36 (ddd of AB, 2H), 3.50 (q, 1H, J=7.1 Hz), 2.98 (s, 3H), 1.50 (d, 3H, J=7.1 Hz), 1.29 (s, 9H)

MS (FAB) m/z 467 (MH⁺)

Example 4

Preparation of N-(4-tert-Butylbenzyl)-2-[3-iodo-4-(methylsulfonylamino)phenyl]propionamide (1-54 SH-168)

Through similar procedure to that in Example 1 excepting using 2-iodo-nitrobenzene as a starting material, N-(4-tert-Butylbenzyl)-2-[3-iodo-4-(methylsulfonylamino)phenyl] propionamide having following physicochemical properties was synthesized:

75% yield, white solid, mp=71° C.

¹H NMR (CDCl₃) δ 7.80 (d, 1H, J=2 Hz), 7.59 (d, 1H, J=8.3 Hz), 7.3-7.37 (m, 3H), 7.13 (d, 2H, J=8.1 Hz), 6.60 (bs, 1H), 5.67 (bt, 1H), 4.39 (ddd of AB, 2H), 3.48 (q, 1H, J=7.1 Hz), 3.01 (s, 3H), 1.52 (d, 3H, J=7.1 Hz), 1.30 (s, 9H)

MS (FAB) m/z 515 (MH⁺)

Example 5

Preparation of N-(4-tert-Butylbenzyl)-2-[3,5-difluoro-4-(methylsulfonylamino)phenyl]propionamide (1-55 SH-285)

Through similar procedure to that in Example 1 excepting using 2,6-difluoronitrobenzene as a starting material, N-(4-tert-Butylbenzyl)-2-[3,5-difluoro-4-(methylsulfonylamino) phenyl]propionamide having following physicochemical properties was synthesized:

70% yield, white solid, mp=80-81° C.

¹H NMR (CDCl₃) δ 7.35 (dt, 2H), 7.15 (bd, 2H), 6.99 (dt, 2H), 6.16 (bs, 1H), 5.76 (bt, 1H), 4.38 (ddd of AB, 2H), 4.12 (q, 1H, J=7.1 Hz), 3.02 (s, 3H), 1.50 (d, 3H, J=7.1 Hz), 1.30 (s, 9H)

MS (FAB) m/z 425 (MH⁺)

Example 6

Preparation of N-(4-tert-Butylbenzyl)-2-[3-cyano-4-(methylsulfonylamino)phenyl]propionamide (1-56 SH-219)

Through similar procedure to that in Example 1 excepting using 2-cyano-nitrobenzene as a starting material, N-(4-tert- Butylbenzyl)-2-[3-cyano-4-(methylsulfonylamino)phenyl] propionamide having following physicochemical properties was synthesized:

30% yield, white solid, mp=102-105° C.

$^1$H NMR (CDCl$_3$) δ 7.67 (d, 1H, J=8.4 Hz), 7.63 (d, 1H, J=1.8 Hz), 7.58 (dd, 1H), 7.35 (bd, 2H), 7.15 (bd, 2H), 5.73 (bt, 1H), 4.38 (ddd of AB, 2H), 3.51 (q, 1H, J=7.1 Hz), 3.11 (s, 3H), 1.53 (d, 3H, J=7.1 Hz), 1.31 (s, 9H)

MS (FAB) m/z 414 (MH$^+$)

Example 7

Preparation of N-(4-tert-Butylbenzyl)-2-[3-(t-butoxycarbonyl)-4-(methylsulfonylamino)phenyl]propionamide (1-57 KMJ-806)

Through similar procedure to that in Example 1 excepting using 2-tert-butoxycarbonyl-nitrobenzene as a starting material, N-(4-tert-Butylbenzyl)-2-[3-(t-butoxycarbonyl)-4-(methylsulfonylamino)phenyl]propionamide having following physicochemical properties was synthesized:

53% yield, white solid, mp=75-77° C.

$^1$H NMR (CDCl$_3$) δ 7.90 (d, 1H, J=2.2 Hz), 7.67 (d, 1H, J=8.6 Hz), 7.50 (dd, 1H, J=8.6, 2.2 Hz), 7.33 (bd, 2H), 7.13 (bd, 2H), 5.74 (bt, 1H), 4.38 (ddd of AB, 2H), 3.55 (q, 1H, J=7.1 Hz), 3.04 (s, 3H), 1.60 (s, 9H), 1.53 (d, 3H, J=7.1 Hz), 1.30 (s, 9H)

MS (FAB) m/z 489 (MH$^+$)

Example 8

Preparation of N-(4-tert-Butylbenzyl)-2-[3-carboxyl-4-(methylsulfonylamino)phenyl]propionamide (1-58 KMJ-788)

The compound 1-58 was prepared from N-(4-tert-Butylbenzyl)-2-[3-(t-butoxycarbonyl)-4-(methylsulfonylamino) phenyl]propionamide (1-57) by trifluoro acid hydrolysis.

74% yield, white solid, mp=180-183° C.

$^1$H NMR (CD$_3$OD) δ 8.45 (bt, 1H), 8.12 (d, 1H, J=2.2 Hz), 7.64 (d, 1H, J=8.6 Hz), 7.56 (dd, 1H, J=8.6, 2.2 Hz), 7.30 (bd, 2H), 7.11 (bd, 2H), 4.29 (bs, 2H), 3.69 (q, 1H, J=7.1 Hz), 3.04 (s, 3H), 1.46 (d, 3H, J=7.1 Hz), 1.27 (s, 9H)

MS (FAB) m/z 433 (MH$^+$)

Example 9

Preparation of N-(4-tert-Butylbenzyl)-2-[3-(methoxycarbonyl)-4-(methylsulfonylamino)phenyl]propionamide (1-59 KMJ-838)

Through similar procedure to that in Example 1 excepting using 2-methoxycarbonyl-nitrobenzene as a starting material, N-(4-tert-Butylbenzyl)-2-[3-(methoxycarbonyl)-4-(methylsulfonylamino)phenyl]propionamide (1-59) having following physicochemical properties was synthesized:

79% yield, white solid, mp=142-144° C.

$^1$H NMR (CDCl$_3$) δ 10.38 (s, 1H), 8.03 (d, 1H, J=2.2 Hz), 7.70 (d, 1H, J=8.6 Hz), 7.51 (dd, 1H, J=8.6, 2.2 Hz), 7.33 (bd, 2H), 7.13 (bd, 2H), 5.69 (bt, 1H), 4.38 (ddd of AB, 2H), 3.94 (s, 3H), 3.53 (q, 1H, J=7.1 Hz), 3.05 (s, 3H), 1.54 (d, 3H, J=7.1 Hz), 1.30 (s, 9H)

MS (FAB) m/z 447 (f)

Example 10

Preparation of N-(4-tert-Butylbenzyl)-2-[3-(benzylamino)carbonyl-4-(methylsulfonylamino)phenyl] propionamide (1-60, J-836)

N-(4-tert-Butylbenzyl)-2-[3-(benzylamino)carbonyl-4-(methylsulfonylamino)phenyl]propionamide (1-60) was prepared from 1-58 by general amino coupling with benzyl amine.

88% yield, white solid, mp=79-81° C.

$^1$H NMR (CDCl$_3$) δ 7.65 (d, 1H, J=8.6 Hz), 7.61 (d, 1H, J=2.2 Hz), 7.3-7.38 (m, 8H), 7.11 (bd, 2H), 5.84 (bt, 1H), 4.60 (d, 2H, J=6 Hz), 4.35 (ddd of AB, 2H), 3.48 (q, 1H, J=7.1 Hz), 2.97 (s, 3H), 1.50 (d, 3H, J=7.1 Hz), 1.29 (s, 9H)

MS (FAB) m/z 522 (MH$^+$)

Example 11

Preparation of N-(4-tert-Butylbenzyl)-2-[3-piperidino-4-(methylsulfonylamino)phenyl]propionamide (1-61 YS-65)

Through similar procedure to that in Example 1 excepting using 2-piperidin-nitrobenzene as a starting material, N-(4-tert-Butylbenzyl)-2-[3-piperidino-4-(methylsulfonylamino) phenyl]propionamide having following physicochemical properties was synthesized:

86% yield, white solid, mp=125° C.

$^1$H NMR (CDCl$_3$) δ 7.78 (bs, 1H), 7.45 (d, 1H, J=8.4 Hz), 7.31 (bd, 2H), 7.15 (d, 1H, J=2 Hz), 7.10 (bd, 2H), 7.05 (dd, 1H, J=8.4, 2 Hz), 5.59 (bt, 1H), 4.38 (d of AB, 2H, J=5.7 Hz), 3.52 (q, 1H, J=7.1 Hz), 3.04 (s, 3H), 2.75 (m, 4H), 1.65-1.75 (m, 4H), 1.6 (m, 2H), 1.52 (d, 3H, J=7.1 Hz), 1.29 (s, 9H)

MS (FAB) m/z 472 (MH$^+$)

Example 12

Preparation of N-(4-tert-Butylbenzyl)-2-[3-morpholino-4-(methylsulfonylamino)phenyl]propionamide (1-62 YS-49)

Through similar procedure to that in Example 1 excepting using 2-morpholin-nitrobenzene as a starting material, N-(4-tert-Butylbenzyl)-2-[3-morpholino-4-(methylsulfonylamino)phenyl]propionamide having following physicochemical properties was synthesized:

84% yield, white solid, mp=78° C.

$^1$H NMR (CDCl$_3$) δ 7.69 (bs, 1H), 7.46 (d, 1H, J=8.2 Hz), 7.32 (bd, 2H), 7.18 (d, 1H, J=1.8 Hz), 7.08-7.15 (m, 3H), 5.63 (bt, 1H), 4.38 (d of AB, 2H, J=5.5 Hz), 3.85 (m, 4H), 3.52 (q, 1H, J=7.1 Hz), 3.08 (s, 3H), 2.84 (m, 4H), 1.52 (d, 3H, J=7.1 Hz), 1.29 (s, 9H)

MS (FAB) m/z 474 (MH$^+$)

Example 13

Preparation of N-(4-tert-Butylbenzyl)-2-[3-(N-boc)piperazino-4-(methylsulfonylamino)phenyl]propionamide (1-63 YS-76)

Through similar procedure to that in Example 1 excepting using 2-(N-Boc)piperazine-nitrobenzene as a starting material, N-(4-tert-Butylbenzyl)-2-[3-(N-boc)piperazino-4-(methylsulfonylamino)phenyl]propionamide having following physicochemical properties was synthesized:

88% yield, white solid, mp=103° C.

$^1$H NMR (CDCl$_3$) δ 7.66 (bs, 1H), 7.46 (d, 1H, J=8.2 Hz), 7.32 (bd, 2H), 7.15 (d, 1H, J=1.8 Hz), 7.08-7.13 (m, 3H), 5.60 (bt, 1H), 4.38 (ddd of AB, 2H), 3.58 (m, 4H), 3.49 (q, 1H, J=7.1 Hz), 3.08 (s, 3H), 2.79 (m, 4H), 1.55 (d, 3H, J=7.1 Hz), 1.49 (s, 9H), 1.30 (s, 9H)

MS (FAB) m/z 573 (MH$^+$)

Example 14

Preparation of N-(4-tert-Butylbenzyl)-2-[3-piperazino-4-(methylsulfonylamino)phenyl]propionamide (1-64 YS-79)

Through similar procedure to that in Example 1 excepting using 2-piperazine-nitrobenzene as a starting material, N-(4-tert-Butylbenzyl)-2-[3-piperazino-4-(methylsulfonylamino) phenyl]propionamide having following physicochemical properties was synthesized:

96% yield, white solid, mp=92° C.

$^1$H NMR (CDCl$_3$) δ 7.46 (d, 1H, J=8.3 Hz), 7.32 (bd, 2H), 7.18 (d, 1H, J=1.8 Hz), 7.08-7.13 (m, 3H), 5.60 (bt, 1H), 4.38 (d of AB, 2H, J=5 Hz), 3.52 (q, 1H, J=7.1 Hz), 3.06 (s, 3H), 3.03 (m, 4H), 2.80 (m, 4H), 1.52 (d, 3H, J=7.1 Hz), 1.29 (s, 9H)

MS (FAB) m/z 473 (MH$^+$)

Example 15

Preparation of N-(4-tert-Butylbenzyl)-2-[3-methoxy-4-(methylsulfonylamino)phenyl]propionamide (1-65, CHK-717)

Through similar procedure to that in Example 1 excepting using 2-[3-methoxy-4-(methylsulfonylamino)phenyl]propion acid as a starting material, N-(4-tert-Butylbenzyl)-2-[3-methoxy-4-(methylsulfonylamino)phenyl]propionamide having following physicochemical properties was synthesized:

83% yield, white solid, mp=74-76° C.

$^1$H NMR (CDCl$_3$) δ 7.1-7.5 (m, 5H), 6.85-6.9 (m, 2H), 6.75 (bs, 1H), 5.75 (bt, 1H), 4.39 (ddd of AB, 2H), 3.85 (s, 3H), 3.54 (q, 1H, J=7.1 Hz), 2.94 (s, 3H), 1.53 (d, 3H, J=7.1 Hz), 1.31 (s, 9H)

MS (FAB) m/z 419 (MH$^+$)

Example 16

Preparation of N-(4-tert-Butylbenzyl)-2-[2-fluoro-4-(methylsulfonylamino)phenyl]propionamide (1-66 KMJ-708)

Through similar procedure to that in Example 1 excepting using 3-fluoro-nitrobenzene as a starting material, N-(4-tert-Butylbenzyl)-2-[2-fluoro-4-(methylsulfonylamino)phenyl] propionamide having following physicochemical properties was synthesized:

63% yield, white solid, mp=111-113° C.

$^1$H NMR (CDCl$_3$) δ 7.3-7.38 (m, 3H), 7.28 (bs, 1H), 7.15 (bd, 2H), 7.02 (dd, 1H, J=11.4, 2.2 Hz), 6.87 (dd, 1H, J=8.4, 2.2 Hz), 5.88 (bt, 1H), 4.41 (ddd of AB, 2H), 3.84 (q, 1H, J=7.1 Hz), 3.00 (s, 3H), 1.52 (d, 3H, J=7.1 Hz), 1.30 (s, 9H)

MS (FAB) m/z 407 (MH$^+$)

Example 17

Preparation of N-(4-tert-Butylbenzyl)-2-[2-chloro-4-(methylsulfonylamino)phenyl]propionamide (1-67 KMJ-698)

Through similar procedure to that in Example 1 excepting using 3-fluoro-nitrobenzene as a starting material, N-(4-tert-Butylbenzyl)-2-[2-chloro-4-(methylsulfonylamino)phenyl] propionamide having following physicochemical properties was synthesized:

46% yield, white solid, mp=134-136° C.

$^1$H NMR (CDCl$_3$) δ 7.44 (d, 1H, J=8.4 Hz), 7.34 (bd, 2H), 7.29 (d, 1H, J=2.2 Hz), 7.15 (bd, 2H), 7.07 (dd, 1H, J=8.4, 2.2 Hz), 5.88 (bt, 1H), 4.40 (ddd of AB, 2H), 3.84 (q, 1H, J=7.1 Hz), 3.00 (s, 3H), 1.52 (d, 3H, J=7.1 Hz), 1.30 (s, 9H)

MS (FAB) m/z 423 (MH$^+$)

Example 18

Preparation of N-(4-tert-Butylbenzyl)-2-[4-(methylsulfonylamino)phenyl]propionamide (2-7, KMJ-750)

Step 18-1. Preparation of N-(4-tert-Butylbenzyl)-2-(4-nitrophenyl)propionamide (2-1, KMJ-738)

Through similar procedure to that in Example 1-5 excepting using 2-(4-nitrophenyl)-propionamide as a starting material, N-(4-tert-Butylbenzyl)-2-(4-nitrophenyl)propionamide having following physicochemical properties was synthesized:

84% yield, white solid, mp=146-148° C.

$^1$H NMR (CDCl$_3$) δ 8.16 (dt, 2H), 7.49 (dt, 2H), 7.32 (dt, 2H), 7.10 (dt, 2H), 5.86 (bt, 1H), 4.37 (ddd, 2H), 3.64 (q, 1H, J=7.1 Hz), 1.55 (d, 3H, J=7.1 Hz), 1.29 (s, 9H)

Step 18-2. Preparation of N-(4-tert-Butylbenzyl)-2-(4-aminophenyl)propionamide (24 KMJ-740)

Through similar procedure to that in Example 1-2 excepting using N-(4-tert-Butylbenzyl)-2-(4-nitrophenyl)propionamide as a starting material, N-(4-tert-Butylbenzyl)-2-(4-aminophenyl)propionamide having following physicochemical properties was synthesized:

95% yield, colorless oil $^1$H NMR (CDCl$_3$) δ 7.31 (dt, 2H), 7.05-7.1 (m, 4H), 6.65 (dt, 2H), 5.66 (bt, 1H), 4.34 (ddd, 2H), 3.66 (bs, 2H), 3.49 (q, 1H, J=7.1 Hz), 1.51 (d, 3H, J=7.1 Hz), 1.29 (s, 9H)

Step 18-3. Preparation of N-(4-tert-Butylbenzyl)-2-[4-(methylsulfonylamino)phenyl]propionamide (2-7, KMJ-750)

Through similar procedure to that in Example 1-3 excepting using N-(4-tert-Butylbenzyl)-2-(4-aminophenyl)propionamide as a starting material, N-(4-tert-Butylbenzyl)-2-[4-(methylsulfonylamino)phenyl]propionamide having following physicochemical properties was synthesized:

93% yield, white solid, mp=77-79° C.

$^1$H NMR (CDCl$_3$) δ 7.32 (dt, 2H), 7.27 (dt, 2H), 7.18 (dt, 2H), 7.11 (dt, 2H), 6.96 (bs, 1H), 5.73 (bt, 1H), 4.38 (ddd, 2H), 3.55 (q, 1H, J=7.1 Hz), 2.98 (s, 3H), 1.52 (d, 3H, J=7.1 Hz), 1.29 (s, 9H)

MS (EI) m/z 388 (M$^+$)

Example 19

Preparation of N-(4-Chlorobenzyl)-2-[4-(methylsulfonylamino)phenyl]propionamide (2-8, YS-85)

Through similar procedure to that in Example 18 excepting using 4-chlorobenzyl amine as a starting material, N-(4-Chlorobenzyl)-2-[4-(methylsulfonylamino)phenyl]propionamide having following physicochemical properties was synthesized:

94% yield, white solid, mp=164° C.
$^1$H NMR (CDCl$_3$) δ 7.24-7.32 (m, 4H), 7.18 (dt, 2H), 7.10 (dt, 2H), 6.59 (bs, 1H), 5.70 (bt, 1H), 4.37 (ddd, 2H), 3.56 (q, 1H, J=7.1 Hz), 3.01 (s, 3H), 1.53 (d, 3H, J=7.1 Hz)
MS (EI) m/z 366 (M$^+$)

Example 20

Preparation of N-(3,4-Dichlorobenzyl)-2-[4-(methylsulfonylamino)phenyl]propionamide (2-9, YS-97)

Through similar procedure to that in Example 18 excepting using 3,4-dichlorobenzyl amine as a starting material, N-(3,4-Dichlorobenzyl)-2-[4-(methylsulfonylamino)phenyl]propionamide having following physicochemical properties was synthesized:

96% yield, white solid, mp=130° C.
$^1$H NMR (CDCl$_3$) δ 7.18-7.38 (m, 5H), 7.01 (d, 1H), 6.38 (bs, 1H), 5.68 (bt, 1H), 4.35 (d, 2H, J=5.8 Hz), 3.58 (q, 1H, J=7.1 Hz), 3.02 (s, 3H), 1.53 (d, 3H, J=7.1 Hz)
MS (EI) m/z 400 (M$^+$)

Example 21

Preparation of N-(4-tert-Butylbenzyl)-(2S)-2-[3-fluoro-4-(methylsulfonylamino)phenyl]propionamide (3-5, SU-834)

Step 21-1. N-[(1S)-1-Benzyl-2-hydroxyethyl]-(2S)-2-[3-fluoro-4-(methylsulfonylamino)phenyl]propionamide (3-1. SU-632-H)

A mixture of 2-[3-fluoro-4-(methylsulfonylamino)phenyl] propion acid (100 mg, 0.234 mmol) and L-phenyl alaninol (71 mg, 0.468 mmol) in CH$_2$Cl$_2$ (3 mL) was refluxed for 3 h and concentrated in vacuo. The residue was dissolved in MeOH (2 mL) and purified by flash column chromatography on silica gel using EtOAc:hexanes (2:1) to EtOAc:MeOH (20:1) as eluant to afford N-[(1S)-1-Benzyl-2-hydroxyethyl]-(2S)-2-[3-fluoro-4-(methylsulfonylamino)phenyl]propionamide.

mp=150-153° C., [α]=−20.36 (c 1.00, MeOH)
$^1$H NMR (CD$_3$OD) δ 7.36 (t, 1H, J=8.5 Hz), 7.0-7.28 (m, 7H), 4.07 (m, 1H), 3.56 (q, 1H, J=7.3 Hz), 3.48 (dd, 2H, J=1.2, 5.1 Hz), 2.9-3.0 (m, 4H), 2.71 (dd, 1H, J=9, 14 Hz), 1.27 (d, 3H, J=7.05 Hz)

Step 21-2. (2S)-[3-Fluoro-4-(methylsulfonylamino) phenyl]propionic acid (3-3. SU-668)

A solution of N-[(1S)-1-Benzyl-2-hydroxyethyl]-(2S)-2-[3-fluoro-4-(methylsulfonylamino)phenyl]propionamide (100 mg, 0.234 mmol) in 3 N H$_2$SO$_4$ (1 mL) and 1,4-dioxane (1 mL) was heated to 100° C. for 5 h and cooled to room temperature. The solution was diluted with water and extracted with CH$_2$Cl$_2$ several times. The combined organic layers were washed with water, dried over MgSO$_4$, and concentrated in vacuo to afford (2S)-[3-Fluoro-4-(methylsulfonylamino)phenyl]propionic acid.

73% yield
$^1$H NMR (CDCl$_3$) δ 7.52 (t, 1H, J=8.3 Hz), 7.1-7.2 (m, 2H), 6.68 (bs, 1H), 3.73 (q, 1H, J=7.3 Hz), 3.03 (s, 3H), 1.51 (d, 3H, J=7.3 Hz)
[α]=+29.76 (c 1.00, CHCl$_3$)

Step 21-3. N-(4-tert-Butylbenzyl)-(2S)-2-[3-fluoro-4-(methylsulfonylamino)phenyl]propionamide (3-5, SU-834)

Through similar procedure to that in Example 1-5 excepting using (2S)-[3-Fluoro-4-(methylsulfonylamino)phenyl] propionic acid as a starting material, N-(4-tert-Butylbenzyl)-(2S)-2-[3-fluoro-4-(methylsulfonylamino)phenyl] propionamide having following physicochemical properties was synthesized:

98% yield, white solid, mp 52~54° C.
[α]=−15.5 (c 0.5, CHCl$_3$)
$^1$H NMR (CDCl$_3$) δ 7.51 (t, 1H, J=8.3 Hz), 7.33 (m, 2H), 7.06-7.2 (m, 4H), 6.58 (bs, 1H), 5.73 (bt, 1H), 4.38 (ddd of AB, 2H, J=5.5, 14.6 Hz), 3.52 (q, 1H, J=7.1 Hz), 3.02 (s, 3H), 1.52 (d, 3H, J=7.1 Hz), 1.30 (s, 9H)
MS (FAB) m/z 407 (MH$^+$)

Example 22

Preparation of N-(4-tert-Butylbenzyl)-(2R)-2-[3-fluoro-4-(methylsulfonylamino)phenyl]propionamide (3-6, SU-824)

Step 22-1. N-[(115)-1-Benzyl-2-hydroxyethyl]-(2R)-2-[3-fluoro-4-(methylsulfonylamino)phenyl]propionamide (3-2. SU-632-L)

Through similar procedure to that in Example 10, N-[(1S)-1-Benzyl-2-hydroxyethyl]-(2R)-2-[3-fluoro-4-(methylsulfonylamino)phenyl]propionamide having following physicochemical properties was synthesized:

mp=164~166° C., [α]=−25.48 (c 1.00, MeOH)
$^1$H NMR (CD$_3$OD) δ 7.33 (t, 1H, J=8.5 Hz), 6.9-7.12 (m, 7H), 4.12 (m, 1H), 3.5-3.6 (m, 3H), 2.98 (s, 3H), 2.88 (dd, 1H, J=5.1, 14 Hz), 2.71 (dd, 1H, J=9.3, 14 Hz), 1.36 (d, 3H, J=7.05 Hz)

Step 22-2. (2R)-[3-Fluoro-4-(methylsulfonylamino) phenyl]propionic acid (3-4, SU-732)

Through similar procedure to that in Example 10-2 excepting using (2R)-[3-Fluoro-4-(methylsulfonylamino)phenyl] propionic acid as a starting material, (2R)-[3-Fluoro-4-(methylsulfonylamino)phenyl]propionic acid having following physicochemical properties was synthesized:
The spectral data of this compound is identical to that of 3-3.
[α]=−29.25 (c 1.00, CHCl$_3$)

Step 22-3. N-(4-tert-Butylbenzyl)-(2R)-2-[3-fluoro-4-(methylsulfonylamino)phenyl]propionamide (3-6, SU-824)

Through similar procedure to that in Example 10-3, N-(4-tert-Butylbenzyl)-(2R)-2-[3-fluoro-4-(methylsulfonylamino)phenyl]propionamide having following physicochemical properties was synthesized:

96% yield, white solid, mp=52~54° C.
[α]=+18.4 (c 0.5, CHCl$_3$)

Example 23

Preparation of N-(4-Chlorobenzyl)-2-[3-fluoro-4-(methylsulfonylamino)phenyl]propionamide (4-1, SH-291)

Through similar procedure to that in Example 1-5 excepting using 2-[3-fluoro-4-(metylsulfonylamino)phenyl]propion acid (1-39) with the corresponding 4-chlorobenzylamine compound as a starting material, N-(4-Chlorobenzyl)-2-[3-fluoro-4-(methylsulfonylamino)phenyl]propionamide having following physicochemical properties was synthesized:

98% yield, white solid, mp=129-130° C.

$^1$H NMR (CDCl$_3$) δ 7.53 (t, 1H, J=8.3 Hz), 7.25-7.3 (m, 2H), 7.06-7.2 (m, 4H), 6.44 (bs, 1H), 5.67 (bt, 1H), 4.37 (ddd of AB, 2H), 3.53 (q, 1H, J=7.1 Hz), 3.03 (s, 3H), 1.52 (d, 3H, J=7.1 Hz)

MS (FAB) m/z 385 [M-H]$^+$

Example 24

Preparation of N-(4-Chlorobenzyl)-2-[3-chloro-4-(methylsulfonylamino)phenyl]propionamide (4-2, SH-290)

Through similar procedure to that in Example 1-5 excepting using 2-[3-fluoro-4-(metylsulfonylamino)phenyl]propion acid (1-39) with the corresponding 4-chlorobenzylamine compound as a starting material, N-(4-Chlorobenzyl)-2-[3-chloro-4-(methylsulfonylamino)phenyl]propionamide having following physicochemical properties was synthesized:

98% yield, white solid, mp=134-135° C.

$^1$H NMR (CDCl$_3$) δ 7.61 (d, 1H, J=8.3 Hz), 7.41 (d, 1H, J=1.2 Hz), 7.2-7.3 (m, 3H), 7.13 (d, 2H), 6.73 (bs, 1H), 5.68 (bt, 1H), 4.38 (ddd of AB, 2H), 3.52 (q, 1H, J=7.1 Hz), 3.02 (s, 3H), 1.52 (d, 3H, J=7.1 Hz)

MS (FAB) m/z 402 (MH$^+$)

Example 25

Preparation of N-(4-Chlorobenzyl)-2-[3-bromo-4-(methylsulfonylamino)phenyl]propionamide (4-3, SH-335)

Through similar procedure to that in Example 1-5 excepting using 2-[3-Bromo-4-(methylsulfonylamino)phenyl]propionic acid (1-40) with the corresponding 4-chlorobenzylamine compound as a starting material, N-(4-Chlorobenzyl)-2-[3-bromo-4-(methylsulfonylamino)phenyl]propionamide having following physicochemical properties was synthesized:

88% yield, white solid, mp=147° C.

$^1$H NMR (CDCl$_3$) δ 7.60 (d, 1H, J=8.4 Hz), 7.57 (d, 1H, J=1.2 Hz), 7.24-7.32 (m, 3H), 7.13 (d, 2H), 6.74 (bs, 1H), 5.73 (bt, 1H), 4.36 (ddd of AB, 2H), 3.52 (q, 1H, J=7.1 Hz), 3.01 (s, 3H), 1.52 (d, 3H, J=7.1 Hz)

MS (FAB) m/z 446 (MH$^+$)

The spectral data is identical to those of compound 3-5
MS (FAB) m/z 407 (MH$^+$)

Example 26

Preparation of N-(3,4-Dichlorobenzyl)-2-[3-fluoro-4-(methylsulfonylamino)phenyl]propionamide (4-4, SH-94)

Through similar procedure to that in Example 1-5 excepting using 2-[3-Fluoro-4-(methylsulfonylamino)phenyl]propionic acid (1-38) with the corresponding 3,4-dichlorobenzylamine compound as a starting material, N-(3,4-Dichlorobenzyl)-2-[3-fluoro-4-(methylsulfonylamino)phenyl]propionamide having following physicochemical properties was synthesized:

76% yield, white solid, mp=130-133° C.

$^1$H NMR (CDCl$_3$) δ 7.53 (t, 1H, J=8.3 Hz), 7.36 (d, 1H), 7.23 (d, 1H), 7.16 (dd, 1H), 7.10 (bd, 1H), 7.02 (dd, 1H), 6.51 (bs, 1H), 5.76 (bt, 1H), 4.36 (d of AB, 2H), 3.54 (q, 1H, J=7.1 Hz), 3.03 (s, 3H), 1.52 (d, 3H, J=7.1 Hz)

MS (FAB) m/z 419 (MH$^+$)

Example 27

Preparation of N-(3,4-Dichlorobenzyl)-2-[3-chloro-4-(methylsulfonylamino)phenyl]propionamide (4-5, SH-286)

Through similar procedure to that in Example 1-5 excepting using 2-[3-chloro-4-(methylsulfonylamino)phenyl]propion acid (1-39) with the corresponding 3,4-dichlorobenzylamine compound as a starting material, N-(3,4-Dichlorobenzyl)-2-[3-chloro-4-(methylsulfonylamino)phenyl]propionamide having following physicochemical properties was synthesized:

85% yield, white solid, mp=129-130° C.

$^1$H NMR (CDCl$_3$) δ 7.59 (d, 1H, J=8.4 Hz), 7.41 (d, 1H), 7.36 (d, 1H), 7.2-7.25 (m, 2H), 7.03 (dd, 1H), 6.78 (bs, 1H), 5.91 (bt, 1H), 4.35 (d of AB, 2H, J=6 Hz), 3.54 (q, 1H, J=7.0 Hz), 3.02 (s, 3H), 1.52 (d, 3H, J=7.0 Hz)

MS (FAB) m/z 435 (MH$^+$)

Example 28

Preparation of N-(3,4-Dichlorobenzyl)-2-[3-bromo-4-(methylsulfonylamino)phenyl]propionamide (4-6, SH-337)

Through similar procedure to that in Example 1-5 excepting using 2-[3-bromo-4-(methylsulfonylamino)phenyl]propion acid (1-40) with the corresponding 3,4-dichlorobenzylamine compound as a starting material, N-(3,4-Dichlorobenzyl)-2-[3-bromo-4-(methylsulfonylamino)phenyl]propionamide having following physicochemical properties was synthesized:

98% yield, white solid, mp=161-162° C.

$^1$H NMR (CDCl$_3$) δ 7.62 (d, 1H, J=8.4 Hz), 7.57 (d, 1H, J=1.8 Hz), 7.37 (d, 1H, J=8.4 Hz), 7.2-7.3 (m, 2H), 7.04 (dd, 1H, J=1.8 & 8.2 Hz), 6.75 (bs, 1H), 5.75 (bt, 1H), 4.37 (d of AB, 2H, J=6 Hz), 3.53 (q, 1H, J=7.1 Hz), 3.02 (s, 3H), 1.52 (d, 3H, J=7.1 Hz)

MS (FAB) m/z 481 (MH$^+$)

Example 29

Preparation of N-(4-Methylbenzyl)-2-[3-fluoro-4-(methylsulfonylamino)phenyl]propionamide (4-7, SH-351)

Through similar procedure to that in Example 1-5 excepting using 2-[3-Fluoro-4-(methylsulfonylamino)phenyl]propionic acid (1-38) with the corresponding 4-methylbenzylamine compound as a starting material, N-(4-Methylbenzyl)-2-[3-fluoro-4-(methylsulfonylamino)phenyl]propionamide having following physicochemical properties was synthesized:

96% yield, white solid, mp=166° C.
$^1$H NMR (CDCl$_3$) δ 7.51 (t, 1H, J=8.3 Hz), 7.05-7.2 (m, 6H), 6.50 (bs, 1H), 5.66 (bt, 1H), 4.36 (ddd of AB, 2H), 3.51 (q, 1H, J=7.1 Hz), 3.02 (s, 3H), 2.32 (s, 3H), 1.52 (d, 3H, J=7.1 Hz)
MS (FAB) m/z 365 (MH$^+$)

Example 30

Preparation of N-(4-Isopropylbenzyl)-2-[3-fluoro-4-(methylsulfonylamino)phenyl]propionamide (4-8, KMJ-928)

Through similar procedure to that in Example 1-5 excepting using 2-[3-Fluoro-4-(methylsulfonylamino)phenyl]propionic acid (1-38) with the corresponding 4-isoprophylbenzylamine compound as a starting material, N-(4-Isopropylbenzyl)-2-[3-fluoro-4-(methylsulfonylamino)phenyl]propionamide having following physicochemical properties was synthesized:

69% yield, white solid, mp=137-139° C.
$^1$H NMR (CDCl$_3$) δ 7.49 (t, 1H, J=8.3 Hz), 7.05-7.2 (m, 6H), 6.70 (bs, 1H), 5.80 (bt, 1H), 4.36 (ddd of AB, 2H), 3.52 (q, 1H, J=7.1 Hz), 3.00 (s, 3H), 2.88 (m, 2H), 1.51 (d, 3H, J=7.1 Hz), 1.22 (d, 6H)
MS (FAB) m/z 393 (MH$^+$)

Example 31

Preparation of N-(4-Methoxybenzyl)-2-[3-fluoro-4-(methylsulfonylamino)phenyl]propionamide (4-9, SH-353)

Through similar procedure to that in Example 1-5 excepting using 2-[3-Fluoro-4-(methylsulfonylamino)phenyl]propionic acid (1-38) with the corresponding 4-metoxybenzylamine compound as a starting material, N-(4-Methoxybenzyl)-2-[3-fluoro-4-(methylsulfonylamino)phenyl]propionamide having following physicochemical properties was synthesized:

96% yield, white solid, mp=138° C.
$^1$H NMR (CDCl$_3$) δ 7.48 (t, 1H, J=8.3 Hz), 7.05-7.2 (m, 4H), 6.82 (d, 2H), 6.69 (bs, 1H), 5.80 (bt, 1H), 4.33 (ddd of AB, 2H), 3.78 (s, 3H), 3.52 (q, 1H, J=7.1 Hz), 3.01 (s, 3H), 1.51 (d, 3H, J=7.1 Hz)
MS (FAB) m/z 381 (MH$^+$)

Example 32

Preparation of N-(4-Trifluoromethylbenzyl)-2-[3-fluoro-4-(methylsulfonylamino)phenyl]propionamide (4-10, SH-93)

Through similar procedure to that in Example 1-5 excepting using 2-[3-Fluoro-4-(methylsulfonylamino)phenyl]propionic acid (1-38) with the corresponding 4-trifluoromethylbenzylamine compound as a starting material, N-(4-Trifluoromethylbenzyl)-2-[3-fluoro-4-(methylsulfonylamino)phenyl]propionamide having following physicochemical properties was synthesized:

81% yield, white solid, mp=150-152° C.
$^1$H NMR (CDCl$_3$) δ 7.5-7.6 (m, 3H), 7.26 (d, 2H), 7.05-7.2 (m, 2H), 5.86 (bt, 1H), 4.46 (ddd of AB, 2H), 3.56 (q, 1H, J=7.1 Hz), 3.02 (s, 3H), 1.52 (d, 3H, J=7.1 Hz)
MS (FAB) m/z 419 (MH$^+$)

Example 33

Preparation of N-(4-Biphenylmethyl)-2-[3-fluoro-4-(methylsulfonylamino)phenyl]propionamide (4-11, KMJ-498)

Through similar procedure to that in Example 1-5 excepting using 2-[3-Fluoro-4-(methylsulfonylamino)phenyl]propionic acid (1-38) with the corresponding 4-phenylbenzylamine compound as a starting material, N-(4-Biphenylmethyl)-2-[3-fluoro-4-(methylsulfonylamino)phenyl]propionamide having following physicochemical properties was synthesized:

78% yield, white solid, mp=155-157° C.
$^1$H NMR (CDCl$_3$) δ 7.1-7.58 (m, 12H), 6.45 (bs, 1H), 5.71 (bt, 1H), 4.45 (ddd, 2H), 3.55 (q, 1H, J=7.1 Hz), 3.01 (s, 3H), 1.54 (d, 3H, J=7.1 Hz)
MS (FAB) m/z 427 (MH$^+$)

Example 34

Preparation of N-(1-Naphthylmethyl)-2-[3-fluoro-4-(methylsulfonylamino)phenyl]propionamide (4-12, SH-92)

Through similar procedure to that in Example 1-5 excepting using 2-[3-Fluoro-4-(methylsulfonylamino)phenyl]propionic acid (1-38) with the corresponding 4-chlorobenzylamine compound as a starting material, N-(1-Naphthylmethyl)-2-[3-fluoro-4-(methylsulfonylamino)phenyl]propionamide having following physicochemical properties was synthesized:

79% yield, white solid, mp=159-161° C.
$^1$H NMR (CDCl$_3$) δ 7.75-7.9 (m, 3H), 7.3-7.5 (m, 5H), 7.16 (dd, 1H), 7.04 (bd, 1H), 6.52 (bs, 1H), 5.69 (bt, 1H), 4.86 (ddd, 2H), 3.49 (q, 1H, J=7.1 Hz), 2.96 (s, 3H), 1.51 (d, 3H, J=7.1 Hz)
MS (FAB) m/z 401 (MH$^+$)

Example 35

Preparation of N-(1,2,3,4-Tetrahydro-1-naphthalenyl)-2-[3-fluoro-4-(methylsulfonylamino)phenyl]propionamide (4-13, SH-112)

Through similar procedure to that in Example 1-5 excepting using 2-[3-Fluoro-4-(methylsulfonylamino)phenyl]propionic acid (1-38) with the corresponding 1,2,3,4-tetrahydro-1-naphtalenamine compound as a starting material, N-(1,2,3,4-Tetrahydro-1-naphthalenyl)-2-[3-fluoro-4-(methylsulfonylamino)phenyl]propionamide having following physicochemical properties was synthesized:

73% yield, white solid, mp=116-117° C.
$^1$H NMR (CDCl$_3$) δ 7.51 (m, 1H), 6.8-7.2 (m, 6H), 6.53 (bs, 1H), 5.62 (bd, 1H), 5.15 (m, 1H), 3.51 (q, 1H, J=7.1 Hz), 3.00 (s, 3H), 2.75 (m, 2H), 1.7-1.9 (m, 4H), 1.53 (d, 3H, J=7.1 Hz)
MS (FAB) m/z 391 (MH$^+$)

Example 36

Preparation of N-[2-(4-t-Butylphenyl)ethyl]-2-[3-fluoro-4-(methylsulfonylamino)phenyl]propionamide (4-14, KMJ-374)

Through similar procedure to that in Example 1-5 excepting using 2-[3-Fluoro-4-(methylsulfonylamino)phenyl]propionic acid (1-38) with the corresponding 2-(4-t-Butyl)ethyl amine compound as a starting material, N-[2-(4-t-Butylphenyl)ethyl]-2-[3-fluoro-4-(methylsulfonylamino)phenyl]propionamide having following physicochemical properties was synthesized:

64% yield, white solid, mp=124-126° C.
$^1$H NMR (CDCl$_3$) δ 7.50 (t, 1H, J=8.3 Hz), 7.29 (bd, 2H), 6.95-7.15 (m, 4H), 6.52 (bs, 1H), 5.41 (bt, 1H), 3.47 (m, 3H), 3.03 (s, 3H), 2.72 (t, 2H, J=6.8 Hz), 1.47 (d, 3H, J=7.3 Hz), 1.31 (s, 9H)
MS (FAB) m/z 421 (MH$^+$)

Example 37

Preparation of N-[3-(3,4-Dimethylphenyl)propyl]-2-[3-fluoro-4-(methylsulfonylamino)phenyl]propionamide (4-15, SU-770)

Through similar procedure to that in Example 1-5 excepting using 2-[3-Fluoro-4-(methylsulfonylamino)phenyl]propionic acid (1-38) with the corresponding 3-(3,4-Dimethylphenyl)propyl racemic amine compound as a starting material, N-[3-(3,4-Dimethylphenyl)propyl]-2-[3-fluoro-4-(methylsulfonylamino)phenyl]propionamide having following physicochemical properties was synthesized:

95% yield, white solid, mp=128-130° C.,
$^1$H NMR (CDCl$_3$) δ 7.50 (t, 1H, J=8.3 Hz), 7.13 (dd, 1H, J=1.95, 11.2Hz), 7.0-7.07 (m, 2H), 6.83-6.92 (m, 2H), 6.57 (bs, 1H), 3.41 (q, 1H, J=7.1 Hz), 3.2-3.3 (m, 2H), 3.01 (s, 3H), 2.51 (t, 2H, J=7.6 Hz), 2.22 (s, 6H), 1.7-1.8 (m, 2H), 1.45 (d, 3H, J=7.1 Hz)
MS (FAB) m/z 407 (MH$^+$)

Example 38

Preparation of N-[3-(3,4-Dimethylphenyl)propyl]-(2R)-2-[3-fluoro-4-(methylsulfonylamino)phenyl]propionamide (4-16, SU-774)

Through similar procedure to that in Example 1-5 excepting using 2-[3-Fluoro-4-(methylsulfonylamino)phenyl]propionic acid (1-38) with the corresponding 3-(3,4-Dimethylphenyl)propyl-R-amine compound as a starting material, N-[3-(3,4-Dimethylphenyl)propyl]-(2R)-2-[3-fluoro-4-(methylsulfonylamino)phenyl]propionamide having following physicochemical properties was synthesized:

96% yield, white solid, mp=128~130° C.
The spectral data of compound 4-16 are identical to those of compound 4-15.
[α]=−4.23 (c 0.25, CHCl$_3$)
MS (FAB) m/z 407 (MH$^+$)

Example 39

Preparation of N-[3-(3,4-Dimethylphenyl)propyl]-(2S)-2-[3-fluoro-4-(methylsulfonylamino)phenyl]propionamide (4-17, SU-776)

Through similar procedure to that in Example 1-5 excepting using 2-[3-Fluoro-4-(methylsulfonylamino)phenyl]propionic acid (1-38) with the corresponding 3-(3,4-Dimethylphenyl)propyl]-S-amine compound as a starting material, N-[3-(3,4-Dimethylphenyl)propyl]-(2S)-2-[3-fluoro-4-(methylsulfonylamino)phenyl]propionamide having following physicochemical properties was synthesized:

95% yield, white solid, mp=128~130° C.
The spectral data of compound 4-17 are identical to those of compound 4-15.
[α]=+4.34 (c 0.25, CHCl$_3$)
MS (FAB) m/z 407 (MH$^+$)

Example 40

Preparation of N-[3-(3,4-Dimethylphenyl)-2-propenyl]-2-[3-fluoro-4-(methylsulfonylamino)phenyl]propionamide (4-18, KMJ-686)

Through similar procedure to that in Example 1-5 excepting using 2-[3-Fluoro-4-(methylsulfonylamino)phenyl]propionic acid (1-38) with the corresponding 3-(3,4-Dimethylphenyl)-2-prophenylamine compound as a starting material; N-[3-(3,4-Dimethylphenyl)-2-propenyl]-2-[3-fluoro-4-(methylsulfonylamino)phenyl]propionamide having following physicochemical properties was synthesized:

78% yield, white solid, mp=144-146° C.
$^1$H NMR (CDCl$_3$) δ 7.52 (t, 1H, J=8.3 Hz), 7.0-7.2 (m, 5H), 6.58 (bs, 1H), 6.37 (d, 1H, J=15.8 Hz), 6.06 (dt, 1H, J=6.2, 15.8 Hz), 5.57 (bt, 1H), 3.9-4.02 (m, 2H), 3.53 (q, 1H, J=7.1 Hz), 3.01 (s, 3H), 2.24 (s, 6H), 1.52 (d, 3H, J=7.1 Hz)
MS (FAB) m/z 405 (MH$^+$)

Example 41

Preparation of N-[3-(4-Chlorophenyl)propyl]-2-[3-fluoro-4-(methylsulfonylamino)phenyl]propionamide (4-19, KMJ-518)

Through similar procedure to that in Example 1-5 excepting using 2-[3-Fluoro-4-(methylsulfonylamino)phenyl]propionic acid (1-38) with the corresponding 3-(4-Chlorophenyl)propyl amine compound as a starting material, N-[3-(4-Chlorophenyl)propyl]-2-[3-fluoro-4-(methylsulfonylamino)phenyl]propionamide having following physicochemical properties was synthesized:

70% yield, white solid, mp=141-143° C.
$^1$H NMR (CDCl$_3$) δ 7.51 (t, 1H, J=8.3 Hz), 7.02-7.25 (m, 6H), 6.52 (bs, 1H), 5.38 (bt, 1H), 3.44 (q, 1H, J=7.1 Hz), 3.24 (ddd, 2H), 3.02 (s, 3H), 2.55 (t, 2H, J=7.5 Hz), 1.76 (m, 2H), 1.47 (d, 3H, J=7.1 Hz)
MS (FAB) m/z 413 (MH$^+$)

Example 42

Preparation of N-[3-(4-Chlorophenyl)-2-propenyl]-2-[3-fluoro-4-(methylsulfonylamino)phenyl]propionamide (4-20, KMJ-732)

Through similar procedure to that in Example 1-5 excepting using 2-[3-Fluoro-4-(methylsulfonylamino)phenyl]propionic acid (1-38) with the corresponding 3-(4-Chlorophenyl)prophenyl amine compound as a starting material, N-[3-(4-Chlorophenyl)-2-propenyl]-2-[3-fluoro-4-(methylsulfonylamino)phenyl]propionamide having following physicochemical properties was synthesized:

72% yield, white solid, mp=151-153° C.
$^1$H NMR (CDCl$_3$) δ 7.52 (t, 1H, J=8.3 Hz), 7.08-7.3 (m, 6H), 6.60 (bs, 1H), 6.37 (d, 1H, J=15.8 Hz), 6.10 (dt, 1H, J=6.2, 15.8 Hz), 5.61 (bt, 1H), 3.9-4.1 (m, 2H), 3.54 (q, 1H, J=7.1 Hz), 3.02 (s, 3H), 1.52 (d, 3H, J=7.1 Hz)
MS (EI) m/z 410 (M$^+$)

Example 43

Preparation of N-Benzyloxy-2-[3-fluoro-4-(methylsulfonylamino)phenyl]propionamide (4-21, SH-109)

Through similar procedure to that in Example 1-5 excepting using 2-[3-Fluoro-4-(methylsulfonylamino)phenyl]propionic acid (1-38) with the corresponding benzyloxyamine compound as a starting material, N-Benzyloxy-2-[3-fluoro-4-(methylsulfonylamino)phenyl]propionamide having following physicochemical properties was synthesized:

76% yield, white solid, mp=182-183° C.
$^1$H NMR (CDCl$_3$) δ 7.94 (s, 1H), 7.49 (t, 1H, J=8.3 Hz), 7.25-7.35 (m, 5H), 7.12 (dd, 1H, J=2, 11.2 Hz), 7.02 (dd, 1H, J=2, 8.2 Hz), 6.52 (bs, 1H), 4.87 (s, 2H), 3.35 (q, 1H, J=7.1 Hz), 3.02 (s, 3H), 1.46 (d, 3H, J=7.1 Hz)
MS (FAB) m/z 367 (MH$^+$)

Example 44

Preparation of N-Benzhydryl-2-[3-fluoro-4-(methylsulfonylamino)phenyl]propionamide (4-22, SH-130)

Through similar procedure to that in Example 1-5 excepting using 2-[3-Fluoro-4-(methylsulfonylamino)phenyl]propionic acid (1-38) with the corresponding benzhydrylamine compound as a starting material, N-Benzhydryl-2-[3-fluoro-4-(methylsulfonylamino)phenyl]propionamide having following physicochemical properties was synthesized:

79% yield, white solid, mp=160-161° C.
$^1$H NMR (CDCl$_3$) δ 7.51 (t, 1H, J=8.3 Hz), 7.0-7.4 (m, 10H), 6.20 (d, 1H), 6.04 (bt, 1H), 3.58 (q, 1H, J=7.1 Hz), 3.00 (s, 3H), 1.52 (d, 3H, J=7.1 Hz)
MS (FAB) m/z 427 (MH$^+$)

Example 45

Preparation of N-(2,2-Diphenylethyl)-2-[3-fluoro-4-(methylsulfonylamino)phenyl]propionamide (4-23, SH-116)

Through similar procedure to that in Example 1-5 excepting using 2-[3-Fluoro-4-(methylsulfonylamino)phenyl]propionic acid (1-38) with the corresponding 2,2-Diphenylethylamine compound as a starting material, N-Benzhydryl-2-[3-fluoro-4-(methylsulfonylamino)phenyl]propionamide having following physicochemical properties was synthesized:

64% yield, white solid, mp=129° C.
$^1$H NMR (CDCl$_3$) δ 7.42 (t, 1H, J=8.3 Hz), 7.1-7.3 (m, 10H), 6.95 (dd, 1H), 6.87 (d, 1H), 6.50 (bs, 1H), 5.28 (bt, 1H), 4.12 (t, 1H), 3.75-3.95 (m, 2H), 3.37 (q, 1H, J=7.1 Hz), 3.01 (s, 3H), 1.40 (d, 3H, J=7.1 Hz)
MS (FAB) m/z 441 (MH$^+$)

Example 46

Preparation of N-(3,3-Diphenylpropyl)-2-[3-fluoro-4-(methylsulfonylamino)phenyl]propionamide (4-24, KMJ-378)

Through similar procedure to that in Example 1-5 excepting using 2-[3-Fluoro-4-(methylsulfonylamino)phenyl]propionic acid (1-38) with the corresponding 2,2-Diphenylpropylamine compound as a starting material, N-(3,3-Diphenylpropyl)-2-[3-fluoro-4-(methylsulfonylamino)phenyl]propionamide having following physicochemical properties was synthesized:

76% yield, white solid, mp=66-68° C.
$^1$H NMR (CDCl$_3$) δ 7.51 (t, 1H, J=8.3 Hz), 7.0-7.3 (m, 12H), 6.45 (bs, 1H), 5.27 (bt, 1H), 3.85 (t, 1H, J=7.8 Hz), 3.34 (q, 1H, J=7.1 Hz), 3.21 (ddd, 2H), 3.01 (s, 3H), 2.24 (dd, 2H), 1.43 (d, 3H, J=7.1 Hz)
MS (FAB) m/z 455 (MH$^+$)

Example 47

Preparation of N-(3,3-Diphenyl-2-propenyl)-2-[3-fluoro-4-(methylsulfonylamino)phenyl]propionamide (4-25, KMJ-724)

Through similar procedure to that in Example 1-5 excepting using 2-[3-Fluoro-4-(methylsulfonylamino)phenyl]propionic acid (1-38) with the corresponding 3,3-Diphenyl-2-propenylamine compound as a starting material, N-(3,3-Diphenyl-2-propenyl)-2-[3-fluoro-4-(methylsulfonylamino)phenyl]propionamide having following physicochemical properties was synthesized:

78% yield, white solid, mp=155-157° C.
$^1$H NMR (CDCl$_3$) δ 7.52 (t, 1H, J=8.3 Hz), 7.05-7.4 (m, 12H), 6.50 (bs, 1H), 6.00 (t, 1H, J=7.0 Hz), 5.44 (bt, 1H), 3.85-4.0 (m, 2H), 3.46 (q, 1H, J=7.1 Hz), 3.01 (s, 3H), 1.48 (d, 3H, J=7.1 Hz)
MS (EI) m/z 452 (M$^+$)

Example 48

Preparation of N-[3,3-Di(4-methylphenyl)-2-propenyl]-2-[3-fluoro-4-(methylsulfonylamino)phenyl]propionamide (4-26, KMJ-908)

Through similar procedure to that in Example 1-5 excepting using 2-[3-Fluoro-4-(methylsulfonylamino)phenyl]propionic acid (1-38) with the corresponding 3,3-Di(4-methylphenyl)-2-propenylamine compound as a starting material, N-[3,3-Di(4-methylphenyl)-2-propenyl]-2-[3-fluoro-4-(methylsulfonylamino)phenyl]propionamide having following physicochemical properties was synthesized:

72% yield, white solid, mp=163-165° C.
$^1$H NMR (CDCl$_3$) δ 7.49 (t, 1H, J=8.3 Hz), 6.95-7.2 (m, 10H), 5.93 (t, 1H, J=7.0 Hz), 5.56 (bt, 1H), 3.8-4.0 (m, 2H), 3.47 (q, 1H, J=7.1 Hz), 3.00 (s, 3H), 2.34 (d, 6H), 1.47 (d, 3H, J=7.1 Hz)
MS (FAB) m/z 481 (MH$^+$)

Example 49

Preparation of N-[3,3-Di(4-fluorophenyl)-2-propenyl]-2-[3-fluoro-4-(methylsulfonylamino)phenyl]propionamide (4-27, SH-135)

Through similar procedure to that in Example 1-5 excepting using 2-[3-Fluoro-4-(methylsulfonylamino)phenyl]propionic acid (1-38) with the corresponding 3,3-Di(4-fluorophenyl)-2-propenylamine compound as a starting material, N-[3,3-Di(4-fluorophenyl)-2-propenyl]-2-[3-fluoro-4-(methylsulfonylamino)phenyl]propionamide having following physicochemical properties was synthesized:

78% yield, white solid, mp=57-60° C.

$^1$H NMR (CDCl$_3$) δ 7.49 (t, 1H, J=8.3 Hz), 6.9-7.2 (m, 10H), 6.72 (bs, 1H), 5.92 (t, 1H, J=7.0 Hz), 5.58 (bs, 1H), 3.8-4.0 (m, 2H), 3.48 (q, 1H, J=7.1 Hz), 3.02 (s, 3H), 1.48 (d, 3H, J=7.1 Hz)

MS (FAB) m/z 489 (MH$^+$)

Example 50

Preparation of N-[2-(10,11-Dihydro-5H-dibenzo[a,d]cyclohepten-5-yliden)ethyl]-2-[3-fluoro-4-(methylsulfonylamino)phenyl]propionamide (4-28, SH-199)

Through similar procedure to that in Example 1-5 excepting using 2-[3-Fluoro-4-(methylsulfonylamino)phenyl]propionic acid (1-38) with the corresponding 2-(10,11-Dihydro-5H-dibenzo[a,d]cyclohepten-5-ylidenethyl amine compound as a starting material, N-[2-(10,11-Dihydro-5H-dibenzo[a,d]cyclohepten-5-yliden)ethyl]-2-[3-fluoro-4-(methylsulfonylamino)phenyl]propionamide having following physicochemical properties was synthesized:

76% yield, white solid, mp=67-69° C.

$^1$H NMR (CDCl$_3$) δ 7.50 (t, 1H, J=8.3 Hz), 7.05-7.25 (m, 10H), 6.49 (bs, 1H), 5.80 (t, 1H), 5.40 (bt, 1H), 4.13 (m, 1H), 3.71 (m, 1H), 3.43 (q, 1H, J=7.1 Hz), 3.2-3.4 (m, 4H), 3.01 (s, 3H), 1.46 (d, 3H, J=7.1 Hz)

MS (FAB) m/z 479 (MH$^+$)

Example 51

Preparation of N-[2-(3,4-Dimethylbenzyl)-3-pivaloyloxypropyl]-2-[4-(methylsulfonylamino)phenyl]propionamide (5-1, CHK-512)

The N-[2-(3,4-Dimethylbenzyl)-3-pivaloyloxypropyl]-2-[4-(methylsulfonylamino)phenyl]propionamide was prepared by the similar procedure with that described in above Example 1-5.

75% yield, white solid, mp=112-115° C.

$^1$H NMR (CDCl$_3$) δ 7.28 (m, 2H), 7.16 (m, 2H), 6.8-7.05 (m, 3H), 6.36 (bs, 1H), 5.77 (bt, 1H), 3.98 (m, 1H), 3.77 (m, 1H), 3.45 (m, 1H), 2.95-3.35 (m, 2H), 2.97 (m, 3H), 2.4-2.6 (m, 2H), 2.1-2.25 (m, 6H), 2.04 (m, 1H), 1.47 (d, 3H), 1.20 (s, 9H)

MS (FAB) m/z 503 (MH$^+$)

Example 52

Preparation of N-[2-(4-t-Butylbenzyl)-3-pivaloyloxypropyl]-2-[4-(methylsulfonylamino)phenyl]propionamide (5-2, CHK-514)

The N-[2-(4-t-Butylbenzyl)-3-pivaloyloxypropyl]-2-[4-(methylsulfonylamino)phenyl]propionamide was prepared by the similar procedure with that described in above Example 1-5.

82% yield, white solid, mp=97-100° C.

$^1$H NMR (CDCl$_3$) δ 7.0-7.35 (m, 7H), 6.38 (bs, 1H), 5.81 (bs, 1H), 4.02 (m, 1H), 3.78 (m, 1H), 3.47 (m, 1H), 3.34 (m, 1H), 2.95-3.1 (m, 4H), 2.45-2.55 (m, 2H), 2.09 (m, 1H), 1.47 (d, 3H), 1.30 (s, 9H), 1.21 (s, 9H)

MS (FAB) m/z 531 (MH$^+$)

Example 53

Preparation of 2-[3-Fluoro-4-(methylsulfonylamino)phenyl]-N-[2-(3,4-dimethylbenzyl)-3-pivaloyloxypropyl]propionamide (5-3, SU-542)

The 2-[3-Fluoro-4-(methylsulfonylamino)phenyl]-N-[2-(3,4-dimethylbenzyl)-3-pivaloyloxypropyl]propionamide was prepared by the similar procedure with that described in above Example 1-5.

67% yield, white solid, mp=46-48° C.

$^1$H NMR (CDCl$_3$) δ 7.51 (dt, 1H), 7.0-7.2 (m, 3H), 6.8-6.95 (m, 2H), 6.58 (bs, 1H), 5.91 (bt, 1H), 4.05 (m, 1H), 3.78 (m, 1H), 3.25-3.5 (m, 2H), 2.9-3.1 (m, 4H), 2.45-2.65 (m, 2H), 2.15-2.3 (m, 6H), 2.05 (m, 1H), 1.46 (d, 3H, J=7.3 Hz), 1.22 (s, 1H)

MS (FAB) m/z 521 (MH$^+$)

Example 54

Preparation of 2-[3-Fluoro-4-(methylsulfonylamino)phenyl]-N-[2-(4-tert-butylbenzyl)-3-pivaloyloxypropyl]propionamide (54, SU-564)

The 2-[3-Fluoro-4-(methylsulfonylamino)phenyl]-N-[2-(4-tert-butylbenzyl)-3-pivaloyloxypropyl]propionamide was prepared by the similar procedure with that described in above Example 1-5.

82% yield, white solid, mp=113-115° C.

$^1$H NMR (CDCl$_3$) δ 7.50 (dt, 1H), 7.30 (d, 2H, J=7.8 Hz), 7.15 (dt, 1H), 7.02-7.1 (m, 3H), 6.82 (bs, 1H), 6.00 (bt, 1H), 4.06 (m, 1H), 3.80 (m, 1H), 3.3-3.5 (m, 2H), 2.95-3.1 (m, 4H), 2.5-2.6 (m, 2H), 2.11 (m, 1H), 1.46 (d, 3H, J=7.3 Hz), 1.30 (s, 1H), 1.22 (s, 1H)

MS (FAB) m/z 549 (MH$^+$)

Example 55

Preparation of N-[2-(3,4-Dimethylbenzyl)-3-pivaloyloxypropyl]-2-[3-methoxy-4-(methylsulfonylamino)phenyl]propionamide (5-5, CHK-479)

The N-[2-(3,4-Dimethylbenzyl)-3-pivaloyloxypropyl]-2-[3-methoxy-4-(methylsulfonylamino)phenyl]propionamide was prepared by the similar procedure with that described in above Example 1-5.

87% yield, white solid, mp=54-57° C.

$^1$H NMR (CDCl$_3$) δ 7.44 (m, 1H), 6.7-7.05 (m, 5H), 5.86 (bt, 1H), 3.98 (m, 1H), 3.85 (m, 3H), 3.78 (m, 1H), 3.46 (m, 1H), 2.95-3.35 (m, 2H), 2.90 (m, 3H), 2.4-2.6 (m, 2H), 2.1-2.25 (m, 6H), 2.04 (m, 1H), 1.47 (d, 3H), 1.19 (s, 9H)

MS (FAB) m/z 533 (MH$^+$)

Example 56

Preparation of N-[2-(4-tert-Butylbenzyl)-3-pivaloyloxypropyl]-2-[3-methoxy-4-(methylsulfonylamino)phenyl]propionamide (5-6, CHK-499)

The N-[2-(4-tert-Butylbenzyl)-3-pivaloyloxypropyl]-2-[3-methoxy-4-(methylsulfonylamino)phenyl]propionamide was prepared by the similar procedure with that described in above Example 1-5.

80% yield, white solid, mp=54-57° C.

$^1$H NMR (CDCl$_3$) δ 7.46 (m, 1H), 7.29 (m, 2H), 7.03 (m, 2H), 6.8-6.95 (m, 2H), 6.72 (bs, 1H), 5.83 (bt, 1H), 4.02 (m, 1H), 3.88 (m, 3H), 3.78 (m, 1H), 3.46 (m, 1H), 3.33 (m, 1H), 3.02 (m, 1H), 2.92 (m, 3H), 2.45-2.55 (m, 2H), 2.05 (m, 1H), 1.48 (d, 3H), 1.30 (s, 9H) 1.21 (s, 9H)
MS (FAB) m/z 561 (MH$^+$)

Example 57

Preparation of N-[2-(3,4-Dimethylbenzyl)-3-pivaloyloxypropyl]-2-[3-chloro-4-(methylsulfonylamino)phenyl]propionamide (5-7, KMJ-472)

The N-[2-(3,4-Dimethylbenzyl)-3-pivaloyloxypropyl]-2-[3-chloro-4-(methylsulfonylamino)phenyl]propionamide was prepared by the similar procedure with that described in above Example 1-5.

62% yield, white solid, mp=127-129° C.
$^1$H NMR (CDCl$_3$) δ 7.60 (m, 1H), 7.40 (m, 1H), 7.22 (m, 1H), 6.8-7.05 (m, 3H), 6.72 (bs, 1H), 5.90 (bt, 1H), 4.06 (m, 1H), 3.80 (m, 1H), 3.42 (m, 1H), 3.30 (m, 1H), 3.05 (m, 1H), 2.99 (m, 3H), 2.45-2.65 (m, 2H), 2.15-2.3 (m, 6H), 2.05 (m, 1H), 1.47 (m, 3H), 1.22 (s, 9H)
MS (FAB) m/z 537 (MH$^+$)

Example 58

Preparation of N-[2-(4-tert-Butylbenzyl)-3-pivaloyloxypropyl]-2-[3-chloro-4-(methylsulfonylamino)phenyl]propionamide (5-8, KMJ-690)

The N-[2-(4-tert-Butylbenzyl)-3-pivaloyloxypropyl]-2-[3-chloro-4-(methylsulfonylamino)phenyl]propionamide was prepared by the similar procedure with that described in above Example 1-5.

58% yield, white solid, mp=142-144° C.
$^1$H NMR (CDCl$_3$) δ 7.59 (m, 1H), 7.42 (m, 1H), 7.30 (m, 2H), 7.22 (m, 1H), 7.06 (m, 2H), 6.82 (bd, 1H), 5.98 (bt, 1H), 4.07 (m, 1H), 3.81 (m, 1H), 3.43 (m, 1H), 3.32 (m, 1H), 3.04 (m, 1H), 2.98 (s, 3H), 2.5-2.6 (m, 2H), 2.12 (m, 1H), 1.46 (m, 3H), 1.30 (s, 9H), 1.22 (s, 9H)
MS (FAB) m/z 563 (M$^+$−1)

Example 59

Preparation of N—[(R)-1-Benzyl-2-(pivaloyloxy)ethyl]-(S)-2-[3-fluoro-4-(methylsulfonylamino)phenyl]propionamide (6-1, SU-730)

The N—[(R)-1-Benzyl-2-(pivaloyloxy)ethyl]-(S)-2-[3-fluoro-4-(methylsulfonylamino)phenyl]propionamide was prepared by the similar procedure with that described in above Example 1-5.

96% yield, white solid, mp=115° C., [α]=−1.75 (c 1.00, CHCl$_3$)
$^1$H NMR (CDCl$_3$) δ 7.50 (t, 1H, J=8.3 Hz), 6.95-7.25 (m, 7H), 6.60 (bs, 1H), 5.54 (d, 1H, J=7.8 Hz), 4.42 (m, 1H), 4.04 (ddd of AB, 2H), 3.43 (q, 1H, J=7.1 Hz), 3.04 (s, 3H), 2.75 (dd of AB, 2H), 1.43 (d, 3H, J=7.1 Hz), 1.19 (s, 9H)
MS (FAB) m/z 479 (MH$^+$)

Example 60

Preparation of N—[(S)-1-Benzyl-2-(pivaloyloxy)ethyl]-(S)-2-[3-fluoro-4-(methylsulfonylamino)phenyl]propionamide (6-2, SU-634)

The N—[(S)-1-Benzyl-2-(pivaloyloxy)ethyl]-(S)-2-[3-fluoro-4-(methylsulfonylamino)phenyl]propionamide was prepared by the similar procedure with that described in above Example 1-5.

98% yield, white solid, mp=125-126° C., [α]=−12.56 (c 1.00, CHCl$_3$)
$^1$H NMR (CDCl$_3$) δ 7.50 (t, 1H, J=8.3 Hz), 7.0-7.32 (m, 7H), 6.48 (bs, 1H), 5.60 (d, 1H, J=7.8 Hz), 4.38 (m, 1H), 4.00 (ddd of AB, 2H), 3.43 (q, 1H, J=7.08 Hz), 3.02 (s, 3H), 2.82 (ddd of AB, 2H), 1.44 (d, 3H, J=7.08 Hz), 1.13 (s, 9H)
MS (FAB) m/z 479 (MH$^+$)

Example 61

Preparation of N—[(S)-1-Benzyl-2-(pivaloyloxy)ethyl]-(R)-2-[3-fluoro-4-(methylsulfonylamino)phenyl]propionamide (6-3, SU-636)

The N—[(S)-1-Benzyl-2-(pivaloyloxy)ethyl]-(R)-2-[3-fluoro-4-(methylsulfonylamino)phenyl]propionamide was prepared by the similar procedure with that described in above Example 1-5.

95% yield, white solid, mp=117~119° C., [α]=+1.46 (c 1.00, CHCl$_3$)
The spectral data of the compound 6-3 is identical to that of 6-1.
MS (FAB) m/z 479 (MH$^+$)

Example 62

Preparation of N—[(R)-1-Benzyl-2-(pivaloyloxy)ethyl]-(R)-2-[3-fluoro-4-(methylsulfonylamino)phenyl]propionamide (6-4, SU-728)

The N—[(R)-1-Benzyl-2-(pivaloyloxy)ethyl]-(R)-2-[3-fluoro-4-(methylsulfonylamino)phenyl]propionamide was prepared by the similar procedure with that described in above Example 1-5.

93% yield, white solid mp 124~126° C., [α]=+11.8 (c 1.00, CHCl$_3$)
The spectral data of the compound 6-4 is identical to that of 6-2.
MS(FAB) m/z 479 (MH$^+$)

Example 63

Preparation of N-[(2R)-2-Benzyl-3-(pivaloyloxy)propyl]-(2S)-2-[3-fluoro-4-(methylsulfonylamino)phenyl]propionamide (6-5, SU-826)

The N-[(2R)-2-Benzyl-3-(pivaloyloxy)propyl]-(2S)-2-[3-fluoro-4-(methylsulfonylamino)phenyl]propionamide was prepared by the similar procedure with that described in above Example 1-5.

87% yield, white solid, mp=40-42° C.
[α]=+8.2 (c 0.5, CHCl$_3$)
$^1$H NMR (CDCl$_3$) δ 7.51 (t, 1H, J=8.3 Hz), 7.06-7.32 (m, 7H), 6.50 (bs, 1H), 5.93 (bt, 1H), 4.05 (dd, 1H, J=4, 11.5 Hz), 3.76 (dd, 1H, J=5, 11.5 Hz), 3.45 (q, 1H, J=7.1 Hz), 3.36 (dt, 1H), 2.9-3.05 (m, 4H), 2.58 (d, 2H, J=7.5 Hz), 2.09 (m, 1H, CH), 1.47 (d, 3H, J=7.1 Hz), 1.22 (s, 9H)
MS (FAB) m/z 493 (MH$^+$)

Example 64

Preparation of N-[(2S)-2-Benzyl-3-(pivaloyloxy)propyl]-(2S)-2-[3-fluoro-4-(methylsulfonylamino)phenyl]propionamide (6-6, SU-830)

The N-[(2S)-2-Benzyl-3-(pivaloyloxy)propyl]-(2S)-2-[3-fluoro-4-(methylsulfonylamino)phenyl]propionamide was prepared by the similar procedure with that described in above Example 1-5.

86% yield, white solid, mp=92~94° C.
[α]=+5.8 (c 0.5, CHCl$_3$)
$^1$H NMR (CDCl$_3$) δ 7.52 (t, 1H, J=8.25 Hz), 7.06-7.32 (m, 7H), 6.52 (bs, 1H), 5.92 (bt, 1H), 4.08 (dd, 1H, J=4, 11.5 Hz), 3.79 (dd, 1H, J=5, 11.5 Hz), 3.46 (q, 1H, J=7.1 Hz), 3.33 (dt, 1H), 3.03 (dt, 1H), 3.00 (s, 3H), 2.48-2.62 (m, 2H), 2.13 (m, 1H), 1.47 (d, 3H, J=7.1 Hz), 1.22 (s, 9H)
MS (FAB) m/z 493 (MH$^+$)

Example 65

Preparation of N-[(2S)-2-Benzyl-3-(pivaloyloxy)propyl]-(2R)-2-[3-fluoro-4-(methylsulfonylamino)phenyl]propionamide (6-7, SU-838)

The N-[(2S)-2-Benzyl-3-pivaloyloxy)propyl]-(2R)-2-[3-fluoro-4-(methylsulfonylamino)phenyl]propionamide was prepared by the similar procedure with that described in above Example 1-5.
88% yield, white solid, mp=40-42° C.
[α]=−10.5 (c 0.5, CHCl$_3$)
Its spectral data of the compound 6-7 are identical to those of compound 6-5

Example 66

Preparation of N-[(2R)-2-Benzyl-3-(pivaloyloxy)propyl]-(2R)-2-[3-fluoro-4-(methylsulfonylamino)phenyl]propionamide (6-8, SU-818)

The N-[(2R)-2-Benzyl-3-(pivaloyloxy)propyl]-(2R)-2-[3-fluoro-4-(methylsulfonylamino)phenyl]propionamide was prepared by the similar procedure with that described in above Example 1-5.
89% yield, white solid, mp=92~94° C.
[α]=−12.5 (c 0.5, CHCl$_3$)
Its spectral data of the compound 6-8 are identical to those of compound 6-6.

Example 67

Preparation of N-[(2R)-2-(4-t-Butylbenzyl)-3-(pivaloyloxy)propyl]-(2S)-2-[3-fluoro-4-(methylsulfonylamino)phenyl]propionamide (6-9, MK-271)

The N-[(2R)-2-(4-t-Butylbenzyl)-3-(pivaloyloxy)propyl]-(2S)-2-[3-fluoro-4-(methylsulfonylamino)phenyl]propionamide was prepared by the similar procedure with that described in above Example 1-5.
90% yield, white solid, mp=44-46° C.
[α]=+6.6 (c 1.0, CHCl$_3$)
$^1$H NMR (CDCl$_3$) δ 7.51 (t, 1H, J=8.25 Hz), 7.31 (d, 2H), 7.16 (dd, 1H, J=11.2, 1.8 Hz), 7.03-7.1 (m, 3H), 6.41 (bs, 1H), 5.91 (bt, 1H), 4.06 (dd, 1H, J=4, 11.5 Hz), 3.78 (dd, 1H, J=5, 11.5 Hz), 3.43 (q, 1H, J=7 Hz), 3.36 (ddd, 1H), 2.9-3.05 (m, 4H), 2.55 (d, 2H, J=7.5 Hz), 2.08 (m, 1H), 1.46 (d, 3H, J=7 Hz), 1.30 (s, 9H), 1.22 (s, 9H)
MS (FAB) m/z 549 (MH$^+$)

Example 68

Preparation of N-[(2S)-2-(4-t-Butylbenzyl)-3-(pivaloyloxy)propyl]-(2S)-2-[3-fluoro-4-(methylsulfonylamino)phenyl]propionamide (6-10, MK-272)

The N-[(2S)-2-(4-t-Butylbenzyl)-3-(pivaloyloxy)propyl]-(2S)-2-[3-fluoro-4-(methylsulfonylamino)phenyl]propionamide was prepared by the similar procedure with that described in above Example 1-5.
92% yield, white solid, mp=43-45° C.
[α]=+11.0 (c 1.0, CHCl$_3$)
$^1$H NMR (CDCl$_3$) δ 7.52 (t, 1H, J=8.25 Hz), 7.30 (d, 2H), 7.17 (dd, 1H, J=11.2, 1.8 Hz), 7.0-7.1 (m, 3H), 6.50 (bs, 1H), 5.90 (bt, 1H), 4.08 (dd, 1H, J=4, 11.5 Hz), 3.81 (dd, 1H, J=5, 11.5 Hz), 3.45 (q, 1H, J=7 Hz), 3.34 (ddd, 1H), 2.9-3.1 (m, 4H), 2.53 (ddd of AB, 2H), 2.12 (m, 1H), 1.47 (d, 3H, J=7 Hz), 1.30 (s, 9H), 1.22 (s, 9H)
MS (FAB) m/z 549 (MH$^+$)

Example 69

Preparation of N-[(2S)-2-(4-t-Butylbenzyl)-3-(pivaloyloxy)propyl]-(2R)-2-[3-fluoro-4-(methylsulfonylamino)phenyl]propionamide (6-11, MK-450)

The N-[(2S)-2-(4-t-Butylbenzyl)-3-(pivaloyloxy)propyl]-(2R)-2-[3-fluoro-4-(methylsulfonylamino)phenyl]propionamide was prepared by the similar procedure with that described in above Example 1-5.
87% yield, white solid, mp=44-46° C.
[α]=−8.1 (c 1.0, CHCl$_3$)
MS (FAB) m/z 549 (MH$^+$)
Its spectral data of the compound 6-11 are identical to those of compound 6-9.

Example 70

Preparation of N-[(2R)-2-(4-t-Butylbenzyl)-3-(pivaloyloxy)propyl]-(2R)-2-[3-fluoro-4-(methylsulfonylamino)phenyl]propionamide (6-12, MK-452)

The N-[(2R)-2-(4-t-Butylbenzyl)-3-(pivaloyloxy)propyl]-(2R)-2-[3-fluoro-4-(methylsulfonylamino)phenyl]propionamide was prepared by the similar procedure with that described in above Example 1-5.
90% yield, white solid, mp=43-45° C.
[α]=−6.7 (c 1.0, CHCl$_3$)
MS (FAB) m/z 549 (MH$^+$)
Its spectral data of the compound 6-12 are identical to those of compound 6-10.

Example 71

Preparation of N-[(2R)-2-(4-t-Butylbenzyl)-3-(pivaloyloxy)propyl]-(2S)-2-[3-chloro-4-(methylsulfonylamino)phenyl]propionamide (6-13, MK-453)

The N-[(2R)-2-(4-t-Butylbenzyl)-3-(pivaloyloxy)propyl]-(2S)-2-[3-chloro-4-(methylsulfonylamino)phenyl]propionamide was prepared by the similar procedure with that described in above Example 1-5.
92% yield, white solid, mp=61-63° C.
[α]−3.18 (c 1.0, CHCl$_3$)
$^1$H NMR (CDCl$_3$) δ 7.59 (d, 1H, J=8.4 Hz), 7.41 (d, 1H, J=2 Hz), 7.31 (d, 2H) 7.22 (dd, 1H, J=8.4, 2 Hz), 7.07 (d, 2H), 6.74 (bs, 1H), 5.93 (bt, 1H), 4.06 (dd, 1H, J=4, 11.3 Hz), 3.79 (dd, 1H, J=4.8, 11.3 Hz), 3.41 (q, 1H, J=7.1 Hz), 3.35 (ddd, 1H), 2.95-3.05 (m, 4H), 2.55 (d, 2H, J=7.5 Hz), 2.09 (m, 1H), 1.46 (d, 3H, J=7.1 Hz), 1.30 (s, 9H), 1.22 (s, 9H)
MS (FAB) m/z 566 (MH$^+$)

Example 72

Preparation of N-[(2S)-2-(4-t-Butylbenzyl)-3-(pivaloyloxy)propyl]-(2S)-2-[3-chloro-4-(methylsulfonylamino)phenyl]propionamide (6-14, MK-451)

The N-[(2S)-2-(4-t-Butylbenzyl)-3-(pivaloyloxy)propyl]-(2S)-2-[3-chloro-4-(methylsulfonylamino)phenyl]propionamide was prepared by the similar procedure with that described in above Example 1-5.

90% yield, white solid, mp=55-57° C.
[δ]=+3.24 (c 1.0, CHCl$_3$)
$^1$H NMR (CDCl$_3$) δ 7.61 (d, 1H, J=8.4 Hz), 7.42 (d, 1H, J=2 Hz), 7.30 (d, 2H), 7.23 (dd, 1H, J=8.4, 2 Hz), 7.05 (d, 2H), 6.72 (bs, 1H), 5.91 (bt, 1H), 4.09 (dd, 1H, J=4, 11.3 Hz), 3.81 (dd, 1H, J=5, 11.3 Hz), 3.43 (q, 1H, J=7.1 Hz), 3.34 (ddd, 1H), 2.95-3.08 (m, 4H), 2.53 (ddd of AB, 2H), 2.12 (m, 1H), 1.47 (d, 3H, J=7.1 Hz), 1.30 (s, 9H), 1.22 (s, 9H)
MS (FAB) m/z 566 (MH$^+$)

Example 73

Preparation of 2-[3-Fluoro-4-(methylsulfonylamino)phenyl]-2-methylpropionic acid (7-4, CHK-624)

Step 73-1. Preparation of Ethyl 2-(3-fluoro-4-nitrophenyl)-2-methylpropionamide (7-1, CHK-623)

To a stirred solution of ethyl 2-(4-amino-3-fluorophenyl)propionate compound (1-13, 10 mmol, 20 mmol) and NaH (12 mmol) in DMF (20 mL) was added a CH$_3$I (15 mmol) at 0° C. dropwise. After being stirred for 10 min at 0° C., the mixture was quenched by 1 N HCl solution, diluted with water and extracted with diethyl ether several times. The combined organic layers were washed with water and brine, dried over MgSO$_4$, and concentrated in vacuo. The residue was purified by flash column chromatography on silica gel using EtOAc:hexanes (1:10) as eluant to afford Ethyl 2-(3-fluoro-4-nitrophenyl)-2-methylpropionamide (7-1, CHK-623).

84% yield, yellow oil
$^1$H NMR (CDCl$_3$) δ 8.04 (dd, 1H, J=7.8, 8.5 Hz), 7.24-7.31 (m, 2H), 4.15 (q, 2H, J=7.1 Hz), 1.60 (s, 6H), 1.21 (t, 3H, J=7.1 Hz)

Step 73-2. Preparation of Ethyl 2-(4-amino-3-fluorophenyl)-2-methylpropionamide (7-2, CHK-633)

Through similar procedure to that in Example 1-2 excepting using Ethyl 2-(3-fluoro-4-nitrophenyl)-2-methylpropionamide (7-1), Ethyl 2-(4-amino-3-fluorophenyl)-2-methylpropionamide having following physicochemical properties was synthesized:

98% yield, redish oil
$^1$H NMR (CDCl$_3$) δ 7.01 (dd, 1H, J=2.2, 12.9 Hz), 6.93 (dd, 1H, J=2.2, 8.3 Hz), 6.75 (t, 1H, J=8.5 Hz), 4.10 (q, 2H, J=7.1 Hz), 3.62 (bs, 2H), 1.52 (s, 6H), 1.19 (t, 3H, J=7.1 Hz)

Step 73-3. Preparation of Ethyl 2-[3-fluoro-4-(methylsulfonylamino)phenyl]-2-methylpropionamide (7-3, CHK-654)

Through similar procedure to that in Example 1-3 excepting using Ethyl 2-(4-amino-3-fluorophenyl)-2-methylpropionamide (7-2), Ethyl 2-[3-fluoro-4-(methylsulfonylamino)phenyl]-2-methylpropionamide having following physicochemical properties was synthesized:

88% yield, white solid, mp=71-72° C.
$^1$H NMR (CDCl$_3$) δ 7.51 (t, 1H, J=8.3 Hz), 7.1-7.2 (m, 2H), 6.56 (bs, 1H), 4.13 (q, 2H, J=7.1 Hz), 3.04 (s, 1H), 1.56 (s, 6H), 1.20 (t, 3H, J=7.1 Hz)

Step 73-4. Preparation of 2-[3-Fluoro-4-(methylsulfonylamino)phenyl]-2-methylpropionic acid (74, CHK-624)

Through similar procedure to that in Example 1-4 excepting using Ethyl 2-[3-fluoro-4-(methylsulfonylamino)phenyl]-2-methylpropionamide (7-3), 2-[3-Fluoro-4-(methylsulfonylamino)phenyl]-2-methylpropionic acid having following physicochemical properties was synthesized:

88% yield, white solid, mp=152-153° C.
$^1$H NMR (CDCl$_3$) δ 7.53 (t, 1H, J=8.3 Hz), 7.18-7.25 (m, 2H), 6.59 (bs, 1H), 3.04 (s, 1H), 1.59 (s, 6H)

Example 74

Preparation of 2-[4-(methylsulfonylamino)phenyl]-2-methylpropionic acid (8-11, CHK-518)

Step 74-1. Preparation of 4-Nitrobenzonitrile (8-1)

4-Nitrobenzonitrile is commercially available (sigma Aldrich, No. N1,200-7)

Step 74-2. Preparation of Methyl(4-nitrophenyl)acetate (8-3, CHK-500)

To a stirred solution of 4-Nitrobenzonitrile (8-1) in MeOH was added a HCl 3-4 drops. After having a reflux for 10 hr, the mixture was concentrated in vacuo. The residue was purified by flash column chromatography on silica gel using EtOAc:hexanes (1:10) as eluant to afford Methyl(4-nitrophenyl)acetate (8-3, CHK-500).

82% yield, yellow solid, mp=49-50° C.
$^1$H NMR (CDCl$_3$) δ 8.15 (bd, 2H), 7.43 (bd, 2H), 3.71 (s, 2H), 3.69 (s, 3H)

Step 74-3. Preparation of Methyl 2-(4-nitrophenyl)-2-methylpropionamide (8-5, CHK-508)

Through similar procedure to that in Example 38-1 excepting using Ethyl Methyl (4-nitrophenyl)acetate (8-3), Methyl 2-(4-nitrophenyl)-2-methylpropionamide (8-5, CHK-508) having following physicochemical properties was synthesized:

95% yield, yellow oil
$^1$H NMR (CDCl$_3$) δ 8.18 (bd, 2H), 7.50 (bd, 2H), 3.72 (s, 3H), 1.63 (s, 6H)

Step 74-4. Preparation of Methyl 2-(4-aminophenyl)-2-methylpropionamide (8-7, CHK-509)

Through similar procedure to that in Example 1-2 excepting using Methyl 2-(4-nitrophenyl)-2-methylpropionamide (8-5), Methyl 2-(4-aminophenyl)-2-methylpropionamide (8-7, CHK-509) having following physicochemical properties was synthesized:
80% yield, yellow oil
$^1$H NMR (CDCl$_3$) δ 7.12 (bd, 2H), 6.66 (bd, 2H), 3.62 (s, 3H), 1.52 (s, 6H)

Step 74-5. Preparation of Methyl 2-[4-(methylsulfonylamino)phenyl]-2-methylpropionamide (8-9, CHK-516)

Through similar procedure to that in Example 1-3 excepting using Methyl 2-(4-aminophenyl)-2-methylpropionamide (8-7), Methyl 2-[4-(methylsulfonylamino)phenyl]-2-methylpropionamide (8-9, CHK-516) having following physicochemical properties was synthesized:
96% yield, yellow solid, mp=123-125° C.
$^1$H NMR (CDCl$_3$) δ 7.33 (bd, 2H), 7.18 (bd, 2H), 6.67 (bs, 1H), 3.66 (s, 3H), 3.02 (s, 3H), 1.57 (s, 6H)

Step 74-6. Preparation of 2-[4-(methylsulfonylamino)phenyl]-2-methylpropionic acid (8-11, CHK-518)

Through similar procedure to that in Example 1-4 excepting using Methyl 2-[4-(methylsulfonylamino)phenyl]-2-methylpropionamide (8-9), 2-[4-(methylsulfonylamino)phenyl]-2-methylpropionic acid (8-11, CHK-518) having following physicochemical properties was synthesized:
92% yield, yellow solid, mp=148-151° C.
$^1$H NMR (CDCl$_3$) δ 7.39 (bd, 2H), 7.19 (bd, 2H), 6.44 (bs, 1H), 3.02 (s, 3H), 1.60 (s, 6H)

Example 75

Preparation of 2-(3-methoxy-4-(methylsulfonylamino)phenyl)-2-methylpropionic acid (8-12, CHK-491)

Step 75-1. Preparation of 3-Methoxy-4-nitrobenzonitrile (8-2, CHK-78)

The 3-Methoxy-4-nitrobenzonitrile (8-2) on the market was prepared from 3-methoxybenzonitryl by previous literature procedure (Gallacher et al., *Biogenic Amines*, pp 49-62, 1995)
44% yield, yellow solid, mp=87-89° C.
$^1$H NMR (CDCl$_3$) δ 7.88 (d, 1H, J=8.3 Hz), 7.07 (d, 1H, J=1.7 Hz), 7.00 (dd, 1H, J=1.7, 8.3 Hz), 4.00 (s, 3H), 3.84 (s, 2H)

Step 75-2. Preparation of Methyl(3-methoxy-4-nitrophenyl)acetate (8-4, CHK-143)

Through similar procedure to that in Example 74-2 excepting using 3-Methoxy-4-nitrobenzonitrile (8-2), Methyl(3-methoxy-4-nitrophenyl)acetate (8-4, CHK-143) having following physicochemical properties was synthesized:
79% yield, yellow oil
$^1$H NMR (CDCl$_3$) δ 7.83 (d, 1H, J=8.3 Hz), 7.03 (d, 1H, J=1.7H), 6.94 (dd, 1H, J=1.7, 8.3 Hz), 3.97 (s, 3H), 3.73 (s, 3H), 3.69 (s, 2H)

Step 75-3. Preparation of Methyl 2-(3-methoxy-4-nitrophenyl)-2-methylpropionamide (8-6, CHK-469)

Through similar procedure to that in Example 73-1 excepting using Methyl(3-methoxy-4-nitrophenyl)acetate (8-4), Methyl 2-(3-methoxy-4-nitrophenyl)-2-methylpropionamide (8-6, CHK-469) having following physicochemical properties was synthesized:
82% yield, yellow oil
$^1$H NMR (CDCl$_3$) δ 7.80 (d, 1H, J=8.5 Hz), 7.00 (d, 1H, J=2 Hz), 6.96 (dd, 1H, J=2, 8.5 Hz), 3.93 (s, 3H), 3.65 (s, 3H), 1.58 (s, 6H)

Step 75-4. Preparation of Methyl 2-(3-methoxy-4-aminophenyl)-2-methylpropionamide (8-8, CHK-481)

Through similar procedure to that in Example 1-2 excepting using 2-(3-methoxy-4-nitrophenyl)-2-methylpropionamide (8-6), Methyl 2-(3-methoxy-4-aminophenyl)-2-methylpropionamide (8-8, CHK-481) having following physicochemical properties was synthesized:
82% yield, yellow oil
$^1$H NMR (CDCl$_3$) δ 6.75-6.80 (m, 2H), 6.66 (d, 1H, J=8.4 Hz), 3.84 (s, 3H), 3.63 (s, 3H), 1.54 (s, 6H)

Step 75-5. Preparation of Methyl 2-(3-methoxy-4-(methylsulfonylamino)phenyl)-2-methylpropionamide (8-10, CHK-489)

Through similar procedure to that in Example 1-3 excepting using Methyl 2-(3-methoxy-4-aminophenyl)-2-methylpropionamide (8-8), Methyl 2-(3-methoxy-4-(methylsulfonylamino)phenyl)-2-methylpropionamide (8-10, CHK-489) having following physicochemical properties was synthesized:
90% yield, yellow oil
$^1$H NMR (CDCl$_3$) δ 7.46 (d, 1H, J=8.4 Hz), 6.95 (dd, 1H, J=2, 8.4 Hz), 6.88 (d, 1H, J=2 Hz), 6.75 (bs, 1H), 3.88 (s, 3H), 3.67 (s, 3H), 2.96 (s, 3H), 1.57 (s, 6H)

Step 75-6. Preparation of 2-(3-methoxy-4-(methylsulfonylamino)phenyl)-2-methylpropionic acid (8-12, CHK-491)

Through similar procedure to that in Example 1-4 excepting using NaOH of Methyl 2-(3-methoxy-4-(methylsulfonylamino)phenyl)-2-methylpropionamide (8-10) as metal salt, 2-(3-methoxy-4-(methylsulfonylamino)phenyl)-2-methylpropionic acid (8-12, CHK-491) having following physicochemical properties was synthesized:
89% yield, white solid, mp=122-124° C.
$^1$H NMR (CDCl$_3$) δ 7.47 (d, 1H, J=8.3 Hz), 7.00 (dd, 1H, J=1.8, 8.3 Hz), 6.94 (d, 1H, J=1.8 Hz), 6.78 (bs, 1H), 3.88 (s, 3H), 2.96 (s, 3H), 1.60 (s, 6H)

Example 76

Preparation of N-[2-(3,4-Dimethylbenzyl)-3-pivaloyloxypropyl]-2-[4-(methylsulfonylamino)phenyl]-2-methylpropionamide (9-1, CHK-520)

Through similar procedure to that in Example 1-5 excepting using 2-[4-(methylsulfonylamino)phenyl]-2-methylpropionic acid (8-11), N-[2-(3,4-Dimethylbenzyl)-3-pivaloyloxypropyl]-2-[4-(methylsulfonylamino)phenyl]-2-methylpropionamide (9-1, CHK-520) having following physicochemical properties was synthesized:
89% yield, yellow solid, mp=126-130° C.
$^1$H NMR (CDCl$_3$) δ 7.34 (dd, 2H, J=8.3, 1 Hz), 7.18 (d, 2H, J=8.3, 1 Hz), 6.8-7.05 (m, 3H), 6.44 (bs, 1H), 5.60 (t, 1H), 3.95 (dt, 1H), 3.76 (ddd, 1H), 3.27 (m, 1H), 3.08 (m, 1H), 3.00 (d, 3H), 2.45-2.65 (m, 2H), 2.15-2.3 (m, 6H), 2.05 (m, 1H), 1.53 (s, 6H), 1.19 (d, 9H)

MS (FAB) m/z 517 (MH⁺)

Example 77

Preparation of N-[2-(3,4-Dimethylbenzyl)-3-pivaloyloxypropyl]-2-[3-fluoro-4-(methylsulfonylamino)phenyl]-2-methylpropionamide (9-2, CHK-543)

Through similar procedure to that in Example 1-5 excepting using 2-[3-Fluoro-4-(methylsulfonylamino)phenyl]-2-methylpropionic acid (7-4), N-[2-(3,4-Dimethylbenzyl)-3-pivaloyloxypropyl]-2-[3-fluoro-4-(methylsulfonylamino)phenyl]-2-methylpropionamide (9-2, CHK-543) having following physicochemical properties was synthesized:

82% yield, white solid, mp=53-55° C.

$^1$H NMR (CDCl$_3$) δ 7.52 (dt, 1H), 6.8-7.2 (m, 5H), 5.74 (t, 1H), 4.01 (dt, 1H), 3.77 (ddd, 1H), 3.28 (m, 1H), 2.95-3.15 (m, 4H), 2.45-2.65 (m, 2H), 2.15-2.3 (m, 6H), 2.05 (m, 1H), 1.52 (s, 6H), 1.20 (d, 9H)

MS (FAB) m/z 535 (MH⁺)

Example 78

Preparation of N-[2-(3,4-Dimethylbenzyl)-3-pivaloyloxypropyl]-2-[3-methoxy-4-(methylsulfonylamino)phenyl]-2-methylpropionamide (9-3, CHK-493)

Through similar procedure to that in Example 1-5 excepting using 2-[3-methoxy-4-(metylsulfonylamino)phenyl]-2-metylpropion acid (8-12), N-[2-(3,4-Dimethylbenzyl)-3-pivaloyloxypropyl]-2-[3-methoxy-4-(methylsulfonylamino)phenyl]-2-methylpropionamide (9-3, CHK-493) having following physicochemical properties was synthesized:

84% yield, white solid, mp=100-103° C.

$^1$H NMR (CDCl$_3$) δ 7.48 (dd, 1H, J=8.3, 2 Hz), 6.8-7.05 (m, 5H), 6.74 (bs, 1H), 5.61 (t, 1H), 3.95 (ddd, 1H), 3.86 (s, 3H), 3.75 (ddd, 1H), 3.26 (m, 1H), 3.06 (m, 1H), 2.96 (d, 3H), 2.45-2.65 (m, 2H), 2.15-2.3 (m, 6H), 2.05 (m, 1H), 1.54 (s, 6H), 1.19 (d, 9H)

MS (FAB) m/z 547 (MH⁺)

Example 79

Preparation of N-[3-(3,4-Dimethylphenyl)propyl]-2-[4-(methylsulfonylamino)phenyl]-2-methylpropionamide (9-4, CHK-591)

Through similar procedure to that in Example 1-5 excepting using 2-[4-(metylsulfonylamino)phenyl]-2-metylpropion acid (8-11), N-[3-(3,4-Dimethylphenyl)propyl]-2-[4-(methylsulfonylamino)phenyl]-2-methylpropionamide (9-4, CHK-591) having following physicochemical properties was synthesized:

83% yield, white solid, mp=138-139° C.

$^1$H NMR (CDCl$_3$) δ 7.33 (d, 2H), 7.19 (d, 2H), 7.01 (d, 1H, J=7.5 Hz), 6.8-6.88 (m, 2H), 5.17 (bt, 1H), 3.20 (dd, 2H), 3.01 (s, 3H), 2.47 (t, 2H, J=7.3 Hz), 2.21 (s, 6H), 1.71 (m, 2H), 1.51 (s, 6H)

MS (FAB) m/z 403 (MH⁺)

Example 80

Preparation of N-[3-(3,4-Dimethylphenyl)propyl]-2-[3-fluoro-4-(methylsulfonylamino)phenyl]-2-methylpropionamide (9-5, CHK-656)

Through similar procedure to that in Example 1-5 excepting using 2-[3-Fluoro-4-(methylsulfonylamino)phenyl]-2-methylpropionic acid (7-4), N-[3-(3,4-Dimethylphenyl)propyl]-2-[3-fluoro-4-(methylsulfonylamino)phenyl]-2-methylpropionamide (9-5, CHK-656) having following physicochemical properties was synthesized:

89% yield, white solid, mp=145-146° C.

$^1$H NMR (CDCl$_3$) δ 7.53 (t, 1H, J=8.3 Hz), 7.1-7.17 (m, 2H), 7.02 (d, 1H), 6.8-6.9 (m, 2H), 6.46 (bs, 1H), 5.18 (bt, 1H), 3.23 (dd, 2H), 3.03 (s, 3H), 2.49 (t, 2H, J=7.5 Hz), 2.22 (s, 6H), 1.74 (m, 2H), 1.49 (s, 6H)

MS (FAB) m/z 421 (MH⁺)

Example 81

Preparation of N-[3-(3,4-Dimethylphenyl)propyl]-2-[3-methoxy-4-(methylsulfonylamino)phenyl]-2-methylpropionamide (9-6, CHK-600)

Through similar procedure to that in Example 1-5 excepting using 2-(3-methoxy-4-(methylsulfonylamino)phenyl)-2-methylpropionic acid (8-12), N-[3-(3,4-Dimethylphenyl)propyl]-2-[3-methoxy-4-(methylsulfonylamino)phenyl]-2-methylpropionamide (9-6, CHK-600) having following physicochemical properties was synthesized:

86% yield, white solid, mp=93-95° C.

$^1$H NMR (CDCl$_3$) δ 7.48 (d, 1H), 6.75-7.05 (m, 6H), 5.18 (bt, 1H), 3.85 (s, 3H), 3.20 (dd, 2H), 2.96 (s, 3H), 2.46 (t, 2H, J=7.3 Hz), 2.21 (s, 6H), 1.71 (m, 2H), 1.52 (s, 6H)

MS (EI) m/z 432 (MH⁺)

Example 82

Preparation of N-(4-tert-Butylbenzyl)-2-[4-(methylsulfonylamino)phenyl]-2-methylpropionamide (9-7, CHK-715)

Through similar procedure to that in Example 1-5 excepting using 2-(3-methoxy-4-(methylsulfonylamino)phenyl)-2-methylpropionic acid (8-12), N-[3-(3,4-Dimethylphenyl)propyl]-2-[3-methoxy-4-(methylsulfonylamino)phenyl]-2-methylpropionamide (9-6, CHK-600) having following physicochemical properties was synthesized:

92% yield, white solid, mp=141-143° C.

$^1$H NMR (CDCl$_3$) δ 7.36 (d, 2H, J=8.5 Hz), 7.31 (d, 2H, J=7.9 Hz), 7.18 (d, 2H, J=8.5 Hz), 7.07 (d, 1H, J=7.9 Hz), 6.40 (bs, 1H), 5.46 (bt, 1H), 4.36 (d, 1H, J=5.7 Hz), 3.00 (s, 3H), 1.59 (s, 3H), 1.55 (s, 3H), 1.30 (s, 9H)

MS (FAB) m/z 403 (MH⁺)

Example 83

Preparation of N-(4-tert-Butylbenzyl)-2-[3-fluoro-4-(methylsulfonylamino)phenyl]-2-methylpropionamide (9-8, CHK-655)

Through similar procedure to that in Example 1-5 excepting using 2-[4-(methylsulfonylamino)phenyl]-2-methylpropionic acid (8-11), N-(4-tert-Butylbenzyl)-2-[3-fluoro-4-

(methylsulfonylamino)phenyl]-2-methylpropionamide (9-8, CHK-655) having following physicochemical properties was synthesized:

74% yield, white solid, mp=48-51° C.

$^1$H NMR (CDCl$_3$) δ 7.53 (t, 1H, J=8.2 Hz), 7.33 (d, 2H), 7.17 (d, 1H), 7.09 (d, 1H), 6.45 (bs, 1H), 5.50 (bt, 1H), 4.37 (d, 1H, J=5.5 Hz), 3.03 (s, 3H), 1.58 (s, 3H), 1.55 (s, 3H), 1.30 (s, 9H)

MS (FAB) m/z 421 (MH$^+$)

Example 84

Preparation of N-(4-tert-Butylbenzyl)-2-[3-methoxy-4-(methylsulfonylamino)phenyl]-2-methylpropionamide (9-9, CHK-1001)

Through similar procedure to that in Example 1-5 excepting using 2-(3-methoxy-4-(methylsulfonylamino)phenyl)-2-methylpropionic acid (8-12), N-(4-tert-Butylbenzyl)-2-[3-methoxy-4-(methylsulfonylamino)phenyl]-2-methylpropionamide (9-9, CHK-1001) having following physicochemical properties was synthesized:

76% yield, white solid, mp=56-58° C.

$^1$H NMR (CDCl$_3$) δ 7.46 (d, 1H), 7.30 (d, 2H), 7.09 (d, 2H), 6.98 (dd, 1H), 6.83 (d, 1H), 6.83 (d, 1H), 6.77 (bs, 1H), 5.55 (bt, 1H), 4.36 (d, 1H), 3.80 (s, 3H), 2.94 (s, 3H), 1.59 (s, 6H), 1.29 (s, 9H)

Example 85

Preparation of 1-[3-fluoro-4-(methylsulfonylamino)phenyl]cyclopropanecarboxylic acid (10-5, CHK-996)

Step 85-1. Preparation of methyl 2-(3-fluoro-4-nitophenyl)acetate (10-1, CHK-947)

To a stirred slowly solution of nitric acid (11.48 mM, 0.49 mL) was added a mixture of 3-fluorophenyl acetate (11.48 mM, 1930 mg) on the market and H$_2$SO$_4$ (3 mmol) at 0° C. dropwise. After being stirred for 2 hr, the mixture was diluted with iced-water and extracted with ethyl acetate. The combined organic layers were washed with water. The residue was purified by flash column chromatography on silica gel using EtOAc:hexanes (1:4) as eluant to afford metyl 2-(3-fluoro-4-nitophenyl)acetate (10-1, CHK-947).

76% yield, 321 mg $^1$H NMR (CDCl$_3$) δ 8.02 (t, 1H), 7.15-7.30 (m, 2H), 3.73 (s, 3H), 3.70 (s, 2H)

Step 85-2. Preparation of methyl 1-(3-fluoro-4-nitophenyl)cycloprophancarboxylate (10-2, CHK-987)

To a stirred solution of methyl 2-(3-fluoro-4-nitrophenyl)acetate (10-1, 300 mg, 1.41 mmol) in anhydrous THF (6 mL) was added NaH (14.1 mM, 338 mg) slowly. The mixture was stirred for 10 min and then dibromoethane (7.05 mM, 0.6 mL) was added. The reaction mixture was allowed to be warmed to room temperature for 30 min and quenched by saturated NH$_4$Cl solution. After aqueous work-up, the residue was purified by flash column chromatography with EtOAc:hexanes (1:5) as eluant to afford methyl 1-(3-fluoro-4-nitophenyl)cycloprophancarboxylate (10-2, CHK-987).

76% yield, white solid, mp=56-58° C.

$^1$H NMR (CDCl$_3$) δ 7.47 (dt, 1H), 7.15-7.30 (m, 2H), 3.66 (s, 3H), 1.68 (dd, 2H), 1.19 (dd, 2H)

Step 85-3. Preparation of methyl 1-(4-amino-3-fluorophenyl)cycloprophancarboxylate (10-3, CHK-993)

Through similar procedure to that in Example 1-2 excepting using methyl 1-(3-fluoro-4-nitrophenyl)cycloprophancarboxylate (10-2) with the corresponding 4-chlorobenzylamine compound as a starting material, methyl 1-(4-amino-3-fluorophenyl)cycloprophancarboxylate (10-3, CHK-993) having following physicochemical properties was synthesized:

$^1$H NMR (CDCl$_3$) δ 6.9-7.0 (m, 2H), 6.64 (m, 1H), 3.89 (bs, 2H), 3.65 (s, 3H), 1.68 (dd, 2H), 1.18 (dd, 2H)

Step 85-4. Preparation of Methyl 1-(4-amino-3-fluorophenyl)cyclopropanecarboxylate (104)

Through similar procedure to that in Example 1-3 excepting using methyl 1-(4-amino-3-fluorophenyl)cycloprophancarboxylate (10-3) with the corresponding 4-chlorobenzylamine compound as a starting material, Methyl 1-(4-amino-3-fluorophenyl)cyclopropanecarboxylate (10-4) having following physicochemical properties was synthesized:

$^1$H NMR (CDCl$_3$) δ 7.05-7.23 (m, 3H), 6.51 (bs, 1H), 3.68 (s, 3H), 3.31 (s, 3H), 1.77 (dd, 2H), 1.34 (dd, 2H)

Step 85-5. Preparation of Methyl 1-[3-fluoro-4-(methylsulfonylamino)phenyl]cyclopropanecarboxylate (10-5)

Through similar procedure to that in Example 1-5 excepting using Methyl 1-(4-amino-3-fluorophenyl)cyclopropanecarboxylate (10-4) with the corresponding 4-chlorobenzylamine compound as a starting material, Methyl 1-[3-fluoro-4-(methylsulfonylamino)phenyl]cyclopropanecarboxylate (10-5) having following physicochemical properties was synthesized:

$^1$H NMR (CDCl$_3$) δ 7.05-7.25 (m, 3H), 6.50 (bs, 1H), 3.30 (s, 3H), 1.76 (dd, 2H), 1.33 (dd, 2H)

MS (FAB) m/z 421 (MH$^+$)

Example 86

Preparation of 1-[4-(Methylsulfonylamino)phenyl]cyclopropanecarboxylic acid (11-7, CHK-530)

Step 86-1. Preparation of Methyl 1-(4-nitrophenyl)cyclopropanecarboxylate (11-1, CHK-521)

Through similar procedure to that in Example 85-2 excepting using Methyl(4-nitrophenyl)acetate (8-3) as a starting material, Methyl 1-(4-nitrophenyl)cyclopropanecarboxylate (11-1, CHK-521) having following physicochemical properties was synthesized:

71% yield, yellow solid, mp=89-91° C.

$^1$H NMR (CDCl$_3$) δ 8.18 (bd, 2H), 7.51 (bd, 2H), 3.65 (s, 3H), 1.71 (dd, 2H), 1.24 (dd, 2H)

Step 86-2. Preparation of Methyl 1-(4-aminophenyl)cycloropanecarboxylate (11-3, CHK-525)

Through similar procedure to that in Example 1-2 excepting using Methyl 1-(4-nitrophenyl)cyclopropanecarboxylate (11-1) as a starting material, Methyl 1-(4-aminophenyl)cyclopropanecarboxylate (11-3, CHK-525) having following physicochemical properties was synthesized:

93% yield, yellow solid, mp=62-65° C.
$^1$H NMR (CDCl$_3$) δ 7.12 (bd, 2H), 6.63 (bd, 2H), 3.65 (bs, 2H), 3.61 (s, 3H), 1.54 (dd, 2H), 1.13 (dd, 2H)

Step 86-3. Preparation of Methyl 1-[4-(methylsulfonylamino)phenyl]cyclopropanecarboxylate (11-5, CHK-527)

Through similar procedure to that in Example 1-3 excepting using Methyl 1-(4-aminophenyl)cyclopropanecarboxylate (11-3) as a starting material, Methyl 1-[4-(methylsulfonylamino)phenyl]cyclopropanecarboxylate (11-5, CHK-527) having following physicochemical properties was synthesized:
88% yield, white solid, mp=118-120° C.
$^1$H NMR (CDCl$_3$) δ 7.33 (bd, 2H), 7.15 (bd, 2H), 6.36 (bs, 1H), 3.63 (s, 2H), 3.03 (s, 3H), 1.62 (dd, 2H), 1.17 (dd, 2H)

Step 86-3. Preparation of Methyl 1-[4-(Methylsulfonylamino)phenyl]cyclopropanecarboxylic acid (11-7, CHK-530)

Through similar procedure to that in Example 1-4 excepting using Methyl 1-[4-(methylsulfonylamino)phenyl]cyclopropanecarboxylate (11-5) as a starting material, Methyl 1-[4-(Methylsulfonylamino)phenyl]cyclopropanecarboxylic acid (11-7, CHK-530) having following physicochemical properties was synthesized:
98% yield, yellow solid, mp=220-224° C.
$^1$H NMR (DMSO-d$_6$) δ 9.69 (bs, 1H, CO$_2$H), 7.26 (bd, 2H), 7.10 (bd, 2H), 2.96 (s, 3H), 1.41 (dd, 2H), 1.08 (dd, 2H)

Example 87

Preparation of 1-[3-Methoxy-4-(methylsulfonylamino)phenyl]cyclopropanecarboxylic acid (11-8, CHK-539)

Step 87-1. Preparation of Methyl 1-(3-methoxy-4-nitrophenyl)cyclopropanecarboxylate (11-2, CHK-528)

Through similar procedure to that in Example 85-2 excepting using Methyl(3-methoxy-4-nitrophenyl)acetate (8-4) as a starting material, Methyl 1-(3-methoxy-4-nitrophenyl)cyclopropanecarboxylate (11-2, CHK-528) having following physicochemical properties was synthesized:
70% yield, yellow oil
$^1$H NMR (CDCl$_3$) δ 7.81 (d, 1H, J=8.3 Hz), 7.07 (d, 1H, J=1.5 Hz), 7.00 (dd, 1H, J=8.3, 1.5 Hz), 3.97 (s, 3H), 3.65 (s, 3H), 1.68 (dd, 2H), 1.23 (dd, 2H)

Step 87-2. Preparation of Methyl 1-(4-amino-3-methoxyphenyl)cyclopropanecarboxylate (11-4, CHK-531)

Through similar procedure to that in Example 1-2 excepting using Methyl 1-(3-methoxy-4-nitrophenyl)cyclopropanecarboxylate (11-2) as a starting material, Methyl 1-(4-amino-3-methoxyphenyl)cyclopropanecarboxylate (11-4, CHK-531) having following physicochemical properties was synthesized:
92% yield, redish oil
$^1$H NMR (CDCl$_3$) δ 6.6-6.8 (m, 3H), 3.85 (s, 3H), 3.77 (bs, 2H), 3.62 (s, 3H), 1.55 (dd, 2H), 1.15 (dd, 2H)

Step 87-3. Preparation of Methyl 1-[3-methoxy-4-(methylsulfonylamino)phenyl]cyclopropanecarboxylate (11-6, CHK-534)

Through similar procedure to that in Example 1-3 excepting using Methyl 1-(4-amino-3-methoxyphenyl)cyclopropanecarboxylate (11-4) as a starting material, Methyl 1-[3-methoxy-4-(methylsulfonylamino)phenyl]cyclopropanecarboxylate (11-6, CHK-534) having following physicochemical properties was synthesized:
92% yield, redish oil
$^1$H NMR (CDCl$_3$) δ 6.6-6.8 (m, 3H), 3.85 (s, 3H), 3.77 (bs, 2H), 3.62 (s, 3H), 1.55 (dd, 2H), 1.15 (dd, 2H)

Step 87-4. Preparation of 1-[3-Methoxy-4-(methylsulfonylamino)phenyl]cyclopropanecarboxylic acid (11-8, CHK-539)

Through similar procedure to that in Example 1-3 excepting using Methyl 1-[3-methoxy-4-(methylsulfonylamino)phenyl]cyclopropanecarboxylate (11-6) as a starting material, 1-[3-Methoxy-4-(methylsulfonylamino)phenyl]cyclopropanecarboxylic acid (11-8, CHK-539) having following physicochemical properties was synthesized:
92% yield, redish oil
$^1$H NMR (CDCl$_3$) δ 6.6-6.8 (m, 3H), 3.85 (s, 3H), 3.77 (bs, 2H), 3.62 (s, 3H), 1.55 (dd, 2H), 1.15 (dd, 2H)

Example 88

Preparation of N-[2-(3,4-Dimethylbenzyl)-3-pivaloyloxypropyl]-1-[4-(methylsulfonylamino)phenyl]cyclopropanecarboxamide (12-1, CHK-533)

Through similar procedure to that in Example 1-5 excepting using 1-[4-(Methylsulfonylamino)phenyl]cyclopropanecarboxylic acid (11-7) as a starting material, N-[2-(3,4-Dimethylbenzyl)-3-pivaloyloxypropyl]-1-[4-(methylsulfonylamino)phenyl]cyclopropanecarboxamide (12-1, CHK-533) having following physicochemical properties was synthesized:
80% yield, white solid, mp=54-56° C.
$^1$H NMR (CDCl$_3$) δ 7.38 (d, 2H, J=8.3 Hz), 7.21 (d, 2H, J=8.3 Hz), 6.75-7.05 (m, 3H), 6.37 (bs, 1H), 5.56 (bs, 1H), 3.93 (m, 1H), 3.76 (m, 1H), 3.27 (m, 1H), 2.95-3.1 (m, 4H), 2.4-2.6 (m, 2H), 2.15-2.3 (m, 6H), 2.05 (m, 1H), 1.58 (m, 2H), 1.17 (s, 9H), 1.00 (m, 2H)
MS (FAB) m/z 515 (MH$^+$)

Example 89

Preparation of N-[2-(3,4-Dimethylbenzyl)-3-pivaloyloxypropyl]-1-[3-fluoro-4-(methylsulfonylamino)phenyl]cyclopropanecarboxamide (12-2, CHK-538)

Through similar procedure to that in Example 1-5 excepting using 1-[3-fluoro-4-(methylsulfonylamino)phenyl]cyclopropanecarboxylic acid (10-6) as a starting material, N-[2-(3,4-Dimethylbenzyl)-3-pivaloyloxypropyl]-1-[3-fluoro-4-(methylsulfonylamino)phenyl]cyclopropanecarboxamide (12-2, CHK-538) having following physicochemical properties was synthesized:
white solid, mp=55-56° C.
$^1$H NMR (CDCl$_3$) δ 7.48 (t, 1H), 7.1-7.2 (m, 2H), 6.75-7.05 (m, 3H), 6.39 (bs, 1H), 5.58 (bs, 1H), 3.92 (m, 1H), 3.77

(m, 1H), 3.25 (m, 1H), 2.9-3.1 (m, 4H), 2.4-2.6 (m, 2H), 2.15-2.3 (m, 6H), 2.07 (m, 1H), 1.58 (m, 2H), 1.18 (s, 9H), 1.02 (m, 2H)
MS (FAB) m/z 533 (MH$^+$)

Example 90

Preparation of N-[2-(3,4-Dimethylbenzyl)-3-pivaloyloxypropyl]-1-[3-methoxy-4-(methylsulfonylamino)phenyl]cyclopropanecarboxamide (12-3, CHK-541)

Through similar procedure to that in Example 1-5 excepting using 1-[3-fluoro-4-(methylsulfonylamino)phenyl]cyclopropanecarboxylic acid (10-6) as a starting material, N-[2-(3,4-Dimethylbenzyl)-3-pivaloyloxypropyl]-1-[3-methoxy-4-(methylsulfonylamino)phenyl]cyclopropanecarboxamide (12-3, CHK-541) having following physicochemical properties was synthesized:
82% yield, white solid, mp=66-68° C.
$^1$H NMR (CDCl$_3$) δ 7.50 (dd, 1H, J=8.3, 1.3 Hz), 6.75-7.05 (m, 6H), 5.65 (bt, 1H), 3.94 (m, 1H), 3.90 (s, 3H), 3.76 (m, 1H), 3.29 (m, 1H), 2.9-3.1 (m, 4H), 2.4-2.6 (m, 2H), 2.15-2.3 (m, 6H), 2.05 (m, 1H), 1.58 (m, 2H), 1.16 (d, 9H), 1.02 (m, 2H)
MS (FAB) m/z 545 (MH$^+$)

Example 91

Preparation of N-[3-(3,4-Dimethylphenyl)propyl]-1-[4-(methylsulfonylamino)phenyl]cyclopropanecarboxamide (12-4, CHK-590)

Through similar procedure to that in Example 1-5 excepting using 1-[4-(Methylsulfonylamino)phenyl]cyclopropanecarboxylic acid (11-7) as a starting material, N-[3-(3,4-Dimethylphenyl)propyl]-1-[4-(methylsulfonylamino)phenyl]cyclopropanecarboxamide (12-4, CHK-590) having following physicochemical properties was synthesized:
81% yield, white solid, mp=127-128° C.
$^1$H NMR (CDCl$_3$) δ 7.37 (m, 2H, J=8.3 Hz), 7.19 (m, 2H, J=8.3 Hz), 6.75-7.05 (m, 3H), 6.40 (bs, 1H), 5.25 (bs, 1H), 3.17 (dd, 2H), 3.06 (s, 3H), 2.46 (t, 2H, J=7.3 Hz), 2.21 (s, 6H), 1.68 (m, 2H), 1.59 (dd, 2H), 0.99 (dd, 2H)
MS (FAB) m/z 401 (MH$^+$)

Example 92

Preparation of N-[3-(3,4-Dimethylphenyl)propyl]-1-[3-fluoro-4-(methylsulfonylamino)phenyl]cyclopropanecarboxamide (12-5)

Through similar procedure to that in Example 1-5 excepting using 1-[3-fluoro-4-(methylsulfonylamino)phenyl]cyclopropanecarboxylic acid (10-6) as a starting material, N-[3-(3,4-Dimethylphenyl)propyl]-1-[3-fluoro-4-(methylsulfonylamino)phenyl]cyclopropanecarboxamide (12-5) having following physicochemical properties was synthesized:
81% yield, white solid, mp=127-128° C.
$^1$H NMR (CDCl$_3$) δ 7.50 (t, 1H), 7.1-7.2 (m, 2H), 6.8-7.1 (m, 3H), 6.40 (bs, 1H), 5.30 (bs, 1H), 3.16 (dd, 2H), 3.05 (s, 3H), 2.48 (t, 2H), 2.25 (s, 6H), 1.69 (m, 2H), 1.60 (m, 2H), 1.00 (dd, 2H)
MS (FAB) m/z 419 (MH$^+$)

Example 93

Preparation of N-[3-(3,4-Dimethylphenyl)propyl]-1-[3-methoxy-4-(methylsulfonylamino)phenyl]cyclopropanecarboxamide (12-6, CHK-632)

Through similar procedure to that in Example 1-5 excepting using 1-[3-Methoxy-4-(methylsulfonylamino)phenyl]cyclopropanecarboxylic acid (11-8) as a starting material, N-[3-(3,4-Dimethylphenyl)propyl]-1-[3-methoxy-4-(methylsulfonylamino)phenyl]cyclopropanecarboxamide (12-6, CHK-632) having following physicochemical properties was synthesized:
87% yield, white solid, mp=88-89° C.
$^1$H NMR (CDCl$_3$) δ 7.50 (d, 1H, J=8.1 Hz), 6.75-7.05 (m, 6H), 5.34 (t, 1H), 3.88 (s, 3H), 3.18 (dd, 2H), 3.00 (s, 3H), 2.47 (t, 2H, J=7.5 Hz), 2.21 (s, 6H), 1.69 (m, 2H), 1.59 (dd, 2H), 1.01 (dd, 2H)
MS (FAB) m/z 431 (MH$^+$)

Example 94

Preparation of N-(4-tert-Butylbenzyl)-1-[4-(methylsulfonylamino)phenyl]cyclopropanecarboxamide (12-7, CHK-719)

Through similar procedure to that in Example 1-5 excepting using 1-[4-(Methylsulfonylamino)phenyl]cyclopropanecarboxylic acid (11-7) as a starting material, N-(4-tert-Butylbenzyl)-1-[4-(methylsulfonylamino)phenyl]cyclopropanecarboxamide (12-7, CHK-719) having following physicochemical properties was synthesized:
90% yield, white solid, mp=200-203° C.
$^1$H NMR (DMSO-d$_6$) δ 9.75 (bs, 1H), 4.15 (d, 2H, J=6 Hz), 2.98 (s, 3H), 1.32 (dd, 2H), 1.25 (s, 9H), 0.94 (dd, 2H)
MS (FAB) m/z 401 (MH$^+$)

Example 95

Preparation of N-(4-tert-Butylbenzyl)-1-[3-fluoro-4-(methylsulfonylamino)phenyl]cyclopropanecarboxamide (12-8, CHK-998)

Through similar procedure to that in Example 1-5 excepting using Methyl 1-[3-fluoro-4-(methylsulfonylamino)phenyl]cyclopropanecarboxylate (10-5) as a starting material, N-(4-tert-Butylbenzyl)-1-[3-fluoro-4-(methylsulfonylamino)phenyl]cyclopropanecarboxamide (12-8, CHK-998) having following physicochemical properties was synthesized:
90% yield, white solid, mp=200-203° C.
$^1$H NMR (CDCl$_3$) δ 9.75 (bs, 1H), 4.15 (d, 2H, J=6 Hz), 2.98 (s, 3H), 1.32 (dd, 2H), 1.25 (s, 9H), 0.94 (dd, 2H)
MS (FAB) m/z 401 (MH$^+$)

Example 96

Preparation of N-(4-tert-Butylbenzyl)-1-[3-methoxy-4-(methylsulfonylamino)phenyl]cyclopropanecarboxamide (12-9, CHK-718)

Through similar procedure to that in Example 1-5 excepting using 1-[3-Methoxy-4-(methylsulfonylamino)phenyl]cyclopropanecarboxylic acid (11-8) as a starting material, N-(4-tert-Butylbenzyl)-1-[3-methoxy-4-(methylsulfonylamino)phenyl]cyclopropanecarboxamide (12-9, CHK-718) having following physicochemical properties was synthesized:

90% yield, white solid, mp=200-203° C.

$^1$H NMR (CDCl$_3$) δ 7.48 (d, 1H), 7.31 (bd, 2H), 7.09 (bd, 2H), 7.03 (dd, 1H), 6.94 (bs, 1H), 6.80 (bs, 1H), 5.67 (bt, 1H), 4.36 (d, 2H), 3.86 (s, 3H), 2.97 (s, 3H), 1.65 (dd, 2H), 1.29 (s, 9H), 1.06 (dd, 2H)

MS (FAB) m/z 431 (MH$^+$)

Example 97

Preparation of 1-[4-(Methylsulfonylamino)phenyl]ethyl amine (13-11, LJO-302)

Step 97-1. Preparation of 4'-(Methylsulfonylamino)acetophenone (13-5, LJO-298)

A cooled solution of 4'-aminoacetophenon (10 mmol) in pyridine (10 mL) at 0° C. was treated with methanesulfonyl chloride (15 mmol) and stirred at room temperature for 2 h. The reaction mixture was diluted with H$_2$O and extracted with EtOAc several times. The combined organic layers were washed with H$_2$O and brine, dried over MgSO$_4$, filtered, and the filtrate was concentrated in vacuo. The residue was purified by flash column chromatography on silica gel using EtOAc:hexanes to afford 4'-(Methylsulfonylamino)acetophenone (13-5, LJO-298).

95% yield, mp=161° C.

$^1$H NMR (CDCl$_3$) δ 7.97 (dd, 2H, J=2, 6.8 Hz), 7.26 (dd, 2H, J=2, 6.8 Hz), 6.87 (bs, 1H), 3.10 (s, 3H), 2.59 (s, 3H)

Step 97-2. Preparation of 4'-(Methylsulfonylamino)acetophenone oxime (13-8, LJO-299)

A mixture of 4'-(Methylsulfonylamino)acetophenone (13-5, 5 mmol) and hydroxylamine hydrochloride (0.695 g, 10 mmol) in pyridine (5 mL) was heated at 70° C. for 3 h. The reaction mixture was cooled to room temperature, diluted with H$_2$O, and extracted with EtOAc several times. The combined organic layers were washed with H$_2$O and brine, dried over MgSO$_4$, filtered, and the filtrate was concentrated in vacuo. The residue was purified by flash column chromatography on silica gel using EtOAc:hexanes (1:1) as eluant to 4'-Methylsulfonylamino)acetophenone oxime (13-8, LJO-299).

91% yield, white solid, mp=180° C.

$^1$H NMR (CDCl$_3$) δ 7.65 (dd, 2H, J=2, 6.6 Hz), 7.29 (s, 1H), 7.20 (dd, 2H, J=2, 6.8 Hz), 6.43 (bs, 1H), 3.03 (s, 3H), 2.26 (s, 3H)

Step 97-3. Preparation of 1-[4-(Methylsulfonylamino)phenyl]ethyl amine (13-11, LJO-302)

A suspension of 4'-(Methylsulfonylamino)acetophenone oxime (13-8, 5 mmol) and 10% palladium on carbon (150 mg) in MeOH (25 mL) was treated with concentrated hydrochloric acid (10 drops) was hydrogenated under a balloon of hydrogen for 6 h. The reaction mixture was neutralized with solid NaHCO$_3$, filtered and the filtrate was concentrated in vacuo. The residue was purified by flash column chromatography on silica gel using CH$_2$Cl$_2$:MeOH as eluant to afford 1-[4-(Methylsulfonylamino)phenyl]ethyl amine (13-11, LJO-302).

99% yield, white solid, mp=211° C.

$^1$H NMR (CDCl$_3$) δ 7.35 (d, 2H, J=8.6 Hz), 7.18 (d, 2H, J=8.6 Hz), 4.13 (q, 1H, J=7 Hz), 3.00 (s, 3H), 1.37 (d, 3H, J=7 Hz)

Example 98

Preparation of 1-[3-Fluoro-4-(methylsulfonylamino)phenyl]ethyl amine (13-12, MK-232)

Step 98-1. Preparation of N-(2-Fluoro-4-iodophenyl)methanesulfonamide (13-3. SH-14)

Through similar procedure to that in Example 97-1 excepting using 2-Fluoro-4-iodoanylin (13-1) as a starting material, N-(2-Fluoro-4-iodophenyl)methanesulfonamide (13-3, SH-14) having following physicochemical properties was synthesized:

96% yield, white solid, mp=123° C.

$^1$H NMR (CDCl$_3$) δ 7.43 (bd, 2H), 7.26 (t, 1H, J=8.3 Hz), 6.58 (bs, 1H), 2.97 (s, 3H)

Step 98-2. Preparation of 3'-Fluoro-4'-(methylsulfonylamino)acetophenone (13-6, LJO-363)

A mixture of N-(2-Fluoro-4-iodophenyl)methanesulfonamide (13-3, 5 mmol) and palladium(II)acetate (0.15 nM, 0.034 g), 1,3-bisdiphenyl phosphinoprophan (0.3 mM, 0.124 g), thallium(I)acetate (5.5 mM, 1.450 g) and butylvinyl ether (10 mM, 1.3 mL) in DMF (10 mL) was heated at 95° C. for 19 h. The reaction mixture was cooled to room temperature, diluted with THF, treated with 10% HCl (10 mL) and stirred at room temperature. A mixture was diluted with EtOAc, washed with ammonium chloride solution three times and concentrated in vacuo. The residue was purified by flash column chromatography on silica gel using EtOAc:hexanes as eluant to 3'-Fluoro-4'-(methylsulfonylamino)acetophenone (13-6, LJO-363).

78% yield, yellow solid, mp=141° C.

$^1$H NMR (CDCl$_3$) δ 7.65-7.80 (m, 3H), 6.89 (bs, 1H), 3.12 (s, 3H), 2.59 (s, 3H)

Step 98-3. Preparation of 3'-fluoro-4'-(methylsulfonylamino)acetophenone oxime (13-9, LJO-327)

Through similar procedure to that in Example 97-2 excepting using 3'-Fluoro-4'-(methylsulfonylamino)acetophenone (13-6) as a starting material, 3'-fluoro-4'-(methylsulfonylamino)acetophenone oxime (13-9, LJO-327) having following physicochemical properties was synthesized:

87% yield, white solid, mp=173° C.

$^1$H NMR (CDCl$_3$) δ 7.59 (t, 1H, J=8.3 Hz), 7.4-7.52 (m, 2H), 6.60 (bs, 1H), 3.05 (s, 3H), 2.25 (s, 3H)

Step 98-4. Preparation of 1-[3-Fluoro-4-(methylsulfonylamino)phenyl]ethyl amine (13-12, MK-232)

Through similar procedure to that in Example 97-3 excepting using 3'-fluoro-4'-(methylsulfonylamino)acetophenone oxime (13-9) as a starting material, 3'-Fluoro-4-(methylsulfonylamino)phenyl]ethyl amine (13-12, MK-232) having following physicochemical properties was synthesized:

98% yield, white solid, mp=160-167° C.

$^1$H NMR (CD$_3$OD) δ 7.45 (t, 2H, J=8.2 Hz), 7.24 (dd, 1H, J=11.5, 2 Hz), 7.18 (dd, 1H, J=8.3, 2 Hz), 4.15 (q, 1H, J=7 Hz), 2.97 (s, 3H), 1.43 (d, 3H, J=7 Hz)

Example 99

Preparation of 1-[3-(Methoxycarbonyl)-4-(methylsulfonylamino)phenyl]ethyl amine (13-13, YHS-181)

Step 99-1. Preparation of N-(2-Fluoro-4-iodophenyl)methanesulfonamide (13-3, SH-14)

A solution of 2-amino-4-iodinebenzonic acid (11 mM) in MeOH (50 mL) was added HCl (20 mmol) and H$_2$SO$_4$ (2 mmol). The reaction mixture was refluxed and concentrated for a night, diluted with NaHCO$_3$ and filtered with MgSO$_4$ several times. The combined organic layers were washed with water, dried over MgSO$_4$, filtered, and the filtrate was concentrated in vacuo. The residue was purified by flash column chromatography on silica gel using EtOAc:hexanes to afford N-(2-Fluoro-4-iodophenyl)methanesulfonamide (13-3, SH-14).

50% yield (13-2) $^1$H NMR (CDCl$_3$) δ 8.34 (d, 1H, J=2.2 Hz), 7.80 (dd, 1H, J=2.2, 8.8 Hz), 7.50 (d, 1H, J=8.8 Hz), 3.93 (s, 3H), 3.04 (s, 3H)

(13-4) $^1$H NMR (CDCl$_3$) δ 8.34 (d, 1H, J=2.2 Hz), 7.80 (dd, 1H, J=2.2, 8.8 Hz), 7.50 (d, 1H, J=8.8 Hz), 3.93 (s, 3H), 3.04 (s, 3H)

Step 99-2. Preparation of 3-(Methoxycarbonyl)-4'-(methylsulfonylamino)acetophenone (13-7, YHS-176)

Through similar procedure to that in Example 98-2 excepting using N-[4-Iodo-2-(methoxycarbonyl)phenyl]methanesulfonamide (13-4, YHS-27) as a starting material, 3-(Methoxycarbonyl)-4'-(methylsulfonylamino)acetophenone (13-7, YHS-176) having following physicochemical properties was synthesized:

60% yield, pale yellow solid, mp=112-115° C.

$^1$H NMR (CDCl$_3$) δ 8.67 (d, 1H, J=2 Hz), 8.14 (dd, 1H, J=2, 8.6 Hz), 7.82 (d, 1H, J=8.6 Hz), 3.99 (s, 3H), 3.15 (s, 3H), 2.61 (s, 3H)

Step 99-3. Preparation of 3'-(Methoxycarbony)-4'-(methylsulfonylamino)acetophenone oxime (13-10, YHS-180)

Through similar procedure to that in Example 97-2 excepting using 3-(Methoxycarbonyl)-4'-(methylsulfonylamino)acetophenone (13-7) as a starting material, 3'-(Methoxycarbony)-4'-(methylsulfonylamino)acetophenone oxime (13-10, YHS-180) having following physicochemical properties was synthesized:

82% yield, white solid, mp=136-137° C.

$^1$H NMR (CDCl$_3$) δ 10.54 (bs, 1H), 8.32 (d, 1H, J=2.2 Hz), 7.85 (dd, 1H, J=2.2, 8.8 Hz), 7.76 (d, 1H, J=8.8 Hz), 3.96 (s, 3H), 3.09 (s, 3H), 2.29 (s, 3H)

Step 99-4. Preparation of 1-[3-(Methoxycarbonyl)-4-(methylsulfonylamino)phenyl]ethyl amine (13-13. YHS-181)

Through similar procedure to that in Example 97-3 excepting using 3'-(Methoxycarbony)-4'-(methylsulfonylamino) acetophenone oxime (13-10) as a starting material, 1-[3-(Methoxycarbonyl)-4-(methylsulfonylamino)phenyl]ethyl amine (13-13, YHS-181) having following physicochemical properties was synthesized:

65% yield, colorless oil $^1$H NMR (CDCl$_3$) δ 8.07 (d, 1H, J=2.2 Hz), 7.70 (d, 1H, J=8.6 Hz), 7.58 (dd, 1H, J=2.2, 8.6 Hz), 4.18 (q, 1H, J=6.6 Hz), 3.94 (s, 3H), 3.05 (s, 3H), 1.41 (d, 3H, J=6.6 Hz)

Example 100

Preparation of 1-[3-Methoxy-4-(methylsulfonylamino)phenyl]ethyl amine (14-3, CHK-570)

Step 100-1. Preparation of Benzyl N-{1-[3-methoxy-4-(methylsulfonylamino)phenyl]ethyl}carbamate (14-1, CHK-567)

A 2-(3-methoxy-4-methylsulfonylamino)propion acid (260 mg) in toluene (4 mL) was added diphenylphosphoryl azido (0.25 mL), triethylamine (0.33 mmol), was refluxed for 30 min, treated with benzylalchol (1.5 mL) The reaction mixture was refluxed for 5 hr. The combined organic layers were concentrated in vacuo. The residue was purified by flash column chromatography on silica gel using EtOAc:hexanes to afford Benzyl N-{1-[3-methoxy-4-(methylsulfonylamino)phenyl]ethyl}carbamate (14-1, CHK-567).

72% yield, yellow oil $^1$H NMR (CDCl$_3$) δ 7.47 (d, 1H, J=8.3), 7.34 (bs, 5H), 6.90 (bd, 1H, J=8.3), 6.85 (bs, 1H), 6.73 (bs, 1H), 5.08 (dd of AB, 2H), 5.02 (bs, 1H), 4.81 (m, 1H), 3.86 (s, 3H), 2.94 (s, 3H), 1.47 (d, 3H, J=6.8 Hz)

Step 100-2. Preparation of 1-[3-Methoxy-4-(methylsulfonylamino)phenyl]ethyl amine (14-3, CHK-570)

Through similar procedure to that in Example 1-2 excepting using Benzyl N-{1-[3-methoxy-4-(methylsulfonylamino)phenyl]ethyl}carbamate (14-1) as a starting material, 1-[3-Methoxy-4-(methylsulfonylamino)phenyl]ethyl amine (14-3, CHK-570) having following physicochemical properties was synthesized:

97% yield, colorless oil $^1$H NMR (CDCl$_3$) δ 7.45 (d, 1H, J=8.3), 6.97 (d, 1H, J=1.7 Hz), 6.90 (dd, 1H, J=1.7, 8.3 Hz), 4.13 (q, 1H, J=6.8 Hz), 3.90 (s, 3H), 2.94 (s, 3H), 1.38 (d, 3H, J=6.8 Hz)

Example 101

Preparation of 1-[3-Chloro-4-(methylsulfonylamino)phenyl]ethyl amine (14-4)

Step 101-1. Preparation of Benzyl N-{1-[3-Chloro-4-(methylsulfonylamino)phenyl]ethyl}carbamate (14-2)

The Benzyl N-{1-[3-Chloro-4-(methylsulfonylamino)phenyl]ethyl}carbamate (14-2) was prepared by the similar procedure with that described in above Example 100-1.

¹H NMR (CDCl₃) δ 7.47 (d, 1H), 7.34 (bs, 5H), 6.90 (bd, 1H), 6.85 (bs, 1H), 6.73 (bs, 1H), 5.08 (dd of AB, 2H), 5.02 (bs, 1H), 4.81 (m, 1H), 3.86 (s, 3H), 2.94 (s, 3H), 1.47 (d, 3H)

Step 101-2. Preparation of 1-[3-Chloro-4-(methylsulfonylamino)phenyl]ethyl amine (14-4)

Through similar procedure to that in Example 1-2 excepting using Benzyl N-{1-[3-Chloro-4-(methylsulfonylamino) phenyl]ethyl}carbamate (14-2) as a starting material 1-[3-Chloro-4-(methylsulfonylamino)phenyl]ethyl amine (14-4) having following physicochemical properties was synthesized:

¹H NMR (CDCl₃) δ 7.53 (d, 1H), 7.00 (d, 1H), 6.92 (dd, 1H), 4.15 (q, 1H), 2.96 (s, 3H), 1.40 (d, 3H)

Example 102

Preparation of N-(4-t-Butylbenzyl)-N'-{1-[4-(methylsulfonylamino)phenyl]ethyl}thiourea (15-1, LJO-328)

A mixture of 1-[4-(Methylsulfonylamino)phenyl]ethyl amine (13-11, 1 mmol) and isothiocyanate (1 mmol) in DMF (2 mL) was stirred at room temperature for 2 h. The reaction mixture was diluted with H₂O and extracted with EtOAc several times. The combined organic layers were washed with H₂O and brine, dried over MgSO₄, filtered, and the filtrate was concentrated in vacuo. The residue was purified by flash column chromatography on silica gel with EtOAc:hexanes (1:1) as eluant to N-(4-t-Butylbenzyl)-N'-{1-[4-(methylsulfonylamino)phenyl]ethyl}thiourea (15-1, LJO-328)

93% yield, white solid, mp=175° C.
¹H NMR (CDCl₃) δ 7.50 (t, 1H, J=8.04 Hz), 7.36 (d, 2H), 7.14 (d, 2H), 7.0-7.05 (m, 2H), 6.48 (s, 1H), 5.95 (bs, 2H), 5.17 (bs, 1H), 4.56 (d, 2H, J=5.1 Hz), 3.02 (s, 3H), 1.46 (d, 3H, J=6.8 Hz), 1.31 (s, 9H)
MS (FAB) m/z 438 (MH⁺)

Example 103

Preparation of N-(4-t-Butylbenzyl)-N'-{1-[3-fluoro-4-(methylsulfonylamino)phenyl]ethyl}thiourea (15-2, CHK-992)

Through similar procedure to that in Example 102 excepting using Methyl 2-amino-5-iodobenzoate (13-2) as a starting material, N-(4-t-Butylbenzyl)-N'-{1-[3-fluoro-4-(methylsulfonylamino)phenyl]ethyl}thiourea (15-2, CHK-992) having following physicochemical properties was synthesized:

92% yield, white solid, mp=165° C.
¹H NMR (CDCl₃) δ 7.59 (d, 1H), 7.36 (d, 2H), 7.32 (d, 1H), 7.1-7.18 (m, 3H), 6.75 (s, 1H), 5.93 (bs, 1H), 5.16 (bs, 1H), 4.57 (bs, 1H), 3.00 (s, 3H), 1.46 (d, 3H), 1.31 (s, 9H)
MS (FAB) m/z 455 (MH⁺)

Example 104

Preparation of N-(4-t-Butylbenzyl)-N'-{1-[3-methoxy-4-(methylsulfonylamino)phenyl]ethyl}thiourea (15-3, CHK-575)

Through similar procedure to that in Example 67 excepting using 1-[3-Methoxy-4-(methylsulfonylamino)phenyl]ethyl amine (14-3) as a starting material, N-(4-t-Butylbenzyl)-N'-{1-[3-methoxy-4-(methylsulfonylamino)phenyl] ethyl}thiourea (15-3, CHK-575) having following physicochemical properties was synthesized:

91% yield, white solid, mp=80-82° C.
¹H NMR (CDCl₃) δ 7.46 (d, 1H, J=8.04 Hz), 7.31 (d, 2H), 7.03 (d, 2H), 6.75-6.85 (m, 3H), 6.14 (bs, 2H), 5.80 (bs, 2H), 4.93 (bs, 1H), 4.58 (ddd of AB, 2H), 3.83 (s, 3H), 2.94 (s, 3H), 1.49 (d, 3H, J=6.6 Hz), 1.30 (s, 9H)
MS (FAB) m/z 450 (MH⁺)

Example 105

Preparation of N-(4-t-Butylbenzyl)-N'-{1-[3-(methoxycarbonyl)-4-(methylsulfonylamino)phenyl]ethyl}thiourea (15-4, YHS-187)

Through similar procedure to that in Example 102 excepting using N-(2-Fluoro-4-iodophenyl)methanesulfonamide (13-3) as a starting material, N-(4-t-Butylbenzyl)-N'-{1-[3-(methoxycarbonyl)-4-(methylsulfonylamino)phenyl]ethyl}thiourea (15-4, YHS-187) having following physicochemical properties was synthesized:

70% yield, white solid, mp=132-135° C.
¹H NMR (CDCl₃) δ 7.99 (d, 1H, J=2.2 Hz), 7.31 (d, 1H, J=8.6 Hz), 7.41 (dd, 1H, J=8.6, 2.2 Hz), 7.33 (d, 2H), 7.11 (d, 2H), 6.04 (bs, 1H), 5.90 (bs, 1H), 5.15 (bs, 1H), 4.58 (s, 2H), 3.94 (s, 3H), 3.05 (s, 3H), 1.48 (d, 3H, J=6.8 Hz), 1.30 (s, 9H)
MS (FAB) m/z 478 (MH⁺)

Example 106

Preparation of N-(4-t-Butylbenzyl)-N'-{1-[3-carboxy-4-(methylsulfonylamino)phenyl]ethyl}thiourea (15-5, YHS-209)

Through similar procedure to that in Example 1-4 excepting using N-(4-t-Butylbenzyl)-N'-{1-[3-(methoxycarbonyl)-4-(methylsulfonylamino)phenyl]ethyl}thiourea (15-4) as a starting material, N-(4-t-Butylbenzyl)-N'-{1-[3-carboxy-4-(methylsulfonylamino)phenyl]ethyl}thiourea (15-5, YHS-209) having following physicochemical properties was synthesized:

72% yield, white solid, mp=189-192° C.
¹H NMR (CD₃OD) δ 8.00 (d, 1H, J=2.2 Hz), 7.49 (d, 1H, J=8.6 Hz), 7.35 (dd, 1H, J=8.6, 2.2 Hz), 7.22 (d, 2H), 7.04 (d, 2H), 6.78 (bs, 1H), 5.34 (bs, 1H), 4.64 (d, 1H, J=14 Hz), 4.47 (d, 1H, J=15 Hz), 2.88 (s, 3H), 1.38 (d, 3H, J=7 Hz), 1.19 (s, 9H)
MS (FAB) m/z 464 (MH⁺)

Example 107

Preparation of N-(4-t-Butylbenzyl)-N'-{(1R)-1-[4-(methylsulfonylamino)phenyl]ethyl}thiourea (16-5, SU-388)

Step 107-1. Preparation of N-(4-t-Butylbenzyl)-N-[(1R)-1-(4-nitrophenyl)ethyl]thiourea (16-1, SU-354)

To a stirred solution of (R or S)-α-methyl-4-nitrobenzyl amine hydrochloride (203 mg, 1 mmol) in anhydrous CH₂Cl₂ (10 mL) was added triethylamine (0.28 mL, 2 mmol) at room temperature. When the reaction mixture became clear, isothiocyanate (1 mmol) was added and stirred overnignt at room temperature. The mixture was evaporated by rotary evaporator and the residue was purified by flash column chromatography on silica gel with EtOAc:hexanes as eluant to N-(4-t-Butylbenzyl)-NA-{(1R)-1-[4-(methylsulfonylamino) phenyl]ethyl}thiourea (16-5, SU-388).

98% yield, a sticky colorless oil $^1$H NMR (CDCl$_3$) δ 8.12 (d, 2H, J=8.76 Hz), 7.34 (bd, 4H), 7.14 (d, 2H, J=8.0 Hz), 6.21 (bs, 2H), 5.37 (bs, 1H), 4.54 (m, 2H), 1.47 (d, 3H, J=7.05 Hz), 1.30 (s, 9H)

Step 107-2. Preparation of N-(4-t-Butylbenzyl)-N'-[(1R)-1-(4-aminophenyl)ethyl]thiourea (16-3, SU-358)

Aluminium foil (0.05 mm thick, 406 mg, 15 mmol) was roughed with sand paper, cut into 0.5 cm squares, and weighed in the reaction flask, The aluminium was etched with 5% KOH hydroxide solution until vigorous evolution of H$_2$ occurred and then the basic solution was removed by decantation. The Al was rinsed with H$_2$ and covered with 0.5% HgCl$_2$ solution for 2 min. The HgCl$_2$ solution was poured off and the Al was washed with H$_2$O. HgCl$_2$ solution was reintroduced for 2 min and the solution was decanted away. Al was washed with H$_2$O followed by ethanol and diethyl ether several times. A solution of nitro (0.5 mmol) in diethyl ether (5 mL) was added to the freshly prepared amalgam and then a drop of H$_2$O was introduced and the mixture was refluxed for 10 minutes. After the reaction was completed by TLC, the mixture was concentrated in vacuo. The residue was purified by flash column chromatography on silica gel with EtOAc: hexanes as eluant to N-(4-t-Butylbenzyl)-N'-[(1R)-1-(4-aminophenyl)ethyl]thiourea (16-3, SU-358).

67% yield, a faint yellow oil $^1$H NMR (CDCl$_3$) 7.29 (d, 2H, J=8.3 Hz), 7.04 (d, 2H, J=8.3 Hz), 6.99 (d, 2H, J=8.04 Hz), 6.63 (d, 2H, J=8.3 Hz), 6.16 (bs, 1H), 5.73 (bs, 1H), 4.69 (bs, 1H), 4.60 (d, 2H, J=4.86 Hz), 3.69 (bs, 2H), 1.45 (d, 3H, J=6.84 Hz), 1.30 (s, 9H)

Step 107-3. Preparation of N-(4-t-Butylbenzyl)-N'-{(1R)-1-[4-(methylsulfonylamino)phenyl]ethyl}thiourea (16-5. SU-388)

A cooled solution of N-(4-t-Butylbenzyl)-N'-[(1R)-1-(4-aminophenyl)ethyl]thiourea (16-3, 0.25 mmol) in pyridine (2 mL) at 0° C. was treated with methanesulfonyl chloride (0.3 mmol) and stirred for 10 min at 0° C. After aqueous work-up, the residue was purified by flash column chromatography on silica gel with EtOAc:hexanes as eluant 75% yield, white solid, mp=101° C.

The spectral data of compound 16-5 were identical to those of compound 15-1.

[α]=−13.34 (CHCl$_3$, C=1.075)

Example 108

Preparation of N-(4-t-Butylbenzyl)-N'-{(1S)-1-[4-(methylsulfonylamino)phenyl]ethyl}thiourea (16-6, SU-400)

Step 108-1. Preparation of N-(4-t-Butylbenzyl)-N'-[(1S)-1-(4-nitrophenyl)ethyl]thiourea (16-2. SU-366)

The N-(4-t-Butylbenzyl)-N'-[(1S)-1-(4-nitrophenyl)ethyl] thiourea (16-2, SU-366) was prepared by the similar procedure with that described in above Example 107-1.

A sticky white oil

The spectral data of compound 16-2 were identical to those of compound 16-1.

Step 108-2. Preparation of N-(4-t-Butylbenzyl)-N—[(S)-1-(4-aminophenyl)ethyl]thiourea (16-4, SU-394)

The N-(4-t-Butylbenzyl)-N'-[(1S)-1-(4-aminophenyl) ethyl]thiourea (16-4, SU-394) was prepared by the similar procedure with that described in above Example 107-1.

A faint yellow oil

The spectral data of compound 16-4 were identical to those of compound 16-3.

Step 108-3. Preparation of N-(4-t-Butylbenzyl)-N'-{(1S)-1-[4-(methylsulfonylamino)phenyl] ethyl}thiourea (16-6, SU-400)

The N-(4-t-Butylbenzyl)-N'-{(1S)-1-[4-(methylsulfonylamino)phenyl]ethyl}thiourea (16-6, SU-400) was prepared by the similar procedure with that described in above Example 107-1.

75% yield, white solid, mp=101° C.

The spectral data of compound 16-6 were identical to those of compound 15-1.

[α]=+10.60 (CHCl$_3$, c=1.075)

Example 109

Preparation of (R)—N-(4-t-Butylbenzyl)-N'-{1-[3-fluoro-4-(methylsulfonylamino)phenyl] ethyl}thiourea (17-3, CJU-032)

Step 109-1. Preparation of (R)-Sulfonamide (17-1)

To a 0.5M solution of Ti(OEt)$_4$ (0.3 mL, 1.44 mmol) and N-(4-acetyl-2-fluorophenyl)-methanesulfonamide (0.2 g, 0.87 mmol) in THF (5 mL) under an N$_2$ atmosphere was added (R)-(+)-2-methyl-2-propanesulfinamide (0.087 g, 0.72 mmol) and the mixture was heated (70° C.). Upon completion, as determined by TLC, the mixture was cooled to room temperature and then to −40° C. before it was cannulated dropwise into a −40° C. solution of NaBH$_4$ (0.109 g. 2.88 mmol). The mixture was stirred at −40° C. for 12 h, and then MeOH was added dropwise until gas was no longer evolved. The resulting suspension was filtered through a plug of Celite and the filter cake was washed with EtOAc. The filtrate was washed with brine, and the brine layer was extracted with EtOAc. The combined organic portions were dried (Na$_2$SO$_4$), filtered, and concentrated. After silica gel column chromatography (n-hexane/EtOAc), The (R)-sulfonamide (0.105 g, 0.31 mmol, 36%) was isolated $^1$H-NMR (CDCl$_3$) δ 7.53 (t, 1H, J=8.4 Hz), 7.19 (m, 1H), 7.15 (m, 1H), 6.97 (bs, 1H), 4.53 (m, 1H), 3.50 (d, 1H, J=3.8 Hz), 3.04 (s, 3H), 1.75 (bs, 1H), 1.51 (d, 3H, J=6.5 Hz), 1.25 (s, 9H).

Step 109-2. Preparation of (R)-1-[3-Fluoro-4-(methylsulfonylamino)phenyl]ethyl amine hydrochloride (17-2)

To a (R)-sulfonamide (0.105 g, 0.31 mmol) was added 1:1 (v/v) MeOH and HCl dioxane solution (4.0 M, 0.22 mL). The mixture was stirred at room temperature for 30 minutes and was then concentrated to near dryness. Diethyl ether was added to precipitate the amine hydrochloride. The precipitate was then filtered off and washed with diethyl ether to provide analytically pure (R)-1-[3-Fluoro-4-(methylsulfonylamino) phenyl]ethyl amine hydrochloride (17-2, 0.059 g, 0.22 mmol, 70%, 96.11 ee %)

$^1$H-NMR (DMSO-$d_6$) δ 9.71 (bs, 1H), 8.60 (bs, 3H), 7.52 (dd, 1H, J=1.9, 11.8 Hz), 7.42 (t, 1H, J=8.4 Hz), 7.33 (dd, 1H, J=1.8, 8.4 Hz), 4.39 (m, 1H), 3.62 (m, 1H), 3.05 (s, 3H), 1.49 (d, 3H, J=6.5 Hz).

Step 109-3. Preparation of N-{4-{1-[3-(4-tert-Butyl-benzyl)-thioreido]-ethyl}-2-fluorophenyl}-methanesulfonamide (17-3. CJU-032)

To a stirred solution of 4-[4-(1-Amino-ethyl)-2-fluoro-phenyl]-methanesulfonamide hydrochloride (0.020 g, 0.075 mmol) in DMF (1 mL), Et$_3$N (13 μL, 0.09 mmol), 1-tertbutyl-4-isothiocyanatomethyl benzene (15 mg, 0.075 mmol) were added in the written order. The reaction mixture was stirred for 3 hours at room temperature. And then the reaction solution was extracted by EtOAc and the organic phase was washed with H$_2$O, dried (Na$_2$SO$_4$), filtered and concentrated. After silica gel column chromatography (n-hexane/EtOAc), N-{4-{1-[3-(4-tert-Butyl-benzyl)-thioreido]-ethyl}-2-fluoro-phenyl}-methanesulfonamide (26 mg, 0.06 mmol, 85%) was isolated

[α]–19.24 (c 0.7, CHCl$_3$), ee % 98.41%

$^1$H-NMR (CDCl$_3$) δ 7.42 (t, 1H, J=9.0 Hz), 7.35 (m, 1H), 7.33 (m, 1H), 7.12 (m, 2H), 7.00 (m, 2H), 6.90 (bs, 1H), 6.45-6.10 (bs, 2H), 5.18 (bs, 1H), 4.54 (m, 2H), 2.98 (s, 3H), 1.43 (d, 3H, J=3.0 Hz), 1.29 (s, 9H).

Example 110

Preparation of (S)—N-(4-t-Butylbenzyl)-N'-{1-[3-fluoro-4-(methylsulfonylamino)phenyl]ethyl}thiourea (17-6, CJU-039)

Step 110-1. Preparation of(S)-Sulfonamide (17-4)

The compound 17-4 was prepared from (S)-(–)-2-methyl-2-propanesulfinamide by following the similar procedure with that described in Example 109-1.

31% yield $^1$H-NMR (CDCl$_3$) δ 7.47 (m, 1H), 7.26 (bs, 1H), 7.17-7.08 (m, 2H), 4.48 (m, 1H), 3.54 (d, 1H, J=3.8 Hz), 2.99 (s, 3H), 1.47 (d, 3H, J=6.5 Hz), 1.21 (s, 9H).

Step 110-2. Preparation of (S)-1-[3-Fluoro-4-(methylsulfonylamino)phenyl]ethyl amine hydrochloride (17-5)

The compound 17-5 was prepared from (S)-Sulfonamide (17-4) by following the similar procedure with that described in Example 109-2.

88% yield, 97.9 ee %

The spectral data is identical to that of 17-2.

Step 110-3. Preparation of (S)—N-(4-t-Butylbenzyl)-N-{1-[3-fluoro-4-(methylsulfonylamino)phenyl]ethyl}thiourea (17-6, CJU-039)

The compound 17-6 was prepared from (S)-1-[3-Fluoro-4-(methylsulfonylamino)phenyl]ethyl amine hydrochloride (17-5) by following the similar procedure with that described in Example 1-5.

80% yield, [α]=16.04 (c 0.7, CHCl$_3$), 97.76 ee %

The spectral data is identical to that of 17-3.

Example 111

Preparation of N-[(2R)-2-Benzyl-3-(pivaloyloxy) propyl]-N'-{(1R)-1-[4-(methylsulfonylamino)phenyl]ethyl}thiourea (18-1, MK-229)

The N-[(2R)-2-Benzyl-3-(pivaloyloxy)propyl]-N'-{(1R)-1-[4-(methylsulfonylamino)phenyl]ethyl}thiourea (18-1) was prepared by the similar procedure with that described in above Example 1-5.

84% yield, white solid, mp=62-64° C.

[δ]=–10.8 (CHCl$_3$, c 1.0)

$^1$H NMR (CDCl$_3$) δ 7.1-7.35 (m, 9H), 6.61 (bs, 1H), 6.26 (bs, 1H), 6.15 (bt, 1H), 4.82 (bs, 1H), 4.10 (dd, 1H, J=11.7, 3.3 Hz), 3.6-3.75 (m, 2H), 3.24 (m, 1H), 2.96 (s, 3H), 2.55 (dd, 1H), 2.54 (dd, 1H), 2.36 (dd, 1H), 2.29 (bs, 1H), 1.49 (d, 3H, J=6.6 Hz), 1.21 (m, 9H)

MS (EI) m/z 505 (M$^+$)

Example 112

Preparation of N-[(2S)-2-Benzyl-3-(pivaloyloxy) propyl]-N'-{(1R)-1-[4-(methylsulfonylamino)phenyl]ethyl}thiourea (18-2, MK-202)

The N-[(2S)-2-Benzyl-3-(pivaloyloxy)propyl]-N'-{(1R)-1-[4-(methylsulfonylamino)phenyl]ethyl}thiourea (18-2) was prepared by the similar procedure with that described in above Example 1-5.

76% yield, white solid, mp=58-62° C.

[δ]=+2.04 (CHCl$_3$, c 1.0)

$^1$H NMR (CDCl$_3$) δ 7.1-7.35 (m, 9H), 6.37 (bs, 1H), 6.11 (bs, 1H), 4.80 (bs, 1H), 3.7-3-9 (m, 2H), 3.58 (m, 1H), 3.12 (m, 1H), 2.94 (s, 3H), 2.54 (ddd, 2H), 2.17 (bs, 1H), 1.47 (d, 3H, J=6.6 Hz), 1.21 (m, 9H)

MS (FAB) m/z 506 (MH$^+$)

Example 113

Preparation of N-[(2R)-2-Benzyl-3-(pivaloyloxy) propyl]-N'-{(1S)-1-[4-(methylsulfonylamino)phenyl]ethyl}thiourea (18-3, MK-230)

The N-[(2R)-2-Benzyl-3-(pivaloyloxy)propyl]-N'-{(1S)-1-[4-(methylsulfonylamino)phenyl]ethyl}thiourea (18-3) was prepared by the similar procedure with that described in above Example 1-5.

81% yield, white solid, mp=58-62° C.

[α]=–2.48 (CHCl$_3$, c 1.0)

The spectral data of compound 18-3 were identical to those of compound 18-2.

Example 114

Preparation of N-[(2S)-2-Benzyl-3-(pivaloyloxy) propyl]-N'-{(1S)-1-[4-(methylsulfonylamino)phenyl]ethyl}thiourea (18-4, MK-228)

The N-[(2S)-2-Benzyl-3-(pivaloyloxy)propyl]-N'-{(1S)-1-[4-(methylsulfonylamino)phenyl]ethyl}thiourea (18-4) was prepared by the similar procedure with that described in above Example 1-5.

88% yield, white solid, mp=62-64° C.
[α]=+11.61 (CHCl₃, c 1.0)
The spectral data of compound 18-3 were identical to those of compound 18-1.
MS (FAB) m/z 506 (MH⁺)

Example 115

Preparation of N-[2-(3,4-Dimethylbenzyl)-3-(pivaloyloxy)propyl]-N'-{1-[4-(methylsulfonylamino)phenyl]ethyl}thiourea (18-5, LJO-388)

The N-[2-(3,4-Dimethylbenzyl)-3-(pivaloyloxy)propyl]-N-({1-[4-(methylsulfonylamino)phenyl]ethyl}thiourea (18-5) was prepared by the similar procedure with that described in above Example 1-5.
87% yield, white solid, mp=77° C.
¹H NMR (CDCl₃) δ 7.15-7.35 (m, 4H), 6.8-7.05 (m, 4H), 6.36 (bs, 1H), 6.18 (bs, 1H), 4.79 (bs, 1H), 3.55-3.75 (bs, 3H), 3.12 (m, 1H), 2.95-3.0 (s, 3H), 2.4-2.6 (m, 2H), 2.1-2.3 (m, 7H), 1.4-1.5 (m, 3H), 1.20 (m, 9H)
MS (FAB) m/z 534 (MH⁺)

Example 116

Preparation of N-[2-(3,4-Dimethylbenzyl)-3-(pivaloyloxy)propyl]-N'-{(1R)-1-[4-(methylsulfonylamino)phenyl]ethyl}thiourea (18-6, SU-472)

The N-[2-(3,4-Dimethylbenzyl)-3-(pivaloyloxy)propyl]-N'-{(1R)-1-[4-(methylsulfonylamino)phenyl]ethyl}thiourea (18-6) was prepared by the similar procedure with that described in above Example 1-5.
white solid,
The spectral data of compound 18-6 were identical to those of compound 18-5.

Example 117

Preparation of N-[(2R)-2-(3,4-Dimethylbenzyl)-3-(pivaloyloxy)propyl]-N'-{(1R)-1-[4-(methylsulfonylamino)phenyl]ethyl}thiourea (18-7, SU-512)

The N-[(2R)-2-(3,4-Dimethylbenzyl)-3-(pivaloyloxy)propyl]-N'-{(1R)-1-[4-(methylsulfonylamino)phenyl]ethyl}thiourea (18-7) was prepared by the similar procedure with that described in above Example 1-5.
¹H NMR (CDCl₃) δ 7.34 (bd, 2H), 7.19 (bd, 2H), 6.7-7.05 (m, 3H), 6.29 (bs, 1H), 6.15 (bs, 1H), 4.81 (bs, 1H), 4.12 (m, 1H), 3.5-3.75 (m, 2H), 3.18 (m, 1H), 2.96 (s, 3H), 2.4-2.6 (m, 2H), 2.1-2.3 (m, 7H), 1.4-1.5 (d, 3H), 1.21 (m, 9H)

Example 118

Preparation of N-[(2S)-2-(3,4-Dimethylbenzyl)-3-(pivaloyloxy)propyl]-N'-{(1R)-1-[4-(methylsulfonylamino)phenyl]ethyl}thiourea (18-8)

The N-[(2S)-2-(3,4-Dimethylbenzyl)-3-(pivaloyloxy)propyl]-N'-{(1R)-1-[4-(methylsulfonylamino)phenyl]ethyl}thiourea (18-8) was prepared by the similar procedure with that described in above Example 1-5.
¹H NMR (CDCl₃) δ 7.33 (bd, 2H), 7.18 (bd, 2H), 6.72-7.05 (m, 3H), 6.28 (bs, 1H), 6.12 (bs, 1H), 4.80 (bs, 1H), 4.11 (m, 1H), 3.5-3.75 (m, 2H), 3.19 (m, 1H), 2.98 (s, 3H), 2.4-2.6 (m, 2H), 2.1-2.3 (m, 7H), 1.4-1.5 (d, 3H), 1.22 (m, 9H)
MS (FAB) m/z 534 (MH⁺)

Example 119

Preparation of N-[2-(4-tert-Butylbenzyl)-3-(pivaloyloxy)propyl]-N'-{1-[4-(methylsulfonylamino)phenyl]ethyl}thiourea (18-9, LJO-401)

The N-[2-(4-tert-Butylbenzyl)-3-(pivaloyloxy)propyl]-N'-{1-[4-(methylsulfonylamino)phenyl]ethyl}thiourea (18-9) was prepared by the similar procedure with that described in above Example 1-5.
84% yield, white solid, mp=87° C.
¹H NMR (CDCl₃) δ 7.0-7.35 (m, 8H), 6.43 (bs, 1H), 6.19 (bs, 1H), 4.83 (bs, 1H), 3.55-3.75 (bs, 3H), 3.1-3.3 (m, 1H), 2.93 (s, 3H), 2.4-2.6 (m, 2H), 2.25 (m, 1H), 1.4-1.5 (m, 3H), 1.28 (s, 9H), 1.20 (s, 9H)
MS (FAB) m/z 562 (MH⁺)

Example 120

Preparation of N-[2-(4-tert-Butylbenzyl)-3-(pivaloyloxy)propyl]-N'-{(1R)-1-[4-(methylsulfonylamino)phenyl]ethyl}thiourea (18-10, MK-296)

The N-[2-(4-tert-Butylbenzyl)-3-(pivaloyloxy)propyl]-N'-{(1R)-1-[4-(methylsulfonylamino)phenyl]ethyl}thiourea (18-10) was prepared by the similar procedure with that described in above Example 1-5.
88% yield, white solid, mp=88-90° C.
¹H NMR (CDCl₃) δ 7.25-7.35 (m, 4H), 7.15-7.23 (m, 2H), 7.0-7.1 (m, 2H), 6.36 (bs, 1H), 6.15 (bs, 1H), 4.84 (bs, 1H), 3.5-3.9 (m, 3H), 3.1-3.3 (m, 1H), 2.94 (s, 3H), 2.3-2.55 (m, 2H), 2.15 (m, 1H), 1.48 (m, 3H, J=6.8 Hz), 1.29 (s, 9H), 1.21 (s, 9H)
MS (FAB) m/z 562 (MH⁺)

Example 121

Preparation of N-[(2R)-2-(4-tert-Butylbenzyl)-3-(pivaloyloxy)propyl]-N'-{(1R)-1-[4-(methylsulfonylamino)phenyl]ethyl}thiourea (18-11, MK-334)

The N-[(2R)-2-(4-tert-Butylbenzyl)-3-(pivaloyloxy)propyl]-N'-{(1R)-1-[4-(methylsulfonylamino)phenyl]ethyl}thiourea (18-11) was prepared by the similar procedure with that described in above Example 1-5.
88% yield, white solid, mp=85-87° C.
[α]−17.3 (c 1.00, CHCl₃)
¹H NMR (CDCl₃) δ 7.28-7.36 (dd, 4H), 7.19 (d, 2H), 7.03 (d, 2H), 6.80 (bs, 1H), 6.34 (bs, 1H), 6.15 (bt, 1H), 4.84 (bs, 1H), 4.08 (dd, 1H, J=3.8, 11.7 Hz), 3.55-3.7 (m, 2H), 3.24 (ddd, 1H), 2.95 (s, 3H), 2.50 (dd, 1H), 2.34 (dd, 1H), 2.26 (m, 1H), 1.48 (d, 3H, J=6.8 Hz), 1.29 (s, 9H), 1.21 (s, 9H)
MS (FAB) m/z 562 (MH⁺)

Example 122

Preparation of N-[(2S)-2-(4-tert-Butylbenzyl)-3-(pivaloyloxy)propyl]-N'-{(1R)-1-[4-(methylsulfonylamino)phenyl]ethyl}thiourea (18-12, MK-298)

The N-[(2S)-2-(4-tert-Butylbenzyl)-3-(pivaloyloxy)propyl]-N'-{(1R)-1-[4-(methylsulfonylamino)phenyl]ethyl}thiourea (18-12) was prepared by the similar procedure with that described in above Example 1-5.
86% yield, white solid, mp=88-90° C.
[α]=−3.77 (c 1.00, CHCl₃)

¹H NMR (CDCl₃) δ 7.25-7.35 (dd, 4H), 7.18 (d, 2H), 7.05 (d, 2H), 6.47 (bs, 1H), 6.15 (bs, 1H), 4.84 (bs, 1H), 3.55-3.9 (m, 3H), 3.14 (ddd, 1H), 2.94 (s, 3H), 2.52 (dd of AB, 2H), 2.16 (m, 1H), 1.47 (d, 3H, J=6.8 Hz), 1.29 (s, 9H), 1.21 (s, 9H)
MS (FAB) m/z 562 (MH⁺)

Example 123

Preparation of N-[2-(3,4-Dimethylbenzyl)-3-(pivaloyloxy)propyl]-N'-{1-[3-fluoro-4-(methylsulfonylamino)phenyl]ethyl}thiourea (18-13, LJO-344)

The N-[2-(3,4-Dimethylbenzyl)-3-(pivaloyloxy)propyl]-N'-{1-[3-fluoro-4-(methylsulfonylamino)phenyl]ethyl}thiourea (18-13) was prepared by the similar procedure with that described in above Example 1-5.
76% yield, white solid, mp=73° C.
¹H NMR (CDCl₃) δ 7.50 (m, 1H), 6.8-7.2 (m, 5H), 6.75 (bs, 1H), 6.30 (bs, 1HH), 6.22 (bs, 1H), 4.89 (bs, 1H), 4.16 (m, 1H), 3.6-3.9 (m, 2H), 3.10 (m, 1H), 3.0 (m, 3H), 2.45-2.65 (m, 2H), 2.15-2.3 (m, 7H), 1.4-1.5 (m, 3H), 1.22 (m, 9H)
MS (FAB) m/z 552 (MH⁺)

Example 124

Preparation of N-[2-(4-tert-Butylbenzyl)-3-(pivaloyloxy)propyl]-N'-{1-[3-fluoro-4-(methylsulfonylamino)phenyl]ethyl}thiourea (18-14, LJO-366)

The N-[2-(4-tert-Butylbenzyl)-3-(pivaloyloxy)propyl]-N'-{1-[3-fluoro-4-(methylsulfonylamino)phenyl]ethyl}thiourea (18-14) was prepared by the similar procedure with that described in above Example 1-5.
73% yield, white solid, mp=78° C.
¹H NMR (CDCl₃) δ 7.53 (m, 1H), 7.0-7.35 (m, 6H), 6.53 (bs, 1H), 6.24 (bt, 1H), 6.17 (bs, 1H), 4.92 (bs, 1H), 4.15 (m, 1H), 3.6-3.9 (m, 2H), 3.10 (m, 1H), 3.0 (m, 3H), 2.4-2.6 (m, 2H), 2.24 (m, 1H), 1.4-1.5 (m, 3H), 1.29 (m, 9H), 1.22 (m, 9H)
MS (FAB) m/z 580 (MH⁺)

Example 125

Preparation of N-[(2R)-3-phenyl-1-pivaloyloxy-2-propyl]-N'-[(R)-α-methyl-4-(methylsulfonylamino)benzy]thiourea (19-13, SU-692)

Step 125-1. Preparation of (2R)-3-phenyl-1-pivaloyloxy-2-propyl amine (19-1, YHS-43)

A solution of (2R)—N-(tert-butoxycarbonyl)phenylalaniol (3.323 g) on the market in methylene chloride (50 mL) was added triethylamine (7.4 mL) and pivaloy chloride (2.4 mL). The mixture was stirred for 4 hr at room temperate. 50° C. and then for 10 min. at room temperature. The mixture was directly purified by column chromatography using EtOAc: hexanes (1:4) as eluant to afford ester compound. And then the reaction compound was diluted with methylene chloride (10 mL) was stirred trifluoroacetic acid (2.5 mL). The mixture was stirred at room temperature for 2 hours and was concentrated in vacuo to afford (2R)-3-phenyl-1-pivaloyloxy-2-propyl amine (19-1, YHS-43).
¹H NMR (CDCl₃) δ 7.15-7.38 (m, 5H), 4.22 (dd of AB, 2H), 3.73 (bs, 1H), 3.03 (ddd of AB, 2H), 1.22 (s, 9H)

Step 125-2. Preparation of (2R)-3-phenol-1-pivaloyloxy-2-propyl isothiocyanate (19-3, SU-684)

A solution of (2R)-3-phenyl-1-pivaloyloxy-2-propyl amine (19-1, 1 mmol) and Et₃N (1 mmol) in DMF (1 mL) was added dropwise into the pre-dissolved solution of 1,1-thiocarbonyl diimidazole (1.2 mmol) in DMF (2 mL) at 50° C. over 1 min. The mixture was stirred for 1 min. at 50° C. and then for 10 min. at room temperature. The mixture was directly purified by column chromatography using EtOAc: hexanes (1:5) as eluant to afford (2R)-3-phenyl-1-pivaloyloxy-2-propyl isothiocyanate (19-3, SU-684).
89% yield, colorless oil.
¹H NMR (CDCl₃) δ 7.15-7.35 (m, 5H), 4.22 (dd, 1H, J=2.7, 10 Hz), 4.02-4.12 (m, 2H), 2.94 (d, 2H, J=6.3 Hz), 1.25 (s, 9H)

Step 125-3. Preparation of N-[(2R)-3-phenyl-1-pivaloyloxy-2-propyl]-N'-[(R)-α-methyl-4-nitrobenzy]thiourea (19-5, SU-688)

To a stirred solution of (R or S)-α-methyl-4-nitrobenzyl amine hydrochloride (1.1 mmol) in CH₂Cl₂ (8 mL) was added Et₃N (1.1 mmol) at room temperature. The mixture was stirred for 10 minutes. When the reaction mixture became clear, isothiocyanate (1 mmol) in CH₂Cl₂ (2 mL) was added. The mixture was stirred overnight at room temperature and concentrated in vacuo. The residue was purified by flash column chromatography on silica gel with EtOAc:hexanes (1:2 to 1:1).
81% yield, yellow oil
¹H NMR (CDCl₃) δ 8.15 (d, 2H, J=8.5 Hz), 7.45 (d, 2H, J=8.5 Hz), 7.15-7.35 (m, 5H), 6.60 (bs, 1H), 6.08 (bs, 1H), 5.22 (bs, 1H), 4.47 (bs, 1H), 4.13 (dd, 1H, J=3, 11.8 Hz), 3.86 (dd, 2H, J=5.6, 11.8 Hz), 2.96 (dd, 1H, J=5.85, 13.5 Hz), 2.80 (dd, 1H, J=7.3, 13.5 Hz), 1.49 (d, 3H, J=7.1 Hz), 1.16 (s, 9H)

Step 125-4. Preparation of N-[(2R)-3-phenyl-1-pivaloyloxy-2-propyl]-N'-[(R)-α-methyl-4-aminobenzy]thiourea (19-9, SU-690)

Aluminium foil (0.05 mm thick, 328 mg, 12.174 mmol) was roughed with sand bar, cut into 0.5 cm squares and was etched with 5% KOH hydroxide solution until vigorous evolution of H₂ occurred. The basic solution was removed by decantation and the Al was rinsed with H₂O two times and was covered with 0.5% HgCl₂ solution for 2 minutes. The mercuric chloride was poured off, the Al was washed with H₂O two times and HgCl₂ solution was reintroduced for 2 minutes. Once again the HgCl₂ solution was decanted away, Al was washed with H₂O several times followed by ethanol and diethyl ether several times. A solution of N-[(2R)-3-phenyl-1-pivaloyloxy-2-propyl]-N'-[(R)-☐-methyl-4-nitrobenzy]thiourea (19-5, 180 mg, 0.406 mmol) in diethyl ether 10 mL was added to the freshly prepared amalgam then H₂O (3 drops) was introduced and the mixture was refluxed for 30 minutes. After the reaction was completed by TLC, the mixture was cooled down to room temperature and filtered through glass funnel spreaded with MgSO₄ (0.7 cm) above celite 545 (0.7 cm). The filtrate was evaporated by rotary evaporator to be dried by vacuum pump.
96% yield, colorless oil
¹H NMR (CDCl₃) δ 7.15-7.35 (m, 5H), 7.00 (d, 2H, J=8.3 Hz), 6.63 (d, 2H, J=8.3 Hz), 6.30 (bs, 1H), 5.70 (bs, 1H), 4.75 (bs, 1H), 4.52 (bs, 1H), 3.96 (dd, 1H, J=3, 11.2 Hz), 3.79 (dd, 2H, J=4.6, 11.2 Hz), 2.97 (dd, 1H, J=5.85, 13.9 Hz), 2.77 (dd, 1H, J=8, 13.9 Hz), 1.41 (d, 3H, J=7.1 Hz), 1.16 (s, 9H)

Step 125-5. Preparation of N-[(2R)-3-phenyl-1-pivaloyloxy-2-propyl]-N'-[(R)-α-methyl-4-(methylsulfonylamino)benzy]thiourea (19-13, SU-692)

A cooled solution of N-[(2R)-3-phenyl-1-pivaloyloxy-2-propyl]-N'-[(R)-α-methyl-4-aminobenzy]thiourea (19-9, 0.5 mmol) in pyridine (2 mL) at 0° C. was treated dropwise with methanesulfonyl chloride (0.75 mmol) and was stirred for 10 minutes at 0° C. The mixture was directly purified by flash column chromatography on silica gel with EtOAc:hexanes (1:1) as eluant to N-[(2R)-3-phenyl-1-pivaloyloxy-2-propyl]-N'-[(R)-α-methyl-4-(methylsulfonylamino)benzy]thiourea (19-13, SU-692).

92% yield, pale yellow solid, mp=59-61° C., [α]=+18.1 (c 1.00, CHCl₃)

¹H NMR (CDCl₃) δ 7.1-7.35 (m, 9H), 6.62 (bs, 1H), 5.88 (bs, 1H), 4.84 (bs, 1H), 4.65 (bs, 1H), 4.00 (bd, 1H), 3.76 (dd, 2H, J=4.6, 11.2 Hz), 2.9-3.05 (m, 4H), 2.80 (dd, 1H, J=7.1, 13.4 Hz), 1.46 (d, 3H, J=7.1 Hz), 1.18 (s, 9H)

MS(FAB) m/z 492 (MH⁺)

Example 126

Preparation of N-[(2S)-3-phenyl-1-pivaloyloxy-2-propyl]-N'-[(R)-α-methyl-4-(methylsulfonylamino)benzy]thiourea (19-14, SU-704)

Step 126-1. Preparation of N-[(2S-3-phenyl-1-pivaloyloxy-2-propyl]-N'-[(R)-α-methyl-4-nitrobenzy]thiourea (19-6, SU-698)

The N-[(2S)-3-phenyl-1-pivaloyloxy-2-propyl]-N'-[(R)-α-methyl-4-nitrobenzy]thiourea (19-6) was prepared by the similar procedure with that described in above Example 125-1, 125-2 and 125-3.

94% yield, pale yellow solid, mp=99-100° C.

The spectral data of this compound were identical to those of compound 19-5.

Step 126-2. Preparation of N-[(2S)-3-phenyl-1 pivaloyloxy-2-propyl]-N'-[(R)-α-methyl-4-aminobenzy]thiourea (19-10. SU-702)

Through similar procedure to that in Example 125-4 excepting using N-[(2S)-3-phenyl-1-pivaloyloxy-2-propyl]-N'-[(R)-α-methyl-4-nitrobenzy]thiourea (19-6) as a starting material, N-[(2S)-3-phenyl-1-pivaloyloxy-2-propyl]-N'-[(R)-α-methyl-4-aminobenzy]thiourea (19-10, SU-702) having following physicochemical properties was synthesized:

97% yield, yellow oil

The spectral data of this compound were identical to those of compound 19-9.

Step 126-3. Preparation of N-[(2S)-3-phenyl-1-pivaloyloxy-2-propyl]-N'-[(R)-α-methyl-4-(methylsulfonylamino)benzy]thiourea (19-14, SU-704)

Through similar procedure to that in Example 125-5 excepting using 3'-(Methoxycarbony)-4'-(methylsulfonylamino)acetophenone oxime (13-10) as a starting material, N-[(2S)-3-phenyl-1-pivaloyloxy-2-propyl]-N'-[(R)-α-methyl-4-(methylsulfonylamino)benzy]thiourea (19-14, SU-704) having following physicochemical properties was synthesized:

51% yield, yellow solid, mp=61-64° C., [α]=−10.9 (c 1.00, CHCl₃)

The spectral data of this compound were identical to those of compound 19-13.

MS (FAB) m/z 492 (MH⁺)

Example 127

Preparation of N-[(2R)-3-phenyl-1-pivaloyloxy-2-propyl]-N'-[(S)-α-methyl-4-(methylsulfonylamino)benzy]thiourea (19-15, SU-720)

Step 127-1. Preparation of (2S)-3-phenyl-1-pivaloyloxy-2-propyl amine (19-2, YHS-45)

The (2S)-3-phenyl-1-pivaloyloxy-2-propyl amine (19-2, YHS-45) was prepared by the similar procedure with that described in above Example 125-1.

94% yield, pale yellow oil

¹H NMR (CDCl₃) δ 7.15-7.38 (m, 5H), 4.22 (dd of AB, 2H), 3.73 (bs, 1H), 3.03 (ddd of AB, 2H), 1.22 (s, 9H)

Step 127-2. Preparation of (2S)-3-phenyl-1-pivaloyloxy-2-propyl isothiocyanate (19-4, SU-686)

Through similar procedure to that in Example 92-2 excepting using (28)-3-phenyl-1-pivaloyloxy-2-propyl amine (19-2) as a starting material, (2S)-3-phenyl-1-pivaloyloxy-2-propyl isothiocyanate (19-4, SU-686) having following physicochemical properties was synthesized:

89% yield, colorless oil

The spectral data of compound 19-4 were identical to that of 19-3.

Step 127-3. Preparation of N-[(2R)-3-phenyl-1-pivaloyloxy-2-propyl]-N'-[(S)-α-methyl-4-nitrobenzy]thiourea (19-7, SU-714)

Through similar procedure to that in Example 125-3 excepting using (2S)-3-phenyl-1-pivaloyloxy-2-propyl amine (19-2) as a starting material, N-[(2R)-3-phenyl-1-pivaloyloxy-2-propyl]-N'-[(S)-α-methyl-4-nitrobenzy]thiourea (19-7, SU-714) having following physicochemical properties was synthesized:

78% yield, white solid, mp=100-101° C.

¹H NMR (CDCl₃) δ 8.18 (d, 2H, J=8.5 Hz), 7.46 (d, 2H, J=8.5 Hz), 7.05-7.3 (m, 5H), 6.64 (bs, 1H), 6.12 (bs, 1H), 5.12 (bs, 1H), 4.62 (bs, 1H), 4.19 (dd, 1H, J=4.9, 11.6 Hz), 4.00 (dd, 2H, J=4.1, 11.6 Hz), 2.94 (dd, 1H, J=5.34, 13.4 Hz), 2.64 (bs, 1H), 1.55 (d, 3H, J=7.1 Hz), 1.19 (s, 9H)

Step 127-4. Preparation of N-[(2R)-3-phenyl-1 pivaloyloxy-2-propyl]-N'-[(S)-α-methyl-4-aminobenzy]thiourea (19-11, SU-716)

Through similar procedure to that in Example 92-4 excepting using N-[(2R)-3-phenyl-1-pivaloyloxy-2-propyl]-N—[(S)-α-methyl-4-nitrobenzy]thiourea (19-7) as a starting material, N-[(2R)-3-phenyl-1-pivaloyloxy-2-propyl]-N'-[(S)-α-methyl-4-aminobenzy]thiourea (19-11, SU-716) having following physicochemical properties was synthesized:

86% yield, pale yellow oil

¹H NMR (CDCl₃) δ 6.95-7.25 (m, 7H), 6.67 (d, 2H, J=8.3 Hz), 6.42 (d, 1H, J=5.1 Hz), 5.80 (d, 1H, J=8.3 Hz), 4.83 (bs, 1H), 4.53 (bs, 1H), 4.07 (dd, 1H, J=5.1, 11.7 Hz), 3.94 (dd, 2H, J=3.9, 11.7 Hz), 3.60 (bs, 2H), 2.84 (dd, 1H, J=5.4, 13.7 Hz), 2.49 (dd, 1H, J=8.3, 13.7 Hz), 1.44 (d, 3H, J=7.1 Hz), 1.20 (s, 9H)

Step 127-5. Preparation of N-[(2R)-3-phenyl-1-pivaloyloxy-2-propyl]-N'-[(S)-α-methyl-4-(methylsulfonylamino)benzyl]thiourea (19-15, SU-720)

Through similar procedure to that in Example 125-5 excepting using N-[(2R)-3-phenyl-1-pivaloyloxy-2-propyl]-N'-[(S)-α-methyl-4-aminobenzyl]thiourea (19-11) as a starting material, N-[(2R)-3-phenyl-1-pivaloyloxy-2-propyl]-N'-[(S)-α-methyl-4-(methylsulfonylamino)benzyl]thiourea (19-15, SU-720) having following physicochemical properties was synthesized:

93% yield, pale yellow solid, mp=61-64° C., [α]=+11.5 (c 1.00, $CHCl_3$)

$^1$H NMR ($CDCl_3$) δ 7.45 (bs, 1H), 7.15-7.3 (m, 7H), 7.05 (d, 2H, J=6.3 Hz), 6.78 (bs, 1H), 6.02 (bs, 1H), 4.76 (bs, 2H), 4.14 (dd, 1H, J=5.1, 11.7 Hz), 3.97 (dd, 2H, J=4.1, 11.7 Hz), 3.01 (s, 3H), 2.89 (dd, 1H, J=5.4, 13.6 Hz), 2.55 (bs, 1H), 1.50 (d, 3H, J=7.1 Hz), 1.19 (s, 9H)

MS(FAB) m/z 492 ($MH^+$)

Example 128

Preparation of N-[(2S)-3-phenyl-1-pivaloyloxy-2-propyl]-N'-[(S)-α-methyl-4-(methylsulfonylamino)benzyl]thiourea (19-16, SU-710)

Step 128-1. Preparation of N-[(2S)-3-phenyl-1-pivaloyloxy-2-propyl]-N'-[(S)-α-methyl-4-nitrobenzyl]thiourea (19-8, SU-700)

The N-[(2S)-3-phenyl-1-pivaloyloxy-2-propyl]-N'-[(S)-α-methyl-4-nitrobenzyl]thiourea (19-8, SU-700) was prepared by the similar procedure with that described in above Example 127-1, 127-2 and 127-3.

82% yield, yellow oil

The spectral data of this compound were identical to those of compound 19-7.

Step 128-2. Preparation of N-[(2S)-3-phenyl-1-pivaloyloxy-2-propyl]-N'-[(S)-α-methyl-4-aminobenzyl]thiourea (19-12, SU-706)

Through similar procedure to that in Example 125-4 excepting using N-[(2S)-3-phenyl-1-pivaloyloxy-2-propyl]-N'-[(S)-α-methyl-4-nitrobenzyl]thiourea (19-8) as a starting material, N-[(2S)-3-phenyl-1-pivaloyloxy-2-propyl]-N'-[(S)-α-methyl-4-aminobenzyl]thiourea (19-12, SU-706) having following physicochemical properties was synthesized:

93% yield, yellow oil

The spectral data of this compound were identical to those of compound 19-11.

Step 128-3. Preparation of N-[(2S)-3-phenyl-1-pivaloyloxy-2-propyl]-N'-[(S)-α-methyl-4-(methylsulfonylamino)benzyl]thiourea (19-16. SU-710)

Through similar procedure to that in Example 125-5 excepting using N-[(2S)-3-phenyl-1-pivaloyloxy-2-propyl]-N'-[(S)-α-methyl-4-aminobenzyl]thiourea (19-12) as a starting material, N-[(2S)-3-phenyl-1-pivaloyloxy-2-propyl]-N'-[(S)-α-methyl-4-(methylsulfonylamino)benzyl]thiourea (19-16, SU-710) having following physicochemical properties was synthesized:

85% yield, white solid, mp=59-61° C., [α]=−18.2 (c 1.00, $CHCl_3$)

The spectral data of this compound were identical to those of compound 19-15.

MS (FAB) m/z 492 ($MH^+$)

Example 129

Preparation of N-(4-t-Butylbenzyl)-N'-{1-[4-(methylsulfonylamino)-3-fluorophenyl]propyl}thiourea (20-12, LJO-399)

Step 129-1. Preparation of 2-Fluoro-4-vinylaniline (20-1, LJO-324)

A solution of 2-fluoro-4-iodoaniline (2.37 g, 10 mmol) in toluene (50 mL) was treated with tetrakis(triphenylphosphine)palladium (0.578 g, 0.5 mmol), tributylvinyltin (3.5 mL, 12 mmol) and a catalytic amount of 2,6-di-tert-butyl-4-methylphenol. After being heated at 100° C. for 1 h, the reaction mixture was filtered through celite and the filtrate was concentrated in vacuo. The residue was purified by flash column chromatography on silica gel using EtOAc:hexanes (1:5) as eluant to afford 2-Fluoro-4-vinylaniline (20-1, LJO-324, 1.275 g, 93%) as a yellow oil.

$^1$H NMR ($CDCl_3$) δ 7.08 (dd, 1H, J=1.95, 12.4 Hz), 6.98 (dd, 1H, J=1.47 Hz, 8.04 Hz), 6.71 (t, 1H, J=9 Hz), 6.57 (dd, 1H, J=10.8, 17.5 Hz), 5.55 (d, 1H, J=17.5 Hz), 5.09 (dd, 1H, J=10.8 Hz), 3.75 (bs, 2H)

Step 129-2. Preparation of N-(2-Fluoro-4-vinylphenyl)methanesulfonamide (20-2, LJO-325)

A cooled solution of 2-Fluoro-4-vinylaniline (20-1, 0.96 g, 7 mmol) in pyridine (10 mL) at 0° C. was treated with methanesulfonyl chloride (0.644 mL, 8.4 mmol) and stirred at room temperature for 30 min. The reaction mixture was diluted with water and extracted with EtOAc several times. The combined organic layers were washed with water and brine, dried over $MgSO_4$, filtered, and the filtrate was concentrated in vacuo. The residue was purified by flash column chromatography on silica gel using EtOAc:hexanes (1:3) as eluant to afford N-(2-Fluoro-4-vinylphenyl)methanesulfonamide (20-2, LJO-325, 1.372 g, 91%) as a white solid.

mp=82° C.

$^1$H NMR ($CDCl_3$) δ 7.53 (t, 1H, J=8 Hz), 7.15-7.25 (m, 2H), 6.64 (dd, 1H, J=10.7, 17.5 Hz), 6.50 (bs, 1H), 5.72 (d, 1H, J=17.5 Hz), 5.32 (dd, 1H, J=10.7 Hz), 3.03 (s, 3H)

Step 129-3. Preparation of N-(2-Fluoro-4-formylphenyl)methansulfonamide (20-3. LJO-326)

A solution of N-(2-Fluoro-4-vinylphenyl)methansulfonamide (20-2, 1.076 g, 5 mmol) in acetone and water (1:1, 20 mL) was treated with a catalytic amount of osmium tetroxide (4 wt % solution in hydroxyperoxide) and sodium periodate (2.139 g, 10 mmol). After being stirred at room temperature for 1 h, the mixture was concentrated into a small volume in vacuo. The residue was treated with aqueous sodium thiosulfate solution and then extracted with EtOAc several times. The combined organic layers were washed with water and brine, dried over $MgSO_4$, filtered, and the filtrate was concentrated in vacuo. The residue was purified by flash column chromatography on silica gel using EtOAc:hexanes (1:2) as eluant to afford N-(2-Fluoro-4-formylphenyl)methanesulfonamide (20-3, LJO-326, 0.521 g, 48%) as a white solid. mp=151° C.
$^1$H NMR (CDCl$_3$) δ 9.92 (d, 1H, J=2.2 Hz), 7.78 (t, 1H, J=8.6 Hz), 7.65-7.74 (m, 2H), 6.92 (bs, 1H), 3.15 (s, 3H)

Step 129-4. Preparation of N-[2-fluoro-4-(1-hydroxypropyl)phenyl]methansulfonamide (20-4, LJO-337)

A cooled solution of N-(2-Fluoro-4-formylphenyl)methansulfonamide (20-3, 0.424 g, 2 mmol) in THF (20 mL) at 0° C. was treated with Grignard reagent (4 mmol) and stirred at 0° C. for 30 min. The reaction mixture was quenched with saturated ammonium chloride solution, diluted with water and extracted with EtOAc several times. The combined organic layers were washed with water and brine, dried over MgSO$_4$, filtered, and the filtrate was concentrated in vacuo. The residue was purified by flash column chromatography on silica gel using EtOAc:hexanes (1:1) as eluant to N-[2-fluoro-4-(1-hydroxypropyl)phenyl]methanesulfonamide (20-4, LJO-337).
92% yield, colorless oil
$^1$H NMR (CDCl$_3$) δ 7.53 (t, 1H, J=8.22 Hz), 7.19 (dd, 1H, Jo-1.8, 11.2 Hz), 7.12 (dd, 1H, J=1.8 Hz, 8 Hz), 6.45 (bs, 1H), 4.61 (m, 1H), 3.02 (s, 3H), 1.87 (m, 1H), 1.7-1.8 (m, 2H), 0.93 (t, 3H, J=7.3 Hz)

Step 129-5. Preparation of N-[2-fluoro-4-(1-azidopropyl)phenyl]methanesulfonamide (20-8, LJO-397)

A cooled solution of the alcohol (1 mmol) in toluene (10 mL) at 0° C. was treated with diphenylphosphorylazide (0.26 mL, 1.2 mmol) followed by 1,8-diazabicyclo[5,4,0]undec-7-ene (0.18 mL, 1.2 mmol) and stirred for 2 h at 0° C. After being further stirred for 20 h at room temperature, the reaction mixture was diluted with EtOAc. The organic layer was washed with 5% HCl (10 mL), water and brine, dried over MgSO$_4$, filtered, and the filtrate was concentrated in vacuo. The residue was purified by flash column chromatography on silica gel using EtOAc:hexanes (1:3) as eluant to afford N-[2-fluoro-4-(1-azidopropyl)phenyl]methanesulfonamide (20-8, LJO-397).
91% yield, colorless oil
$^1$H NMR (CDCl$_3$) δ 7.56 (t, 1H, J=8.04 Hz), 7.0-7.1 (m, 2H), 6.70 (bs, 1H), 4.34 (t, 1H, J=7.32 Hz), 3.03 (s, 3H), 1.7-1.8 (m, 2H), 0.93 (t, 3H, J=7.3 Hz)

Step 129-6. Preparation of N-(4-t-Butylbenzyl-N'-{1-[4-(methylsulfonylamino)-3-fluorophenyl]propyl}thiourea (20-12, LJO-399)

A suspension of the azide (1 mmol) and 10% palladium on carbon (50 mg) in MeOH (10 mL) was hydrogenated under a balloon of hydrogen for 1 h. The reaction mixture was filtered and the filtrate was concentrated in vacuo. The residue was dissolved in DMF (3 mL) and then added 4-tert-butylbenzyl isothiocyanate (0.205 g, 1 mmol). After being stirred at room temperature for 3 h, the reaction mixture was diluted with water and extracted with EtOAc several times. The combined organic layers were washed with water and brine, dried over MgSO$_4$, filtered, and the filtrate was concentrated in vacuo. The residue was purified by flash column chromatography on silica gel with EtOAc:hexanes (1:1) as eluant to afford N-(4-t-Butylbenzyl)-N'-{1-[4-(methylsulfonylamino)-3-fluorophenyl]propyl}thiourea (20-12, LJO-399).
82% yield, white solid, mp=85° C.
$^1$H NMR (CDCl$_3$) δ 7.45 (t, 1H, J=8.04 Hz), 7.34 (d, 2H, J=8.04 Hz), 7.12 (d, 2H, J=8.04 Hz), 6.9-7.0 (m, 2H), 6.76 (bs, 1H), 6.24 (bs, 2H), 4.88 (bs, 1H), 4.55 (bs, 2H), 3.00 (s, 3H), 1.7-1.8 (m, 2H), 1.30 (s, 9H), 0.82 (t, 3H, J=7.05 Hz)
MS (FAB) m/z 452 (MH$^+$)

Example 130

Preparation of N'-(4-t-Butylbenzyl)-N-{1-[4-(methylsulfonylamino)-3-fluorophenyl]-2-methylpropyl}thiourea (20-13, LJO-402)

Step 130-1. Preparation of N-[2-fluoro-4-(1-hydroxy-2-methylpropyl)phenyl]methanesulfonamide (20-5. LJO-3960)

Through similar procedure to that in Example 129-5 excepting using N-(2-Fluoro-4-formylphenyl)methanesulfonamide (20-3) as a starting material, N-[2-fluoro-4-(1-hydroxy-2-methylpropyl)phenyl]methanesulfonamide (20-5, LJO-396) having following physicochemical properties was synthesized:
90% yield, colorless oil
$^1$H NMR (CDCl$_3$) δ 7.50 (t, 1H, J=8.28 Hz), 7.15 (dd, 1H, J=1.95, 11.2 Hz), 7.07 (dd, 1H, J=1.8 Hz, 8 Hz), 6.62 (bs, 1H), 4.38 (d, 1H, J=6.36 Hz), 3.01 (s, 3H), 1.80 (m, 2H), 0.95 (d, 3H, J=6.8 Hz), 0.83 (d, 3H, J=6.8 Hz)

Step 130-2. Preparation of N-[2-fluoro-4-(1-azido-2-methylpropyl)phenyl]methanesulfonamide (20-9. LJO-398)

Through similar procedure to that in Example 129-5 excepting using N-[2-fluoro-4-(1-hydroxy-2-methylpropyl)phenyl]methanesulfonamide (20-5) as a starting material, N-[2-fluoro-4-(1-azido-2-methylpropyl)phenyl]methanesulfonamide (20-9, LJO-398) having following physicochemical properties was synthesized:
85% yield, colorless oil
$^1$H NMR (CDCl$_3$) δ 7.57 (t, 1H, J=8.07 Hz), 7.05-7.15 (m, 2H), 6.64 (bs, 1H), 4.15 (d, 1H, J=7.56 Hz), 3.05 (s, 3H), 1.93 (m, 1H), 0.99 (d, 3H, J=6.8 Hz), 0.81 (d, 3H, J=6.8 Hz)

Step 130-3. Preparation of N'-(4-t-Butylbenzyl)-N-{1-[4-(methylsulfonylamino)-3-fluorophenyl]-2-methylpropyl}thiourea (20-13. LJO-402)

Through similar procedure to that in Example 129-6 excepting using N-[2-fluoro-4-(1-azido-2-methylpropyl)phenyl]methanesulfonamide (20-9) as a starting material, N'-(4-t-Butylbenzyl)-N-{1-[4-(methylsulfonylamino)-3-fluorophenyl]-2-methylpropyl}thiourea (20-13, LJO-402) having following physicochemical properties was synthesized:
87% yield, white solid, mp=84° C.
$^1$H NMR (CDCl$_3$) δ 7.45 (t, 1H, J=8.04 Hz), 7.36 (d, 2H, J=8.04 Hz), 7.14 (d, 2H, J=8.04 Hz), 6.85-6.95 (m, 2H), 6.78 (bs, 1H), 6.25 (bs, 2H), 4.81 (bs, 1H, 4.53 (bs, 2H), 3.01 (s, 3H), 1.92 (m, 1H), 1.30 (s, 9H), 0.77 (m, 6H)
MS (FAB) m/z 466 (MH$^+$)

Example 131

Preparation of N-(4-t-Butylbenzyl)-N'-{([4-(methylsulfonylamino)-3-fluorophenyl](phenyl)methyl}thiourea (20-14, LJO-403)

Step 131-1. Preparation of N-{2-fluoro-4-[hydroxy(phenyl)methyl]phenyl}methanesulfonamide (20-6, LJO-330)

Through similar procedure to that in Example 129-4 excepting using Grignard reagent (R=Ph) of N-(2-Fluoro-4-formylphenyl)methanesulfonamide (20-3) as a starting material, N-{2-fluoro-4-[hydroxy(phenyl)methyl]phenyl}methanesulfonamide (20-6, LJO-330) having following physicochemical properties was synthesized:

100% yield, white solid, mp=91° C.

$^1$H NMR (CDCl$_3$) δ 7.52 (t, 1H, J=8.25 Hz), 7.3-7.38 (m, 5H), 7.22 (dd, 1H, J=1.6, 11.2 Hz), 7.17 (dd, 1H, J=1.6 Hz, 8 Hz), 6.46 (bs, 1H), 5.81 (s, 1H), 3.00 (s, 3H), 1.99 (bs, 1H)

Step 131-2. Preparation of N-{2-fluoro-4-[azido(phenyl)methyl]phenyl}methanesulfonamide (20-10, LJO-335)

Through similar procedure to that in Example 129-5 excepting using N-{2-fluoro-4-[hydroxy(phenyl)methyl]phenyl}methanesulfonamide (20-6) as a starting material, N{2-fluoro-4-[azido(phenyl)methyl]phenyl}methanesulfonamide (20-10, LJO-335) having following physicochemical properties was synthesized:

84% yield, white solid, mp=60° C.

$^1$H NMR (CDCl$_3$) δ 7.56 (t, 1H, J=8.25 Hz), 7.25-7.45 (m, 5H), 7.1-7.15 (m, 2H), 6.48 (bs, 1H), 5.68 (s, 1H), 3.03 (s, 3H)

Step 131-3. Preparation of N-(4-t-Butylbenzyl)-N'-{[4-(methylsulfonylamino)-3-fluorophenyl]phenyl)methyl}thiourea (20-14, LJO-403)

Through similar procedure to that in Example 129-6 excepting using N-{2-fluoro-4-[hydroxy(phenyl)methyl]phenyl}methanesulfonamide (20-6) as a starting material, N-(4-t-Butylbenzyl)-N'-{[4-(methylsulfonylamino)-3-fluorophenyl](phenyl)methyl}thiourea (20-14, LJO-403) having following physicochemical properties was synthesized:

92% yield, white solid, mp=191° C.

$^1$H NMR (CDCl$_3$) δ 7.50 (t, 1H, J=8.55 Hz), 7.25-7.4 (m, 7H), 7.13 (d, 2H, J=8.04 Hz), 6.9-7.0 (m, 2H), 6.51 (bs, 1H), 6.30 (bs, 1H), 6.23 (bs, 1H), 4.58 (bs, 2H), 3.02 (s, 3H), 1.31 (s, 9H)

MS (FAB) m/z 500 (MH$^+$)

Example 132

Preparation of N-(4-t-Butylbenzyl)-N'-{1-[4-(methylsulfonylamino)-3-fluorophenyl]-2-phenylethyl}thiourea (20-15, LJO-395)

Step 132-1. Preparation of N-[2-fluoro-4-(1-hydroxy-2-phenylethyl)phenyl]methanesulfonamide (20-7, LJO-336)

Through similar procedure to that in Example 129-4 excepting using Grignard reagent (R=Ph) of N-(2-Fluoro-4-formylphenyl)methanesulfonamide (20-3) as a starting material, N-[2-fluoro-4-(1-hydroxy-2-phenylethyl)phenyl]methanesulfonamide (20-7, LJO-336) having following physicochemical properties was synthesized:

94% yield, yellow solid, mp=123° C.

$^1$H NMR (CDCl$_3$) δ 7.54 (t, 1H, J=8.22 Hz), 7.1-7.35 (m, 7H), 6.44 (bs, 1H), 4.89 (m, 1H), 3.02 (s, 3H), 2.98 (ddd of AB, 2H), 1.98 (d, 1H, J=2.9 Hz)

Step 132-2. Preparation of N-[2-fluoro-4-(1-azido-2-phenylethyl)phenyl]methanesulfonamide (20-11, LJO-394)

Through similar procedure to that in Example 129-5 excepting using N-[2-fluoro-4-(1-hydroxy-2-phenylethyl)phenyl]methanesulfonamide (20-7) as a starting material, N-[2-fluoro-4-(1-azido-2-phenylethyl)phenyl]methanesulfonamide (20-11, LJO-394) having following physicochemical properties was synthesized:

94% yield, white solid, mp=74° C.

$^1$H NMR (CDCl$_3$) δ 7.55 (t, 1H, J=8.04 Hz), 7.0-7.3 (m, 7H), 6.62 (bs, 1H), 4.66 (t, 1H, J=6.84 Hz), 3.04 (s, 3H), 3.00 (ddd of AB, 2H)

Step 132-3. Preparation of N-(4-t-Butylbenzyl)-N'-{1-[4-(methylsulfonylamino)-3-fluorophenyl]-2-phenylethyl}thiourea (20-15, LJO-395)

Through similar procedure to that in Example 129-6 excepting using N-[2-fluoro-4-(1-azido-2-phenylethyl)phenyl]methanesulfonamide (20-11) as a starting material, N-(4-t-Butylbenzyl)-N'-{1-[4-(methylsulfonylamino)-3-fluorophenyl]-2-phenylethyl}thiourea (20-15, LJO-395) having following physicochemical properties was synthesized:

93% yield, white solid, mp=116° C.

$^1$H NMR (CDCl$_3$) δ 7.43 (t, 1H, J=8.04 Hz), 7.33 (d, 2H, J=8.04 Hz), 7.2-7.3 (m, 5H), 7.06 (d, 2H, J=8.04 Hz), 6.9-7.0 (m, 2H), 6.63 (bs, 1H), 6.11 (bs, 1H), 5.45 (bs, 1H), 4.43 (bs, 2H), 3.06 (d, 2H, J=5.6 Hz), 3.00 (s, 3H), 1.31 (s, 9H)

MS (FAB) m/z 514 (MH$^+$)

Example 133

Preparation of N-(4-t-Butylbenzyl)-N'-{1-methyl-1-[4-(methylsulfonylamino)phenyl]ethyl}thiourea (21-7, CHK-593)

Step 133-1. Preparation of Benzyl N-{1-Methyl-1-[4-(methylsulfonylamino)phenyl]ethyl}carbamate (21-1, CHK-582)

A solution of 2-[4-(methylsulfonylamino)phenyl]-2-methylpropionic acid (8-11, 1 mmol) in toluene (6 mL) was treated with 4A molecular sieve (200 mg), Et$_3$N (1.3 mmol) and diphenylphosphoryl azide (1.3 mmol) and heated at 110° C. for 1 h. The mixture was cooled to room temperature and BnOH (20 mmol) was added. After the mixture was heated to 110° C. for 12 hours and concentrated in vacuo. The residue was purified by column chromatography on silica gel with EtOAc:hexanes as eluant to afford Benzyl N-{1-Methyl-1-[4-(methylsulfonylamino)phenyl]ethyl}carbamate (21-1, CHK-582)

$^1$H NMR (CDCl$_3$) δ 7.25-7.4 (m, 7H), 7.12 (bd, 2H), 6.60 (bs, 1H), 5.22 (bs, 1H), 5.02 (s, 2H), 2.98 (s, 3H), 1.65 (s, 6H)

Step 133-2. Preparation of N-(4-t-Butylbenzyl)-N'-{1-methyl-1-[4-(methylsulfonylamino)phenyl]ethyl}thiourea (21-7, CHK-593)

A suspension of Benzyl N-{1-Methyl-1-[4-(methylsulfonylamino)phenyl]ethyl}carbamate (21-1, 0.5 mmol) and 5% palladium on carbon (100 mg) in MeOH (10 mL) was hydrogenated under a rubber balloon of hydrogen for 1 h. After the solvent was evaporated by rotary evaporator, the residue was dissolved in DMF (5 mL) and treated with 4-t-butylbenzyl isothiocyanate (0.5 mmol). After being stirred overnight, the mixture went to aqueous work-up and the residue was purified by column chromatography on silica gel with EtOAc: hexanes as eluant to afford N-(4-t-Butylbenzyl)-N'-{1-methyl-1-[4-(methylsulfonylamino)phenyl]ethyl}thiourea (21-7, CHK-593)

94% yield, white solid, mp=161-164° C.

$^1$H NMR (CDCl$_3$) δ 7.42 (d, 2H), 7.22 (dd, 4H), 6.83 (bs, 1H), 6.80 (d, 2H), 6.63 (bs, 1H), 5.23 (bt, 1H), 4.58 (d, 2H, J=4.9 Hz), 2.97 (s, 3H), 1.65 (s, 6H), 1.28 (s, 9H)

MS (FAB) m/z 434 (MH$^+$)

Example 134

Preparation of N-(4-t-Butylbenzyl)-N'-{1-methyl-1-[3-fluoro-4-(methylsulfonylamino)phenyl]ethyl}thiourea (21-8, CHK-660)

Step 134-1. Preparation of Benzyl N-{1-Methyl-1-[3-fluoro-4-(methylsulfonylamino)phenyl]ethyl}carbamate (21-2, CHK-657)

Through similar procedure to that in Example 133-1 excepting using 2-[3-Fluoro-4-(methylsulfonylamino)phenyl]-2-methylpropionic acid (7-4) as a starting material, Benzyl N-{1-Methyl-1-[3-fluoro-4-(methylsulfonylamino)phenyl]ethyl}carbamate (21-2, CHK-657) having following physicochemical properties was synthesized:

$^1$H NMR (CDCl$_3$) δ 7.50 (t, 1H, J=8.3 Hz), 7.34 (bs, 5H), 7.15-7.2 (m, 2H), 6.45 (bs, 1H), 5.18 (bs, 1H), 5.02 (s, 2H), 3.02 (s, 3H), 1.63 (s, 6H)

Step 134-2. Preparation of N-(4-t-Butylbenzyl)-N'-{1-methyl-1-[3-fluoro-4-(methylsulfonylamino)phenyl]ethyl}thiourea (21-8, CHK-660)

Through similar procedure to that in Example 133-2 excepting using Benzyl N-{1-Methyl-1-[3-fluoro-4-(methylsulfonylamino)phenyl]ethyl}carbamate (21-2) as a starting material, Benzyl N-{1-Methyl-1-[3-fluoro-4-(methylsulfonylamino)phenyl]ethyl}carbamate (21-2, CHK-657) having following physicochemical properties was synthesized:

80% yield, white solid, mp=83-85° C.

$^1$H NMR (CDCl$_3$) δ 7.52 (t, 1H, J=8.2 Hz), 7.18-7.3 (m, 4H), 6.86 (d, 2H, J=7.9 Hz), 6.50 (bs, 1H), 5.20 (bs, 1H), 4.59 (d, 2H, J=4.8 Hz), 2.98 (s, 3H), 1.65 (s, 6H), 1.29 (s, 9H)

MS m/z 486 (MNa$^+$)

Example 135

Preparation of N-(4-t-Butylbenzyl)-N'-{1-methyl-1-[3-methoxy-4-(methylsulfonylamino)phenyl]ethyl}thiourea (21-9, CHK-629)

Step 135-1. Preparation of Benzyl N-{1-Methyl-1-[3-methoxy-4-(methylsulfonylamino)phenyl]ethyl}carbamate (21-3, CHK-646)

Through similar procedure to that in Example 133-1 excepting using 2-(3-methoxy-4-(methylsulfonylamino)phenyl)-2-methylpropionic acid (8-12) as a starting material, Benzyl N-{1-Methyl-1-[3-methoxy-4-(methylsulfonylamino)phenyl]ethyl}carbamate (21-3, CHK-646) having following physicochemical properties was synthesized:

$^1$H NMR (CDCl$_3$) δ 7.44 (d, 1H, J=8.3 Hz), 7.34 (bs, 5H), 6.98 (dd, 1H, J=2, 8.3 Hz), 6.91 (d, 1H, J=2 Hz), 6.74 (bs, 1H), 5.21 (bs, 1H), 5.02 (s, 2H), 3.79 (s, 3H), 2.93 (s, 3H), 1.65 (s, 6H)

Step 135-2. Preparation of N-(4-t-Butylbenzyl)-N'-{1-methyl-1-[3-methoxy-4-(methylsulfonylamino)phenyl]ethyl}thiourea (21-9, CHK-629)

Through similar procedure to that in Example 135-1 excepting using Benzyl N-{1-Methyl-1-[3-methoxy-4-(methylsulfonylamino)phenyl]ethyl}carbamate (21-3) as a starting material, N-(4-t-Butylbenzyl)-N'-{1-methyl-1-[3-methoxy-4-(methylsulfonylamino)phenyl]ethyl}thiourea (21-9, CHK-629) having following physicochemical properties was synthesized:

69% yield, white solid, mp=148-150° C.

$^1$H NMR (CDCl$_3$) δ 7.47 (d, 1H, J=8.2 Hz), 7.23 (d, 1H), 6.94-7.0 (m, 2H), 6.80 (d, 3H), 6.50 (bs, 1H), 5.31 (t, 1H), 4.57 (d, 2H, J=5.1 Hz), 3.77 (s, 3H), 2.89 (s, 3H), 1.65 (s, 6H), 1.29 (s, 9H)

MS (FAB) m/z 464 (MH$^+$)

Example 136

Preparation of N-(4-t-Butylbenzyl)-N'-{1-[4-(methylsulfonylamino)phenyl]cyclopropyl}thiourea (22-7, CHK-579)

Step 136-1. Preparation of Benzyl N-{1-[4-(methylsulfonylamino)phenyl]cyclopropyl}carbamate (22-1, CHK-577)

Through similar procedure to that in Example 135-1 excepting using 1-[4-(Methylsulfonylamino)phenyl]cyclopropanecarboxylic acid (11-7, CHK-530) as a starting material, N-(4-t-Butylbenzyl)-N'-{1-methyl-1-[3-methoxy-4-(methylsulfonylamino)phenyl]ethyl}thiourea (21-9, CHK-629) having following physicochemical properties was synthesized:

77% yield, white solid, mp=142-143° C.

$^1$H NMR (CDCl$_3$) δ 7.35 (bs, 5H), 7.24 (bd, 2H), 7.13 (bd, 2H), 6.32 (bs, 1H), 5.46 (bs, 1H), 5.09 (s, 2H), 2.98 (s, 3H), 1.2-1.35 (m, 4H)

Step 136-2. Preparation of N-(4-t-Butylbenzyl)-N'-{1-[4-(methylsulfonylamino)phenyl]cyclopropyl}thiourea (22-7, CHK-579)

Through similar procedure to that in Example 133-2 excepting using 1-[4-(Methylsulfonylamino)phenyl]cyclopropanecarboxylic acid (11-7) as a starting material, N-(4-t-Butylbenzyl)-N'-{1-[4-(methylsulfonylamino)phenyl]cyclopropyl}thiourea (22-7, CHK-579) having following physicochemical properties was synthesized:

78% yield, white solid, mp=110-113° C.

$^1$H NMR (CDCl$_3$) δ 7.33 (d, 2H), 7.17 (m, 4H), 7.05 (d, 2H), 4.58 (m, 2H), 3.01 (s, 3H), 1.7-1.9 (m, 2H), 0.85 (t, 2H, J=7.5 Hz)

MS (FAB) m/z 433 (M$^+$+2)

Example 137

Preparation of N-(4-t-Butylbenzyl)-N'-{1-[3-fluoro-4-(methylsulfonylamino)phenyl]cyclopropyl}thiourea (22-8)

Step 137-1. Preparation of Benzyl N-{1-[3-fluoro-4-(Methylsulfonylamino)phenyl]cyclopropyl}carbamate (22-2)

Through similar procedure to that in Example 133-2 excepting using 1-[3-fluoro-4-(methylsulfonylamino)phenyl]cyclopropanecarboxylic acid (10-6) as a starting material, Benzyl N-{1-[3-fluoro-4-(Methylsulfonylamino)phenyl]cyclopropyl}carbamate (22-2) having following physicochemical properties was synthesized:

$^1$H NMR (CDCl$_3$) δ 7.50 (t, 1H), 7.35 (bs, 5H), 6.90 (d, 1H), 6.84 (dd, 1H), 6.68 (bs, 1H, NHSO$_2$), 5.48 (bs, 1H), 5.12 (s, 2H), 2.93 (s, 3H), 1.2-1.3 (m, 4H)

Step 137-2. Preparation of N-(4-t-Butylbenzyl)-N'-{1-[3-fluoro-4-(methylsulfonylamino)phenyl]cyclopropyl}thiourea (22-8)

Through similar procedure to that in Example 133-2 excepting using Benzyl N-{1-[3-fluoro-4-(Methylsulfonylamino)phenyl]cyclopropyl}carbamate (22-2) as a starting material, N-(4-t-Butylbenzyl)-N'-{1-[3-fluoro-4-(methylsulfonylamino)phenyl]cyclopropyl}thiourea (22-8) having following physicochemical properties was synthesized:

$^1$H NMR (CDCl$_3$) δ 7.53 (t, 1H), 7.34 (d, 1H), 7.05 (d, 2H), 6.75-6.90 (m, 3H), 6.23 (bs, 1H), 5.80 (bs, 1H), 4.58 (ddd, 2H), 2.95 (s, 3H), 1.7-1.9 (m, 2H), 1.30 (s, 9H), 0.88 (t, 2H)

MS (FAB) m/z 450 (MH$^+$)

Example 138

Preparation of N-(4-t-Butylbenzyl)-N'-{1-[3-methoxy-4-(methylsulfonylamino)phenyl]cyclopropyl}thiourea (22-9, CHK-631)

Step 138-1. Preparation of Benzyl N-{1-[3-methoxy-4-(Methylsulfonylamino)phenyl]cyclopropyl}carbamate (22-3, CHK-627)

Through similar procedure to that in Example 133-1 excepting using 1-[3-Methoxy-4-(methylsulfonylamino)phenyl]cyclopropanecarboxylic acid (11-8) as a starting material, Benzyl N-{1-[3-methoxy-4-(Methylsulfonylamino)phenyl]cyclopropyl}carbamate (22-3, CHK-627) having following physicochemical properties was synthesized:

86% yield, white solid, mp=100-103° C.

$^1$H NMR (CDCl$_3$) δ 7.42 (d, 1H, J=8.3 Hz), 7.35 (bs, 5H), 6.88 (d, 1H, J=1.8 Hz), 6.82 (dd, 1H, J=1.8, 8.3 Hz), 6.68 (bs, 1H), 5.46 (bs, 1H), 5.09 (s, 2H), 3.79 (s, 3H), 2.91 (s, 3H), 1.2-1.3 (m, 4H)

Step 138-2. Preparation of N-(4-t-Butylbenzyl)-N'-{1-[3-methoxy-4-(methylsulfonylamino)phenyl]cyclopropyl}thiourea (22-9, CHK-631)

Through similar procedure to that in Example 133-2 excepting using Benzyl N-{1-[3-methoxy-4-(Methylsulfonylamino)phenyl]cyclopropyl}carbamate (22-3) as a starting material, N-(4-t-Butylbenzyl)-N'-{1-[3-methoxy-4-(methylsulfonylamino)phenyl]cyclopropyl}thiourea (22-9, CHK-631) having following physicochemical properties was synthesized:

86% yield, white solid, mp=100-103° C.

$^1$H NMR (CDCl$_3$) δ 7.46 (d, 1H), 7.31 (d, 1H), 7.02 (d, 2H), 6.7-6.85 (m, 3H), 6.20 (bs, 1H), 5.78 (bs, 1H), 4.58 (ddd, 2H), 3.83 (s, 3H), 2.94 (s, 3H), 1.7-1.9 (m, 2H), 1.30 (s, 9H), 0.88 (t, 2H, J=7.5 Hz)

MS (FAB) m/z 463 (M$^+$+2)

Example 139

Preparation of N-(4-t-Butylbenzyl)-N'-{1-[4-(methylsulfonylamino)phenyl]ethyl}urea (23-1, MK-82)

Through similar procedure to that in Example 133-2 excepting using 1-[4-(Methylsulfonylamino)phenyl]ethyl amine (13-11) as a starting material, N-(4-t-Butylbenzyl)-N'-{1[4-(methylsulfonylamino)phenyl]ethyl}urea (23-1, MK-82) having following physicochemical properties was synthesized:

83% yield, white solid, mp=95-98° C.

$^1$H NMR (CDCl$_3$) δ 7.34 (d, 2H, J=8.3 Hz), 7.23 (d, 2H, J=8.5 Hz), 7.16 (d, 2H, J=8.3 Hz), 7.11 (d, 2H, J=8.5 Hz), 6.86 (s, 1H), 4.82 (m, 1H), 4.63 (m, 2H), 4.31 (d, 2H, J=4.4 Hz), 2.97 (s, 3H), 1.40 (d, 3H, J=6.8 Hz), 1.30 (s, 9H)

MS (EI) m/z 403 (M$^+$)

Example 140

Preparation of N-(4-t-Butylbenzyl)-N'-{1-[3-fluoro-4-(methylsulfonylamino)phenyl]ethyl}urea (23-2, MK-205)

Through similar procedure to that in Example 102 excepting 1-[3-Fluoro-4-(methylsulfonylamino)phenyl]ethyl amine (13-12) as a starting material, N-(4-t-Butylbenzyl)-N'-{1-[4-(methylsulfonylamino)phenyl]ethyl}urea (23-1, MK-82) having following physicochemical properties was synthesized:

70% yield, white solid, mp=152-154° C.

$^1$H NMR (CDCl$_3$) δ 7.44 (t, 1H, J=8.2 Hz), 7.34 (bd, 2H, J=8.5 Hz), 7.18 (bd, 2H, J=8.3 Hz), 7.0-7.08 (m, 2H), 6.66 (s, 1H), 4.84 (m, 1H), 4.75 (m, 2H), 4.30 (ddd, 2H), 2.99 (s, 3H), 1.38 (d, 3H, J=6.8 Hz), 1.30 (s, 9H)

MS (FAB) m/z 422 (MH$^+$)

Example 141

Preparation of N-{1-[3-Fluoro-4-(methylsulfonylamino)phenyl]ethyl}-3-(4-tert-butylphenyl)acetamide (24-1, KMJ-586)

The N-{1-[3-Fluoro-4-(methylsulfonylamino)phenyl]ethyl}-3-(4-tert-butylphenyl)acetamide (24-1) was prepared by the similar procedure with that described in above Example 1-5.

36% yield, white solid, mp=134-136° C.

$^1$H NMR (CDCl$_3$) δ 7.48 (t, 1H, J=8.8 Hz), 7.39 (bd, 2H, J=8.3 Hz), 7.18 (bd, 2H, J=8.3 Hz), 6.92-7.02 (m, 2H), 6.44 (bs, 1H), 5.58 (d, 1H, J=7.8 Hz), 5.06 (m, 1H), 3.56 (s, 2H), 3.00 (s, 3H), 1.37 (d, 3H, J=7 Hz), 1.33 (s, 9H)

MS (FAB) m/z 407 (MH$^+$)

Example 142

Preparation of N-{1-[3-Fluoro-4-(methylsulfonylamino)phenyl]ethyl}-3-(4-tert-butylphenyl)propanamide (24-2, KMJ-552)

The N-{1-[3-Fluoro-4-(methylsulfonylamino)phenyl]ethyl}-3-(4-tert-butylphenyl)propanamide (24-2) was prepared by the similar procedure with that described in above Example 1-5.

29% yield, white solid, mp=152-154° C.
$^1$H NMR (CDCl$_3$) δ 7.44 (t, 1H, J=8 Hz), 7.31 (bd, 2H, J=8.3 Hz), 7.11 (bd, 2H, J=8.3 Hz), 6.95-7.02 (m, 2H), 6.82 (bs, 1H), 5.72 (d, 1H, J=7.1 Hz), 5.02 (m, 1H), 3.00 (s, 3H), 2.93 (t, 2H, J=7.1 Hz), 2.50 (m, 2H), 1.34 (d, 3H, J=7 Hz), 1.30 (s, 9H)
MS (FAB) m/z 421 (MH$^+$)

Example 143

Preparation of N-{1-[3-Fluoro-4-(methylsulfonylamino)phenyl]ethyl}-3-(4-tert-butylphenyl)-2-propenamide (24-3, KMJ-570)

The N-{1-[3-Fluoro-4-(methylsulfonylamino)phenyl]ethyl}-3-(4-tert-butylphenyl)-2-propenamide (24-3) was prepared by the similar procedure with that described in above Example 1-5.

67% yield, white solid, mp=154-156° C.
$^1$H NMR (CDCl$_3$) δ 7.62 (d, 1H, J=15.5 Hz), 7.52 (t, 1H, J=8 Hz), 7.41 (dd, 4H), 7.12-7.18 (m, 2H), 6.54 (bs, 1H), 6.37 (d, 1H, J=15.5 Hz), 5.88 (d, 1H, J=7.1 Hz), 5.21 (m, 1H), 3.02 (s, 3H), 1.53 (d, 3H, J=7 Hz), 1.32 (s, 9H)
MS (FAB) m/z 419 (MH$^+$)

Example 144

Preparation of N-{1-[3-Fluoro-4-(methylsulfonylamino)phenyl]ethyl}-3-(3,4-dimethylphenyl)propanamide (24-4, CHK-602)

The N-{1-[3-Fluoro-4-(methylsulfonylamino)phenyl]ethyl}-3-(3,4-dimethylphenyl)propanamide (24-4) was prepared by the similar procedure with that described in above Example 1-5.

70% yield, white solid, mp=176-177° C.
$^1$H NMR (CDCl$_3$) δ7.47 (t, 1H, J=8 Hz), 6.9-7.1 (m, 5H), 6.43 (bs, 1H), 5.46 (d, 1H), 5.03 (m, 1H), 3.01 (s, 3H), 2.90 (t, 2H, J=7.3 Hz), 2.49 (dt, 2H), 2.23 (d, 6H, J=3.8 Hz), 1.37 (d, 3H, J=7 Hz)
MS (FAB) m/z 393 (MH$^+$)

Example 145

Preparation of N-{1-[3-Fluoro-4-(methylsulfonylamino)phenyl]ethyl}-3-(3,4-dimethylphenyl)-2-propenamide (24-5, CHK-651)

The N-{1-[3-Fluoro-4-(methylsulfonylamino)phenyl]ethyl}-3-(3,4-dimethylphenyl)-2-propenamide (24-5) was prepared by the similar procedure with that described in above Example 1-5.

74% yield, white solid, mp=212-213° C.
$^1$H NMR (CDCl$_3$) δ 7.59 (d, 1H, J=15.6 Hz), 7.54 (t, 1H, J=8 Hz), 7.1-7.26 (m, 5H), 6.46 (bs, 1H), 6.35 (d, 1H, J=15.6 Hz), 5.77 (d, 1H, J=7.7 Hz), 5.22 (m, 1H), 3.02 (s, 3H), 2.27 (bs, 6H), 1.53 (d, 3H, J=7 Hz)
MS (FAB) m/z 391 (MH$^+$)

Example 146

Preparation of N-{1-[3-Fluoro-4-(methylsulfonylamino)phenyl]ethyl}-3-(4-chlorophenyl)propenamide (24-6, KMJ-534)

The N-{1-[3-Fluoro-4-(methylsulfonylamino)phenyl]ethyl}-3-(4-chlorophenyl)propenamide (24-6) was prepared by the similar procedure with that described in above Example 1-5.

65% yield, white solid, mp=170-172° C.
$^1$H NMR (CDCl$_3$) δ 7.48 (t, 1H, J=8 Hz), 7.23 (d, 2H, J=8.3 Hz), 7.10 (d, 2H, J=8.3 Hz), 6.92-7.0 (m, 2H), 6.44 (bs, 1H), 5.47 (d, 1H), 5.03 (m, 1H), 3.03 (s, 3H), 2.94 (t, 2H, J=7.3 Hz), 2.48 (m, 2H), 1.38 (d, 3H, J=7 Hz)
MS (FAB) m/z 399 (MH$^+$)

Example 147

Preparation of N-{1-[3-Fluoro-4-(methylsulfonylamino)phenyl]ethyl}-3-(4-chlorophenyl)-2-propenamide (24-7, KMJ-558)

The N-{1-[3-Fluoro-4-(methylsulfonylamino)phenyl]ethyl}-3-(4-chlorophenyl)-2-propenamide (24-7) was prepared by the similar procedure with that described in above Example 1-5.

57% yield, white solid, mp=219-221° C.
$^1$H NMR (CDCl$_3$) δ 7.59 (d, 1H, J=15.7 Hz), 7.56 (t, 1H, J=8 Hz), 7.42 (d, 2H, J=8.3 Hz), 7.34 (d, 2H, J=8.3 Hz), 7.12-7.18 (m, 2H), 6.44 (bs, 1H), 6.37 (d, 1H, J=15.7 Hz), 5.77 (d, 1H), 5.22 (m, 1H), 3.02 (s, 3H), 1.54 (d, 3H, J=7 Hz)
MS (FAB) m/z 397 (MH$^+$)

Example 148

Preparation of N-{1-[3-Fluoro-4-(methylsulfonylamino)phenyl]ethyl}-3-(3,4-dimethylphenyl)butanamide (24-8, CHK-647)

The N-{1-[3-Fluoro-4-(methylsulfonylamino)phenyl]ethyl}-3-(3,4-dimethylphenyl)butanamide (24-8) was prepared by the similar procedure with that described in above Example 1-5.

81% yield, mp=152-154° C.
$^1$H NMR (CDCl$_3$) δ 7.52 (t, 1H, J=8 Hz), 6.85-7.1 (m, 5H), 6.46 (bs, 1H), 5.56 (d, 1H, J=7 Hz), 5.08 (m, 1H), 3.01 (s, 3H), 2.58 (t, 2H, J=7.3 Hz), 2.23 (s, 6H), 2.19 (t, 2H, J=7.9 Hz), 1.94 (m, 2H), 1.44 (d, 3H, J=7 Hz)
MS (FAB) m/z 407 (MH$^+$)

Experimental Example 1

Receptor Binding Affinity Assay Vanilloid Receptor 1 Binding Assays

Cell Culture

The pUHG102 VR1 plasmid was transfected into CHO cells containing the pTet Off regulatory plasmid (Clontech). In these cells, expression of the VR1 is repressed in the presence of tetracycline but is induced upon removal of the antibiotic. Stable clones were isolated in culture medium containing puromycin (10 μg/mL) and maintained in HAM F12 medium supplemented with tetracycline (1 μg/mL), 5 μg/ml geniticin, 25 mM HEPES, 10% FBS. Cells utilized for assays were grown in culture medium without antibiotic for 48 h before use. Cells were seeded in T75 cell culture flasks in media without antibiotics and grown to approximately 90% confluence. The flasks were then washed with PBS and harvested in 0.25% trypsin, 1 mM EDTA. The cells were pelleted by gentle centrifugation and stored at −20° C. until assay.

Competition Binding Assay

Binding studies with [$^3$H]resiniferatoxin (RTX) were carried out as described previously with minor modifications (Szallasi et al., 1992). Binding assay mixtures were set up on ice and contained 50-100 pM [$^3$H]RTX, various concentrations of competing ligands, 0.25 mg/mL BSA (Cohn fraction V), and about 5×10$^5$ VR1-transfected cells. The final volume was adjusted to 350 µL with DPBS with Ca$^{2+}$ and Mg$^{2+}$ and 0.25 mg/mL bovine serum albumin. Non-specific binding was determined in the presence of 100 nM nonradioactive RTX. The binding reaction was initiated by transferring the assay mixtures to a 37° C. water bath and was terminated after a 60 min incubation period by cooling the tubes on ice. To reduce non-specific binding, 200 µg/ml α-glycoprotein was added. Membrane-bound RTX was then separated from the free by pelleting the membranes in a Beckman 12 benchtop centrifuge (15 min, maximal velocity), the tips of the tubes containing the pellets were cut off, and the radioactivity was determined by scintillation counting. Equilibrium binding parameters (K$_i$ and cooperativity) were determined by fitting the Hill equation to the measured values with the aid of the program MicroCal Origin 6.0.

Compound Preparation

Initial stocks were dissolved in DMSO. For the binding assays, compounds were diluted in with DPBS with Ca$^{2+}$ and Mg$^{2+}$ and 0.25 mg/mL bovine serum albumin. For the calcium uptake assays, compounds were diluted in DMEM with 0.25 mg/mL bovine serum albumin.

Experimental Example 2

Functional Characterization for Agonist/Antagonist Activity $^{45}$Ca$^{2+}$-Uptake Assay Molecules were characterized to determine whether they were full agonists, partial agonists, or antagonists. For studies of $^{45}$Ca$^{2+}$ uptake by CHO/VR1 cells (Tet-off cells), the cells were plated in 24-well plates to yield a cell density 20-40% of that required to produce confluence. The next day the medium was changed to remove the tetracycline and induce VR1 expression. Experiments were performed approximately 36-40 hours after induction. For $^{45}$Ca$^{2+}$ uptake assay, cells were incubated for 5 min at 37° C. in a total volume of 400 µL of serum free DMEM (containing 1.8 mM CaCl$_2$) in the presence of 0.25 mg/mL BSA (Sigma), 1 µCi/mL $^{45}$Ca$^{2+}$ (5-30 Ci/g from ICN, CA), and increasing concentrations of the compound to be tested. Immediately after the incubation, extracellular $^{45}$Ca$^{2+}$ was removed by washing the cells three times with cold DPBS (containing 1.8 mM CaCl$_2$). Then 400 µl RIPA buffer (50 mM Tris pH 7.4; 150 mM NaCl; 1% Triton X-100; 0.1% SDS; 1% sodium deoxycholate) was added to each well in order to lyse the cells. Plates were shaken slowly for 20 min; then 306 µL of cell lysate was transferred from each well into a scintillation vial and radioactivity was determined by scintillation counting. For each data point in each experiment, four wells were assayed. Data from these experiments were analyzed by computer fit to the Hill equation. At least 3 separate experiments were carried out for each compound. In order to determine antagonist activity, studies were performed in exactly the same fashion with the exception that 50 nM capsaicin was added to the assay mixture to stimulate $^{45}$Ca$^{2+}$ uptake.

Experimental Example 3

Analgeisc Assay

Acetic Acid-Induced Writhing Test

Experimental protocols involving animals in this study were reviewed by the Animal Care and Use Committee of the College of Pharmacy, Seoul National University according to the NIH guidelines (NIH publication number 85-23, revised 1985) of "Principles of Laboratory Animal Care". Male ICR mice (Bio Genomics, Korea), weighing ~25 g, were maintained on a 12 hr light-dark cycle (light on between 6:00 p.m. and 6:00 a.m.) and allowed free access to food and water. The temperature and humidity of the animal room were maintained at 22±2° C. and 50±5%, respectively. Mice were allowed to habituate for ~30 min in the testing room on the day of experimentation. Animals then received an intraperitoneal injection of 0.3 mL of an acetic acid solution (1.2%, diluted in 0.9% saline), and were placed in a transparent acrylic cage. 5 min later the number of writhing movements (abnormal stretching) was counted for a 20 min period. Animals (10 animals/dose) were pretreated with test compounds or vehicle (0.2 mL, i.p.) 30 min before the injection of acetic acid. Test compounds were dissolved in either ethanol/Tween-80/saline (Oct. 10, 1980) mixture or Cremophor EL/DMSO/distilled water (Oct. 10, 1980) mixture. The effect of each compound was tested at 4-7 different doses. A reduction in the number of writhing movements compared to the vehicle-treatment group (the mean number of writhing movements in this group was 35) was considered to be indicative of an antinociceptive effect of a compound. The percentage antinociceptive efficiency (eff) was calculated as follows: % eff=100−[(# of writhing movements/# of writhing movement control)×100].

Data are expressed as ED$_{50}$ values that indicate the concentration at which a given compound reduces the number of writhing by 50% compared to that of a vehicle-treatment group. ED$_{50}$ values were obtained based on dose-response curves using mean data and fitted to by nonlinear regression analysis (Winnonlin version 3.1, Pharsight Corp., Mountainview, Calif.) on a PC.

Table 1 shows the potencies of vanilloid ligands for binding to rat VR1 and for inducing calcium influx in CHO/VR1 cells.

TABLE 1

| capsazepine | Compound # | K$_i$ (nM) Binding Affinity | K$_i$ (nM) Antagonism |
|---|---|---|---|
| | | 1300 | 520 |
| 1-51 | KMJ-372 | 58.4 | 5.47 |
| 1-52 | KMJ-470 | 30.7 | 29.5 |
| 1-53 | SH-173 | 7.41 | 24.9 |
| 1-54 | SH-168 | 23.3 | 29.9 |
| 1-55 | SH-285 | 19.9 | 7.38 |
| 1-56 | SH-219 | 344 | 467 |
| 1-57 | KMJ-806 | 6731 | NE |
| 1-58 | KMJ-788 | NE | NE |
| 1-59 | KMJ-838 | 1606 | 951 |
| 1-60 | KMJ-836 | 3712 | WE |
| 1-61 | YS-65 | WE | WE |
| 1-62 | YS-49 | WE | WE |
| 1-63 | YS-76 | WE | WE |
| 1-64 | YS-79 | NE | NE |
| 1-65 | CHK-717 | 536 | 232 |
| 1-66 | KMJ-708 | 358 | 120 |

TABLE 1-continued

| capsazepine | Compound # | $K_i$ (nM) Binding Affinity | $K_i$ (nM) Antagonism |
|---|---|---|---|
| 1-67 | KMJ-698 | 1423 | 4480 |
| 2-7 | KMJ-750 | 105 | 17.5 |
| 2-8 | YS-85 | 3500 | 1089 |
| 2-9 | YS-97 | 1652 | 253 |
| 3-5 | SU-834 | 43.9 | 6.87 |
| 3-6 | SU-824 | 458 | 102 |
| 4-1 | SH-291 | 1055 | 367 |
| 4-2 | SH-290 | 729 | 447 |
| 4-3 | SH-335 | 541 | 296 |
| 4-4 | SH-94 | 199 | 115 |
| 4-5 | SH-286 | 289 | 176 |
| 4-6 | SH-337 | 226 | 89.6 |
| 4-7 | SH-351 | | |
| 4-8 | KMJ-928 | 127 | 143 |
| 4-9 | SH-353 | WE | 1350 |
| 4-10 | SH-93 | 657 | 274 |
| 4-11 | KMJ-498 | 1746 | 261 |
| 4-12 | SH-92 | 959 | 239 |
| 4-13 | SH-112 | NE | NE |
| 4-14 | KMJ-374 | 553 | 42.6 |
| 4-15 | SU-770 | 412 | 97.4 |
| 4-16 | SU-774 (R) | 944 | 204 |
| 4-17 | SU-776 (S) | 236 | 33.7 |
| 4-18 | KMJ-686 | 277 | 152 |
| 4-19 | KMJ-518 | 466 | 135 |
| 4-20 | KMJ-732 | 897 | 384 |
| 4-21 | SH-109 | 9417 | WE |
| 4-22 | SH-130 | 5859 | WE |
| 4-23 | SH-116 | 1697 | 2487 |
| 4-24 | KMJ-378 | 128 | 36.6 |
| 4-25 | KMJ-724 | 21.5 | 14.2 |
| 4-26 | KMJ-908 | 36.0 | 8.03 |
| 4-27 | SH-135 | 43.3 | 29.3 |
| 4-28 | SH-199 | 141 | 121 |
| 5-1 | CHK-512 | 119 | 38.0 |
| 5-2 | CHK-514 | 55.2 | 52.0 |
| 5-3 | SU-542 | 33.1 | 10.78 |
| 5-4 | SU-564 | 13.6 | 3.24 |
| 5-5 | CHK-479 | 71.2 | 13.6 |
| 5-6 | CHK-499 | 24.0 | NE |
| 5-7 | KMJ-472 | 11.3 | 35.7 |
| 5-8 | KMJ-690 | 3.62 | 12.3 |
| 6-1 | SU-730 | 12792 | 1468 |
| 6-2 | SU-634 | WE | WE |
| 6-3 | SU-636 | WE | WE |
| 6-4 | SU-728 | NE | NE |
| 6-5 | SU-826 | 43.4 | 8.55 |
| 6-6 | SU-830 | 20.3 | 10.0 |
| 6-7 | SU-838 | 372 | 205 |
| 6-8 | SU-818 | 297 | 98.3 |
| 6-9 | MK-271 | 4.24 | 0.58 |
| 6-10 | MK-272 | 6.58 | 10.9 |
| 6-11 | MK-450 | 63.8 | 142 |
| 6-12 | MK-452 | 53.0 | 30.3 |
| 6-13 | MK-453 | 1.83 | 5.23 |
| 6-14 | MK-451 | 3.29 | 12.1 |
| 9-1 | CHK-520 | 372 | 103 |
| 9-2 | CHK-543 | 276 | 65.4 |
| 9-3 | CHK-493 | 152 | 133 |
| 9-4 | CHK-591 | 1696 | 573 |
| 9-5 | CHK-656 | 960 | 418 |
| 9-6 | CHK-600 | 838 | 366 |
| 9-7 | CHK71 | 425 | 2552 |
| 9-8 | CHK-655 | 1069 | 467 |
| 9-9 | CHK- | | |
| 12-1 | CHK-533 | 396 | 197 |
| 12-2 | CHK-538 | 1577 | 567 |
| 12-3 | CHK-541 | 238 | 117 |
| 12-4 | CHK-590 | 1735 | 1103 |
| 12-5 | | | |
| 12-6 | CHK-632 | 1699 | 1242 |
| 12-7 | CHK-719 | 608 | 1763 |
| 12-8 | CHK-659 | | |
| 12-9 | CHK-718 | 745 | 2252 |
| 15-1 | LJO-303 | 59.3 | 14.7 |
| 15-2 | LJO-328 | 54 | 9.16 |
| 15-3 | CHK-575 | 66.5 | 28.6 |
| 15-4 | YHS-187 | 163 | 65.8 |
| 15-5 | YHS-209 | 2769 | NE |
| 16-5 | SU-388 | 40.8 | 4.52 |
| 16-6 | SU-400 | 3594 | NE |
| 17-7 | CJU-032 | 32.8 | 39.4 |
| 17-8 | CJU-039 | 2579 | 4314 |
| 18-1 | MK-229 | 22.7 | 44.5 |
| 18-2 | MK-202 | 19.4 | 89 |
| 18-3 | MK-230 | 1138 | 3474 |
| 18-4 | MK-228 | 706 | 133 |
| 18-5 | LJO-388 | 37.2 | 25.9 |
| 18-6 | SU-472 | 6.1 | 6.86 |
| 18-7 | SU-512 | 15.2 | 7.14 |
| 18-8 | | | |
| 18-9 | LJO-401 | 42.7 | 28.7 |
| 18-10 | MK-296 | 9.95 | 23.9 |
| 18-11 | MK-334 | 15.7 | 53.0 |
| 18-12 | MK-298 | 8.09 | 30.6 |
| 18-13 | LJO-344 | 37 | 7.09 |
| 18-14 | LJO-366 | 37 | 9.34 |
| 19-13 | SU-692 | 420 | 193 |
| 19-14 | SU-704 | 272 | 290 |
| 19-15 | SU-720 | NE | WE |
| 19-16 | SU-710 | NE | WE |
| 20-12 | LJO-399 | 230 | 54.3 |
| 20-13 | LJO-402 | 338 | 223 |
| 20-14 | LJO-403 | 100 | 861 |
| 20-15 | LJO-395 | 1741 | 695 |
| 21-7 | CHK-593 | WE | 1827 |
| 21-8 | CHK-660 | 7741 | 983 |
| 21-9 | CHK-629 | 2888 | 663 |
| 22-7 | CHK-579 | 171 | 60.3 |
| 22-8 | | | |
| 22-9 | CHK-631 | 372 | 243 |
| 23-1 | MK-82 | 1193 | 544 |
| 23-2 | MK-205 | 447 | 298 |
| 24-1 | KMJ-586 | 2129 | 2216 |
| 24-2 | KMJ-552 | 376 | 103 |
| 24-3 | KMJ-570 | 104 | 23.9 |
| 24-4 | CHK-602 | NE | 4129 |
| 24-5 | CHK-651 | 2525 | 1354 |
| 24-6 | KMJ-534 | WE | 5651 |
| 24-7 | KMJ-558 | 773 | 938 |
| 24-8 | CHK-647 | 3529 | 988 |

NE: not effecive,
WE: weakly effective

Experimental Example 4

Toxicity Test

The acute toxicity tests on ICR mice (mean body weight 25±5 g) and Sprague-Dawley rats (235±10 g) were performed using the compounds 35 and 37. Each group consisting of 3 mice or rats was administrated intraperitoneally with 20 mg/kg, 10 mg/kg and 1 mg/kg of test compounds or solvents (0.2 ml, i.p.), respectively and observed for 24 hrs.

There were no treatment-related effects on mortality, clinical signs, body weight changes and gross findings in any group or either gender. These results suggested that the compounds prepared in the present invention were potent and safe.

Hereinafter, the formulating methods and kinds of excipients will be described, but the present invention is not limited to them. The representative preparation examples were described as follows.

| Preparation of powder | |
|---|---|
| Compound 35 | 500 mg |
| Corn Starch | 100 mg |
| Lactose | 100 mg |
| Talc | 10 mg |

Powder preparation was prepared by mixing above components and filling sealed package.

| Preparation of tablet | |
|---|---|
| Compound 37 | 100 mg |
| Corn Starch | 100 mg |
| Lactose | 100 mg |
| Magnesium Stearate | 2 mg |

Tablet preparation was prepared by mixing above components and entabletting.

| Preparation of capsule | |
|---|---|
| Compound 35 | 50 mg |
| Lactose | 50 mg |
| Magnesium Stearate | 1 mg |

Tablet preparation was prepared by mixing above components and filling gelatin capsule by conventional gelatin preparation method.

| Preparation of injection | |
|---|---|
| Compound 37 | 100 mg |
| Distilled water for injection | optimum amount |
| PH controller | optimum amount |

Injection preparation was prepared by dissolving active component, controlling pH to about 7.5 and then filling all the components in 2 ml ample and sterilizing by conventional injection preparation method.

| Preparation of liquid | |
|---|---|
| Compound 35 | 1 g |
| Sugar | 10 g |
| Citric acid | 0.05~0.3% |
| Vitamin C | 0.1~1% |
| Lemon flavor | optimum amount |
| Distilled water | optimum amount |

Liquid preparation was prepared by dissolving active component, adding lemon flavor and distilled water and then filling all the components in 100 ml brown bottle and sterilizing by conventional liquid preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

The novel 4-(methylsulfonylamino)phenyl analogues as vanilloid antagonist and the pharmaceutical composition comprising same according to the present invention act as vanilloid receptor-1 antagonists and analgesics so the inventive compounds are useful in the prevention, alleviation or treatment of pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease, inflammatory disease or urgent urinary incontinence, etc.

The invention claimed is:

1. A compound corresponding to formula (I) or a pharmaceutically acceptable salt or isomer thereof:

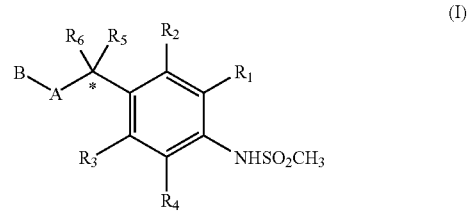

(I)

wherein:

A is CONH, NHCO, or NHC(=O)NH;

$R_1$ to $R_4$ is independently a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, or a 5 or 6-member heterocyclic ring;

$R_5$ and $R_6$ are independently a hydrogen, hydroxyl group, amino group, straight or branched alkyl group having 1 to 6 carbon atoms, a cycloalkyl group having 1 to 6 carbon atoms, or a phenyl or benzyl group optionally substituted with at least one substituent selected from the group consisting of halogen atom, an amine group, and an alkyl group having 1 to 6 carbon atoms, provided that both of $R_5$ and $R_6$ are not hydrogen atoms simultaneously;

B is a group selected from

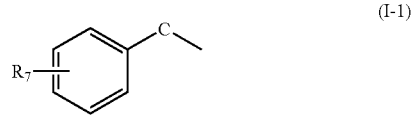

(I-1)

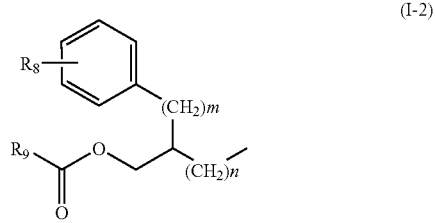

(I-2)

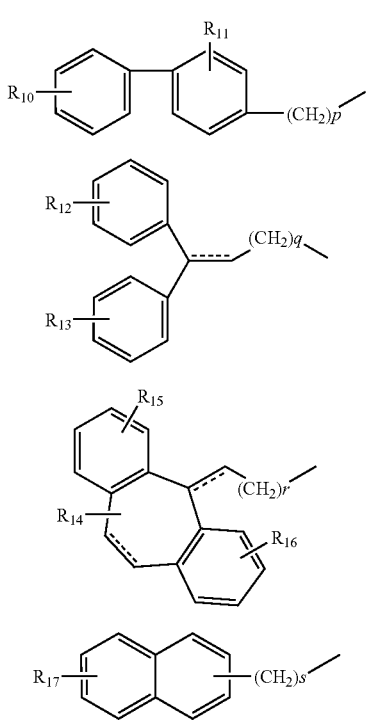

in which $R_7$ to $R_{17}$ is independently a hydrogen atom, a halogen atom, or a straight or branched alkyl group having 1 to 6 carbon atoms optionally substituted with more than one halogen atom;

C is an alkyl, alkenyl, or alkynyl group having 1 to 5 carbon atoms which may include one or more heteroatoms, wherein each of m, n, p, q, r, and s is an integer of 0 to 3; and an asteric mark * indicates a chiral carbon atom; and
( ═══ ) mark indicates a double bond or single bond chain.

2. A compound according to claim 1, corresponding to formula (II) or a pharmaceutically acceptable salt or isomer thereof:

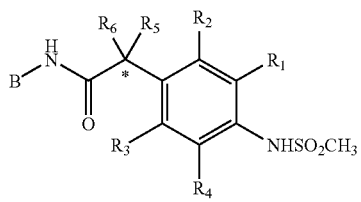

wherein, $R_1$ to $R_4$ is independently a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, or a five or six-member heterocyclic ring; and $R_5$ and $R_6$ are independently a hydrogen, hydroxyl group, amino group, straight or branched alkyl group having 1 to 6 carbon atoms, cycloalkyl group having 1 to 6 carbon atoms or a phenyl or benzyl group optionally substituted with at least one substituent selected from the group consisting of halogen atom, amine group and alkyl group having 1 to 6 carbon, provided that both of $R_5$ and $R_6$ are not hydrogen simultaneously.

3. A compound according to claim 2, wherein said compound is at least one selected from the group consisting of:

N-(4-tert-butylbenzyl)-2-[3-fluoro-4-(methylsulfonylamino)phenyl]propionamide (1-51, KMJ-372), N-(4-tert-butylbenzyl)-2-[3-chloro-4-(methylsulfonylamino)phenyl]propionamide (1-52, KMJ-470), N-(4-tert-butylbenzyl)-2-[3-bromo-4-(methylsulfonylamino)phenyl]propionamide (1-53, SH-173), N-(4-tert-butylbenzyl)-2-[3-iodo-4-(methylsulfonylamino)phenyl]propionamide (1-54, SH-168), N-(4-tert-butylbenzyl)-2-[3,5-difluoro-4-(methylsulfonylamino)phenyl]-propionamide (1-55, SH-285), N-(4-tert-butylbenzyl)-2-[3-cyano-4-(methylsulfonylamino)phenyl]propionamide (1-56, SH-219), N-(4-tert-butylbenzyl)-2-[3-methoxycarbonyl-4-(methylsulfonylamino)phenyl]-propionamide (1-57, JMJ-806), N-(4-tert-butylbenzyl)-2-[3-carboxyl-4-(methylsulfonylamino)phenyl]-propionamide (1-58, KMJ-788), N-4(tert-butylbenzyl)-2-[3-methoxycarbonyl-4-(methylsulfonylamino)phenyl]-propionamide (1-59, KMJ-838), N-(4-tert-butylbenzyl)-2-[3-(benzylamino)carbonyl-4-(methylsulfonylamino)-phenyl]propionamide (1-60, KMJ-836), N-(4-tert-butylbenzyl)-2-[3-piperidino-4-(methylsulfonylamino)phenyl]-propionamide (1-61, YS-65), N-(4-tert-butylbenzyl)-2-[3-morpholino-4-(methylsulfonylamino)phenyl]-propionamide (1-62, YS-49), N-(4-tert-butylbenzyl)-2-[3-(N-Boc)piperazino-4-(methylsulfonylamino)phenyl]-propionamide (1-63, YS-76), N-(4-tert-butylbenzyl)-2-[3-piperazino-4-(methylsulfonylamino)phenyl]-propionamide (1-64, YS-79), N-(4-tert-butylbenzyl)-2-[3-methoxy-4-(methylsulfonylamino)phenyl]-propionamide (1-65, CHK-717), N-(4-tert-butylbenzyl)-2-[2-fluoro-4-(methylsulfonylamino)phenyl]propionamide (1-66, KMJ-708), N-(4-tert-butylbenzyl)-2-[2-chloro-4-(methylsulfonylamino)phenyl]propionamide (1-67, KMJ-698), N-(4-tert-butylbenzyl)-2-[4-(methylsulfonylamino)phenyl]propionamide (2-7, KMJ-750), N-(4-chloro)-2-[4-(methylsulfonylamino)phenyl]propionamide (2-8, YS-85), N-(3,4-dichloro)-2-[4-(methylsulfonylamino)phenyl]propionamide (2-9, YS-97), N-(4-tert-butylbenzyl)-(2S)-2-[3-fluoro-4-(methylsulfonylamino)phenyl]-propionamide (3-5, SU-834), N-(4-tert-butylbenzyl)-(2R)-2-[3-fluoro-4-(methylsulfonylamino)phenyl]-propionamide (3-6, SU-824), N-(4-chlorobenzyl)-2-[3-fluoro-4-(methylsulfonylamino)phenyl]propionamide (4-1, SH-291), N-(4-chlorobenzyl)-2-[3-chloro-4-(methylsulfonylamino)phenyl]propionamide (4-2, SH-290), N-(4-chlorobenzyl)-2-[3-bromo-4-(methylsulfonylamino)phenyl]propionamide (4-3, SH-335), N-(3,4-dichlorobenzyl)-2-[3-fluoro-4-(methylsulfonylamino)phenyl]propionamide (4-4, SH-94), N-(3,4-dichlorobenzyl)-2-[3-chloro-4-(methylsulfonylamino)phenyl]propionamide (4-5, SH-286), N-(3,4-dichlorobenzyl)-2-[3-bromo-4-(methylsulfonylamino)phenyl]propionamide (4-6, SH-337), N-(4-methylbenzyl)-2-[3-fluoro-4-(methylsulfonylamino)phenyl]propionamide (4-7, SH-351), N-(4-isopropylbenzyl)-2-[3-fluoro-4-(methylsulfonylamino)phenyl]propionamide (4-8, KMJ-928),
N-(4-methoxybenzyl)-2-[3-fluoro-4-(methylsulfonylamino)phenyl]propionamide (4-9, SH-353),
N-(4-trifluoromethylbenzyl)-2-[3-fluoro-4-(methylsulfonylamino)phenyl]-propionamide (4-10, SH-93),
N-(4-phenylbenzyl)-2-(3-fluoro-4-(methylsulfonylamino)phenyl]propionamide (4-11, KMJ-498),
N-(1-naphthylmethyl)-[3-fluoro-4-(methylsulfonylamino)phenyl]propionamide (4-12, SH-92),
N-(1,2,3,4-tetrahydro-1-naphthalenyl)-2-[3-fluoro-4-methylsulfonylamino)phenyl-propionamide (4-13, SH-112),
N-[2-(4-tert-butylphenyl)ethy]-2-[3-fluoro-4-(methylsulfonylamino)phenyl]-propionamide (4-14, KMJ-374),
N-[3-(3,4-dimethylphenyl)propyl]-2-[3-fluoro-4-methylsulfonylamino)phenyl]-propionamide (4-15, SU-770),
N-[3-(3,4-dimethylphenyl)propyl]-(2R)-2-[3-fluoro-4-methylsulfonylamino)-phenyl]propionamide (4-16, SU-774),
N-[3-(3,4-dimethylphenyl)propyl]-(2S)-2-[3-fluoro-4-methylsulfonylamino)-phenyl]propionamide (4-17, SU-776),
N-[3-(3,4-dimethylphenyl)-2-propenyl]-2-[3-fluoro-4-(methylsulfonylamino)-phenyl]propionamide (4-18, KMJ-686),
N-[3-(4-chlorophenyl)propyl]-2-[3-fluoro-4-methylsulfonylamino)phenyl]-propionamide (4-19, KMJ-518),
N-[3-(4-chlorophenyl)-2-prophenyl]-2-[3-fluoro-4-methylsulfonylamino)phenyl]-propionamide (4-20, KMJ-732),
N-benzyloxy-2-[3-fluoro-4-(methylsulfonylamino)phenyl]propionamide (4-21, SH-109),
N-(benzhydryl)-2-[3-fluoro-4-(methylsulfonylamino)phenyl]propionamide (4-22, SH-130),
N-(2,2-diphenylethyl)-2-[3-fluoro-4-(methylsulfonylamino)phenyl]propionamide (4-23, SH-116),
N-(3,3-diphenylpropyl)-2-[3-fluoro-4-(methylsulfonylamino)phenyl]propionamide (4-24, KMJ-378),
N-(3,3-diphenyl-2-prophenyl)-2-[3-fluoro-4-methylsulfonylamino)phenyl]-propionamide (4-25, KMJ-724),
N-[3,3-di(4-methylphenyl)-2-propenyl]-2-[3-fluoro-4-methylsulfonylamino)-phenyl]propionamide (4-26, KMJ-908),
N-[3,3-di(4-fluorophenyl)-2-prophenyl]-2-[3-fluoro-4-(methylsulfonylamino)-phenyl]propionamide (4-27, SH-135),
N-[2-(10,11-dihydro-5H-dibenzo[a,d]cyclohepten-5-yliden)ethyl]-2-[3-fluoro-4-(methylsulfonylamino) phenyl]propionamide (4-28, SH-199),
N-[2-(3,4-dimethylbenzyl)-3-pivaloxypropyl]-2-[4-(methylsulfonylamino)phenyl]-propionamide (5-1, CHK-512),
N-[2-(4-tert-butylbenzyl)-3-pivaloxypropyl]-2-[4-(methylsulfonylamino)phenyl]-propionamide (5-2, CHK-514),
2-[3-fluoro-4-(methylsulfonylamino)phenyl]-N-[2-(3,4-dimethylbenzyl)-3-pivaloxypropyl]propionamide (5-3, SU-542),
2-[3-fluoro-4-(methylsulfonylamino)phenyl]-N-[2-4-tert-butylbenzyl)-3-pivaloxypropyl]propionamide (5-4, SU-564),
N-[2-(3,4-dimethylbenzyl)-3-pivaloxypropyl]-2-[3-methoxy-4-(methylsulfonyl-amino)phenyl]propionamide (5-5, CHK-479),
N-[2-(4-tert-butylbenzyl)-3-pivaloxypropyl]-2-[3-methoxy-4-methylsulfonylamino) phenyl]propionamide (5-6, CHK-499),
N-[2-(3,4-dimethylbenzyl)-3-pivaloxypropyl]-2-[3-chloro-4-(methylsulfonylamino)-phenyl]propionamide (5-7, KNJ-472),
N-[2-(4-tert-butylbenzyl)-3-pivaloxypropyl]-2-[3-chloro-4-(methylsulfonylamino)-phenyl]propionamide (5-8, KMJ-690),
N-[(1R)-1-benzyl-2-(pivaloxy)ethyl]-(2S)-2-[3-fluoro-4-(methylsulfonylamino)-phenyl]propionamide (6-1, SU-730)*
N-[(1S)-1-benzyl-2-(pivaloxy)ethyl]-(2S)-2-[3-fluoro-4-(methylsulfonylamino)-phenyl]propionamide (6-2, SU-634),
N-[(1S)-1-benzyl-2-(pivaloxy)ethyl]-(2R)-2-[3-fluoro-4-methylsulfonylamino)-phenyl]propionamide (6-3, SU-636),
N-[(1R)-1-benzyl-2-(pivaloxy)ethyl]-(2R)-2-[3-fluoro-4-(methylsulfonylamino)-phenyl]propionamide (6-4, SU-728),
N-[(2R)-2-benzyl-3-(pivaloxy)propyl]-(2S)-2-[3-fluoro-4-(methylsulfonylamino)-phenyl]propionamide (6-5, SU-826),
N-[(2S)-2-benzyl-3-(pivaloxy)propyl]-(2S)-2-[3-fluoro-4-(methylsulfonylamino)-phenyl]propionamide (6-6, SU-830),
N-[(2S)-2-benzyl-3-(pivaloxy)propyl]-(2R)-2-[3-fluoro-4-(methylsulfonylamino)-phenyl]propionamide (6-7, SU-838),
N-[(2R)-2-benzyl-3-(pivaloxy)propyl]-(2R)-2-[3-fluoro-4-(methylsulfonylamino)-phenyl]propionamide (6-8, SU-818),
N-[(2R)-2-(4-tert-butyl)benzyl-3-(pivaloxy)propyl]-(2S)-2-[3-fluoro-4-(methylsulfonylamino)phenyl]propionamide (6-9, MK-271),
N-[(2S)-2-(4-tert-butyl)benzyl-3-(pivaloxy)propyl]-(2S)-2-[3-fluoro-4-(methylsulfonylamino)phenyl]propionamide (6-10, MK-272),
N-[(2S)-2-(4-tert-butyl)benzyl-3-(pivaloxy)propyl]-(2R)-2-[3-fluoro-4-(methylsulfonylamino)phenyl]propionamide (6-11, MK-450),
N-[(2R)-2-(4-tert-butyl)benzyl-3-(pivaloxy)propyl]-(2R)-2-[3-fluoro-4-(methylsulfonylamino)phenyl]propionamide (6-12, MK-452),
N-[(2R)-2-(4-tert-butyl)benzyl-3-(pivaloxy)propyl]-(2S)-2-[3-chloro-4-(methylsulfonylamino)phenyl]propionamide (6-13, MK-453),
N-[(2S)-2-(4-tert-butyl)benzyl-3-(pivaloxy)propyl]-(2S)-2-[3-chloro-4-(methylsulfonylamino)phenyl]propionamide (6-14, MK-451),
2-[3-fluoro-4-(methylsulfonylamino)phenyl-2-methylpropionic acid (7-4, CHK-624),
2-(4-(methylsulfonylamino)phenyl]-2-methylpropionic acid (8-11),
2-[3-methoxy-4-(methylsulfonylamino)phenyl]-2-methylpropionic acid (8-12),
N-[2-(3,4-dimethylbenzyl)-3-pivaloxypropyl]-2-[4-(methylsulfonylamino)phenyl]-2-methylpropionamide (9-1, CHK-520),
N-[2-(3,4-dimethylbenzyl)-3-pivaloxypropyl]-2-[3-fluoro-4-(methylsulfonylamino)-phenyl]-2-methylpropionamide (9-2, CHK-543),
N-[2-(3,4-dimethylbenzyl)-3-pivaloxypropyl]-2-[3-methoxy-4-(methylsulfonyl-amino)phenyl]-2-methylpropionamide (9-3, CHK-493), N-[3-(3,4-dimethylphenyl)propyl]-2-[4-(methylsulfonylamino)phenyl]-2-methyl-propionamide (9-4, CHK-591), N-[3-(3,4-dimethylphenyl)propyl]-2-[3-fluoro-4-(methylsulfonylamino)phenyl]-2-methylpropionamide (9-5, CHK-656), N-[3-(3,4-dimethylphenyl)propyl]-2-[-3-methoxy-4-(methylsulfonylamino)phenyl]-2-methylpropionamide (9-6, CHK-600), N-(4-tert-butylbenzyl)-2-[4-(methylsulfonylamino)phenyl]-2-methylpropionamide (9-7, CHK-715), N-(4-tert-butylbenzyl)-2-[3-fluoro-4-(methylsulfonylamino)phenyl]-2-methyl-propionamide (9-8, CHK-655), N-(4-tert-butylbenzyl)-2-[3-methoxy-4-(methylsulfonylamino)phenyl]-2-methyl-propionamide (9-9), 1-[3-fluoro-4-(methylsulfonylamino)phenyl]cyclopropane carboxylic acid (10-5), 1-[4-(methylsulfonylamino)phenyl]cyclopropane carboxylic acid (11-7, CHK-530), 1-[3-methoxy-4-(methylsulfonylamino)phenyl]cyclopropane carboxylic acid (11-8), N-[2-(3,4-dimethylbenzyl)-3-pivaloxypropyl]-1-[4-(methylsulfonylamino)phenyl]cyclopropane carboxamide (12-1, CHK-533), N-[2-(3,4-dimethylbenzyl)-3-pivaloxypropyl]-1-[3-fluoro-4-(methylsulfonylamino)-phenyl]cyclopropane carboxamide (12-2, CHK-538), N-[2-(3,4-dimethylbenzyl)-3-pivaloxypropyl]-1-[3-methoxy-4-(methylsulfonyl-amino)phenyl]cyclopropane carboxamide (12-3, CHK-541), N-[3-(3,4-dimethylphenyl)propyl]-1-[4-(methylsulfonylamino)phenyl]-cyclopropane carboxamide (12-4, CHK-590), N-[3-(3,4-dimethylphenyl)propyl]-1-[3-fluoro-4-(methylsulfonylamino)phenyl]-cyclopropane carboxamide (12-5), N-[3-(3,4-dimethylphenyl)propyl]-1-[3-methoxy-4-(methylsulfonylamino)phenyl]-cyclopropane carboxamide (12-6, CHK-632), N-(4-tert-butylbenzyl)-1-[4-(methylsulfonylamino)phenyl]cyclopropane carboxamide (12-7, CHK-719), N-(4-tert-butylbenzyl)-1-[3-fluoro-4-(methylsulfonylamino)phenyl]cyclopropane carboxamide (12-8, CHK-659), and N-(4-tert-butylbenzyl)-1-[3-methoxy-4-(methylsulfonylamino)phenyl]cyclopropane carboxamide (12-9, CHK-718).

4. A compound according to claim 1, corresponding to formula (IV), or a pharmaceutically acceptable salt or isomer thereof:

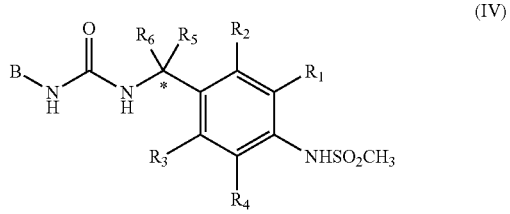

(IV)

wherein, $R_1$ to $R_4$ is independently a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, or five or six-member heterocyclic ring; and $R_5$ and $R_6$ are independently a hydrogen, hydroxyl group, amino group, straight or branched alkyl group having 1 to 6 carbon atoms, cycloalkyl group having 1 to 6 carbon atoms, or a phenyl or benzyl group optionally substituted with at least one substituent selected from the group consisting of a halogen atom, amine group and alkyl group having 1 to 6 carbons, provided that both of $R_5$ and $R_6$ are not hydrogen atoms simultaneously.

5. A compound according to claim 4, wherein said compound is

N-(4-tert-butylbenzyl)-N'-1-[4-(methylsulfonylamino)phenyl]ethyl}urea (23-1, MK-82), or N-(4-tert-butylbenzyl)-N'-1-[3-fluoro-4-(methylsulfonylamino)phenyl]ethyl}-urea (23-2, MK-205).

6. A compound according to claim 1, corresponding to formula (V), or a pharmaceutically acceptable salt or isomer thereof:

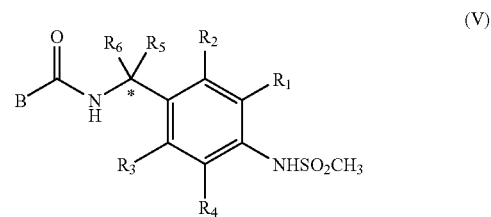

(V)

wherein, $R_1$ to $R_4$ is independently a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, or a five or six-member heterocyclic ring; and $R_5$ and $R_6$ are independently a hydrogen, hydroxyl group, amino group, straight or branched alkyl group having 1 to 6 carbon atoms, cycloalkyl group having 1 to 6 carbon atoms, or a phenyl or benzyl group optionally substituted with at least one substituent selected from the group consisting of halogen atoms, amine groups and alkyl groups having 1 to 6 carbons, provided that both of $R_5$ and $R_6$ are not hydrogen atoms simultaneously.

7. A compound according to claim 6, wherein said compound is selected from the group consisting of:

N-{1-[3-fluoro-4-(methylsulfonylamino)phenyl]ethyl}-3-(4-tert-butylphenyl)-acetamide (24-1, KMJ-586), N-1-[3-fluoro-4-(methylsulfonylamino)phenyl]ethyl}-3-(4-tert-butylphenyl)-propanamide (24-2, KMJ-552), N-{1-[3-fluoro-4-(methylsulfonylamino)phenyl]ethyl}-3-(4-tert-butylphenyl)-2-propanamide (24-3, KMJ-570), N-{1-[3-fluoro-4-(methylsulfonylamino)phenyl]ethyl}-3-(3,4-dimethylphenyl)-propanamide (24-4, CHK-602), N-1-[3-fluoro-4-(methylsulfonylamino)phenyl]ethyl}-3-(3,4-dimethylphenyl)-2-propanamide (24-5, CHK-651), N-1-[3-fluoro-4-(methylsulfonylamino)phenyl]ethyl}-3-(3,4-dimethylphenyl) propanamide (24-6, CHK-534), N-{1-[3-fluoro-4-(methylsulfonylamino)phenyl]ethyl}-3-(4-chlorophenyl)-2-propanamide (24-7, KMJ-558), and N-{1-[3-fluoro-4-(methylsulfonylamino)phenyl]ethyl}-3-(3,4-dimethylphenyl)-butanamide (24-8, CHK-647).

8. A compound according to claim 1, wherein $R_1$ to $R_4$ is independently a hydrogen, halogen atom, cyano group, nitro group, lower alkyl amine, lower alkoxy group having 1 to 3 carbon atoms, carboxylic acid, hydroxamic acid, alkyl ester group having 1 to 6 carbon atoms, alkyl amide group having 1 to 6 carbon atoms, benzylamide group, or a five or six-member heterocyclic ring.

9. A compound according to claim 1, wherein $R_5$ and $R_6$ are independently a hydrogen, hydroxyl group, amino group, straight or branched alkyl group having 1 to 6 carbon atoms, cycloalkyl group having 1 to 6 carbon atoms, or a phenyl or benzyl group optionally substituted with at least one substituent selected from the group consisting of a halogen atom, amine group or an alkyl group having 1 to 6 carbons.

10. A pharmaceutical composition comprising a compound according to claim 1 as an active ingredient in an effective vanilloid receptor antagonizing amount, together with a pharmaceutically acceptable carrier or diluent.

11. A method of treating acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder, irritation of skin, eye or mucous membrane, fervescence, coughing, stomach-duodenal ulcer, or inflammatory bowel disease caused by the vanilloid receptor antagonistic activity, in a patient suffering therefrom, said method comprising administering to said patient a pharmaceutically effective amount of at least one compound according to claim 1.

12. Method of treating or inhibiting pain or inflammation, in a patient suffering therefrom, said method comprising administering to said patient a pharmaceutically effective amount of at least one compound according to claim 1.

13. The method according to claim 11, wherein the respiratory disorder is asthma or chronic obstructive pulmonary disease.

* * * * *